United States Patent
Bamba et al.

(10) Patent No.: US 8,575,179 B2
(45) Date of Patent: Nov. 5, 2013

(54) DIHYDROPYRAZOLOPYRIMIDINONE DERIVATIVES

(75) Inventors: Makoto Bamba, Ibaraki (JP); Satoshi Sunami, Ibaraki (JP)

(73) Assignee: MSD K.K., Chiyoda-Ku, Tokyo (JP)

( * ) Notice: Subject to any disclaimer, the term of this patent is extended or adjusted under 35 U.S.C. 154(b) by 20 days.

(21) Appl. No.: 13/133,671

(22) PCT Filed: Dec. 9, 2009

(86) PCT No.: PCT/JP2009/070932
§ 371 (c)(1),
(2), (4) Date: Jun. 9, 2011

(87) PCT Pub. No.: WO2010/067888
PCT Pub. Date: Jun. 17, 2010

(65) Prior Publication Data
US 2011/0245229 A1  Oct. 6, 2011

(30) Foreign Application Priority Data
Dec. 12, 2008 (JP) .................. 2008-316424

(51) Int. Cl.
  *A01N 43/90* (2006.01)
  *A61K 31/519* (2006.01)
  *C07D 487/00* (2006.01)

(52) U.S. Cl.
  USPC ...................... 514/262.1; 544/256

(58) Field of Classification Search
  None
  See application file for complete search history.

(56) References Cited

FOREIGN PATENT DOCUMENTS

| WO | 9961444 A2 | 12/1999 | |
|---|---|---|---|
| WO | WO99/61444 * | 12/1999 | ........... C07D 487/04 |
| WO | 2004011465 A1 | 2/2004 | |
| WO | 2004041822 A1 | 5/2004 | |
| WO | 2004041823 A1 | 5/2004 | |
| WO | 2004089955 A1 | 10/2004 | |
| WO | 2005011597 A2 | 2/2005 | |
| WO | 2006/135824 A1 | 12/2006 | |
| WO | 2007/126122 A1 | 11/2007 | |
| WO | 2008153207 A1 | 12/2008 | |
| WO | 2009151997 A1 | 12/2009 | |

OTHER PUBLICATIONS

Wolff et. al., "Burger's Medicinal Chemistry and Drug Discovery," 5th Ed. Part 1, pp. 975-977 (1995).*
Banker, et. al., (1996), Modern Pharmaceuticals, p. 596.*
Palmer B.D. et al, Structure-activity relationships for 2-anilino-6-phenylpyrido[2,3-d]pyrimidin-7(8H)-ones as inhibitors of the cellular checkpoint kinase Wee1, Bioorganic & Medicinal Chemistry Letters, vol. 15, No. 7, Apr. 1, 2005, pp. 1931-1935.

* cited by examiner

*Primary Examiner* — Jeffrey Murray
(74) *Attorney, Agent, or Firm* — Joan E. Switzer; David A. Muthard

(57) ABSTRACT

The invention relates to compounds represented by the general formula (I) and the like. In the formula, $Ar^1$ denotes an aryl or heteroaryl group which may have a substituent; $R_1$ denotes a hydrogen atom, or denotes a C1-C6 alkyl, aryl, aralkyl or heteroaryl group which may have a substituent; $R_2$ denotes an aralkyl group or a group represented by the formula (a); and $R_3$ denotes a hydrogen atom or a C1-C6 alkyl group. The compounds of the invention have an excellent Wee1 kinase inhibitory effect, and therefore are useful in the field of medicine, especially in the field of treatment of various cancers.

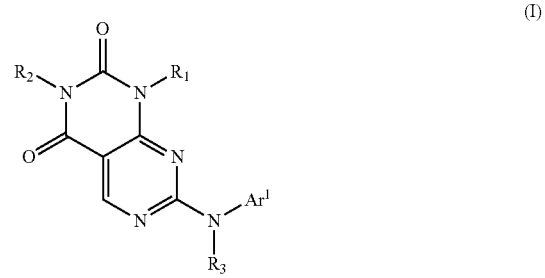

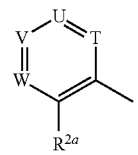

11 Claims, No Drawings

DIHYDROPYRAZOLOPYRIMIDINONE DERIVATIVES

TECHNICAL FIELD

The present invention is useful in the field of medicine. More particularly, the dihydropyrimidopyrimidine derivatives of the invention are useful in the field of treatment of various cancers as a kinase inhibitor, especially as a Wee1 kinase inhibitor.

BACKGROUND ART

Cells have a checkpoint mechanism in which, when the DNA therein is damaged, the cells temporarily arrest the cell cycle and repair the damaged DNA (Cell Proliferation, Vol. 33, pp. 261-274). In about a half of human cancers, a cancer suppressor gene, p53 is mutated or deleted and the cells thereby have lost the G1 checkpoint function thereof. However, such cancer cells still keep the G2 checkpoint function remaining therein, which is considered to be one factor of lowering the sensitivity of the cells to DNA-active anticancer agents and to radiations.

A Wee1 kinase is a tyrosine kinase that participates in the G2 checkpoint of a cell cycle. Wee1 phosphorylates Cdc2 (Cdk1) tyrosine-15 that participates in the progress to the M phase from the G2 phase in a cell cycle, thereby inactivating Cdc2 and temporarily arresting the cell cycle at the G2 phase (The EMBO Journal, Vol. 12, pp. 75-85). Accordingly, in cancer cells having lost the p53 function therein, it is considered that the G2 checkpoint function of Wee1 is important for repairing the damaged DNA so as to avoid the cell death. Heretofore, it has been reported that the reduction of Wee1 expression by RNA interference or the inhibition of Wee1 by a compound increases the sensitivity of cancer cells to adriamycin, X ray and gamma ray (Cancer Biology & Therapy, Vol. 3, pp. 305-313; or Cancer Research, Vol. 61, pp. 8211-8217). From the above, it is considered that a Wee1 inhibitor may inhibit the G2 checkpoint function of p53-deficient cancer cells, thereby increasing the sensitivity of the cells to DNA-active anticancer agents and to radiations.

As a low-molecular Wee1 kinase inhibitor, for example, compounds described in US Patent Application 2005/0250836 (Patent document 1), WO 2003/091255 (Patent document 2), Cancer Research, Vol. 61, pp. 8211-8217 (Non-patent document 1), Bioorg & Med. Chem. Lett., Vol. 15, pp. 1931-1935 (Non-patent document 2) and the like are known. However, the compounds described in these documents are completely different in structure from the compounds of the invention.

On the other hand, WO 99/61444 (Patent document 3) and WO 2004/041823 (Patent document 4) disclose compounds that partly have a relatively similar skeleton to that of the compounds of the invention. However, these documents do not at all disclose or suggest the compounds of the invention.

DISCLOSURE OF THE INVENTION

An object of the invention is to provide a novel anticancer agent having a kinase inhibitory effect, especially a Wee1 kinase inhibitory effect, and a sensitizer of chemotherapy or radiotherapy for cancer.

As a result of intensive studies, the present inventors have found that compounds represented by the general formula (I) have an excellent kinase inhibitory effect, especially an excellent Wee1 kinase inhibitory effect, and have completed the present invention.

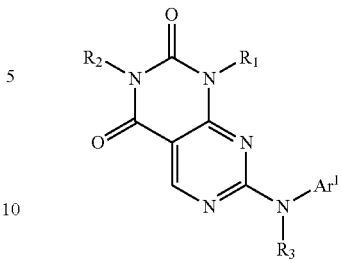

(I)

In the formula, $Ar^1$ denotes an aryl or heteroaryl group which may have a substituent selected from the group consisting of a halogen atom, a C1-C6 alkyl group, a halo-C1-C6 alkyl group, a hydroxy-C1-C6 alkyl group, a C1-C6 alkoxy group, a C2-C7 alkanoyl group, a hydroxy-C1-C6 alkylamino group, a carbamoyl group, a hydroxy-C1-C6 alkylcarbamoyl group, a heteroaryl group which may be substituted with a C1-C6 alkyl group and a group represented by $-Q^1-A^1-Q^2-A^2(R^{1a})R^{1b}$;

$A^1$ denotes a single bond, an oxygen atom or a sulfur atom, or denotes an imino group which may be substituted with a C1-C6 alkyl group;

$A^2$ denotes a nitrogen atom, or denotes a methine group which may be substituted with a hydroxy group, a C1-C6 alkyl group or a hydroxy-C1-C6 alkyl group;

$Q^1$ denotes a single bond, a carbonyl group or a methylene group which may be substituted with a C1-C6 alkyl group;

$Q^2$ denotes a single bond or an ethylene or trimethylene group which may be substituted with a C1-C6 alkyl group;

$R^{1a}$ and $R^{1b}$ each independently denote a hydrogen atom, a C1-C6 alkyl group or a hydroxy-C1-C6 alkyl group, or are combined together to denote a C1-C6 alkylene group, wherein one or two or more methylene groups constituting the C1-C6 alkylene group may be each independently replaced with an oxygen atom, a sulfur atom, a sulfinyl group, a sulfonyl group, a carbonyl group, a vinylene group or a group represented by $-N(R^{1c})-$ or may be substituted with a hydroxy group, a C1-C6 alkyl group or a group represented by $-R^{10c}$;

$R^{1c}$ denotes a hydrogen atom, a formyl group, a C2-C6 alkenyl group or a group represented by $-Q^3-A^3(R^{1d})R^{1e}$;

$R^{10c}$ denotes a group represented by $-Q^{30}-A^{30}(R^{10d})R^{10e}$;

$A^3$ and $A^{30}$ each independently denote a nitrogen atom, or denote a methine group which may be substituted with a hydroxy group, a C1-C6 alkyl group or a hydroxy-C1-C6 alkyl group;

$Q^3$ and $Q^{30}$ each independently denote a single bond or a C1-C6 alkylene group, wherein one or two or more methylene groups constituting the C1-C6 alkylene group may be each independently replaced with an oxygen atom, a sulfur atom, a carbonyl group, a sulfinyl group or a sulfonyl group, or may be substituted with a halogen atom, a cyano group, a hydroxy group or a C1-C6 alkyl group;

$R^{1d}$ and $R^{1e}$ each independently denote a hydrogen atom, a halogen atom, a cyano group, a hydroxy group, a C1-C6 alkyl group or a hydroxy-C1-C6 alkyl group, or are combined together to denote a C1-C6 alkylene group, wherein one or two or more methylene groups constituting the C1-C6 alkylene group may be each independently replaced with an oxygen atom, a sulfur atom, a sulfinyl group, a sulfonyl group, a carbonyl group, a vinylene group or a group represented by $-N(R^{1f})-$ or may be substituted with a hydroxy group or a C1-C6 alkyl group;

$R^{1f}$ and $R^{10f}$ each independently denote a hydrogen atom, a C1-C6 alkyl group, a halo-C1-C6 alkyl group, a C2-C6 alkenyl group or a C2-C7 alkanoyl group;

$R^{10d}$ and $R^{10e}$ each independently denote a hydrogen atom, a halogen atom, a cyano group, a hydroxy group, a C1-C6 alkyl group or a hydroxy-C1-C6 alkyl group, or are combined together to denote a C1-C6 alkylene group, wherein one or two or more methylene groups constituting the C1-C6 alkylene group may be each independently replaced with an oxygen atom, a sulfur atom, a sulfinyl group, a sulfonyl group, a carbonyl group, a vinylene group or a group represented by —N($R^{10f}$)— or may be substituted with a hydroxy group or a C1-C6 alkyl group;

$R^1$ denotes a hydrogen atom, or denotes a C1-C6 alkyl group which may have a substituent selected from the group consisting of a halogen atom, a hydroxy group, a cyano group, a C1-C6 alkoxy group, a C3-C6 cycloalkyl group, a C2-C7 alkanoyl group and a C1-C6 alkylsulfonyl group, or denotes an aryl, aralkyl or heteroaryl group which may have a substituent selected from the group consisting of a halogen atom, a hydroxy group, a cyano group, an amino group, a C1-C6 alkyl group, a C1-C6 alkoxy group, a halo-C1-C6 alkyl group and a hydroxy-C1-C6 alkyl group;

$R^2$ denotes an unsubstituted aralkyl group, or denotes a group represented by the formula (a):

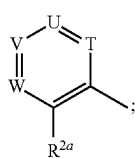

(a)

$R^{2a}$ denotes a halogen atom, a hydroxy group, a cyano group, an amino group, a nitro group, a carbamoyl group, a C1-C6 alkyl group, a C1-C6 alkylsulfonyl group, a C1-C6 alkoxy group, a halo-C1-C6 alkyl group, a hydroxy-C1-C6 alkyl group or a C1-C6 alkoxy-C1-C6 alkyl group;

T, U, V and W each independently denote a methine group which may have a substituent selected from the group consisting of a halogen atom, a hydroxy group, a cyano group, an amino group, a nitro group, a carbamoyl group, a C1-C6 alkyl group, a C1-C6 alkylsulfonyl group, a C1-C6 alkoxy group, a halo-C1-C6 alkyl group, a hydroxy-C1-C6 alkyl group and a C1-C6 alkoxy-C1-C6 alkyl group or a nitrogen atom, at least two of which denote the methine group; and $R^3$ denotes a hydrogen atom or a C1-C6 alkyl group.

The compounds (I) of the invention have a kinase inhibitory effect, especially a Wee1 kinase inhibitory effect, and are therefore useful as a therapeutic agent for various cancers such as brain tumor, head and neck cancer, esophageal cancer, thyroid cancer, small cell cancer, non-small cell cancer, breast cancer, lung cancer, stomach cancer, gallbladder and bile duct cancer, liver cancer, pancreatic cancer, colon cancer, rectal cancer, ovarian cancer, chorioepithelioma, endometrial cancer, cervical cancer, renal pelvic and ureteral cancer, bladder cancer, prostate cancer, penile cancer, testicular cancer, embryonal carcinoma, Wilms' tumor, skin cancer, malignant melanoma, neuroblastoma, osteosarcoma, Ewing's tumor, soft tissue sarcoma, acute leukemia, chronic lymphocytic leukemia, chronic myeloid leukemia and Hodgkin's lymphoma, or a sensitizer of chemotherapy or radiotherapy for these cancers.

In particular, the compounds (I) of the invention are useful as a therapeutic agent for, for example, breast cancer, lung cancer, pancreatic cancer, colon cancer, ovarian cancer, acute leukemia, chronic lymphocytic leukemia, chronic myeloid leukemia, Hodgkin's lymphoma and the like, or a sensitizer of chemotherapy or radiotherapy for these cancers.

The invention relates to the compounds represented by the general formula (I), or pharmaceutically acceptable salts or N-oxide derivatives thereof, as well as to methods for producing the same and use thereof.

Hereinafter, the meanings of the terms to be used in this description will be described and the invention will be illustrated in more detail.

The "halogen atom" means a fluorine atom, a chlorine atom, a bromine atom or an iodine atom.

The "C1-C6 alkyl group" means a linear or branched alkyl group having 1 to 6 carbon atoms, and examples thereof include a methyl group, an ethyl group, a propyl group, an isopropyl group, a butyl group, an isobutyl group, a sec-butyl group, a tert-butyl group, a pentyl group, an isopentyl group, a hexyl group and an isohexyl group.

The "C3-C6 cycloalkyl group" means a cycloalkyl group having 3 to 6 carbon atoms, and examples thereof include a cyclopropyl group, a cyclobutyl group, a cyclopentyl group and a cyclohexyl group.

The "halo-C1-C6 alkyl group" means the above-mentioned C1-C6 alkyl group substituted with one or two or more, preferably one to three of the above-mentioned halogen atoms which are the same or different at any substitutable positions, and examples thereof include a fluoromethyl group, a difluoromethyl group, a trifluoromethyl group, a 2-fluoroethyl group, a 1,2-difluoroethyl group, a chloromethyl group, a 2-chloroethyl group, a 1,2-dichloroethyl group, a bromomethyl group and an iodomethyl group.

The "C1-C6 alkoxy group" means a linear or branched alkoxy group having 1 to 6 carbon atoms, and examples thereof include a methoxy group, an ethoxy group, a propoxy group, an isopropoxy group, a butoxy group, a sec-butoxy group, an isobutoxy group, a tert-butoxy group, a pentyloxy group, an isopentyloxy group, a hexyloxy group and an isohexyloxy group.

The "C1-C6 alkoxy group-C1-C6 alkyl group" means the above-mentioned C1-C6 alkyl group substituted with one or two or more, preferably one of the above-mentioned C1-C6 alkoxy groups at any substitutable position, and examples thereof include a methoxymethyl group, an ethoxymethyl group and a 2-methoxyethyl group.

The "C2-C7 alkanoyl group" means an alkanoyl group having the above-mentioned C1-C6 alkyl group, that is, an alkanoyl group having 2 to 7 carbon atoms, and examples thereof include an acetyl group, a propionyl group, a butyryl group, an isobutyryl group, a valeryl group, an isovaleryl group and a pivaloyl group.

Examples of the "aryl group" include a phenyl group and a naphthyl group.

The "aralkyl group" means the above-mentioned C1-C6 alkyl group substituted with one or two or more, preferably one of the above-mentioned aryl groups at any substitutable position, and examples thereof include a benzyl group, a 1-phenylethyl group, a phenethyl group, a 1-naphthylmethyl group and a 2-naphthylmethyl group.

The "heteroaryl group" means a 5- or 6-membered monocyclic heteroaryl group having one or two or more, preferably one to three heteroatoms which are the same or different and are selected from the group consisting of an oxygen atom, a nitrogen atom and a sulfur atom, or a condensed cyclic heteroaryl group formed by condensation of the monocyclic heteroaryl group with the above-mentioned aryl group, or condensation of the same or different monocyclic heteroaryl groups with each other. Examples thereof include a pyrrolyl group, a furyl group, a thienyl group, an imidazolyl group, a pyrazolyl group, a thiazolyl group, an isothiazolyl group, an oxazolyl group, an isoxazolyl group, a triazolyl group, a tetrazolyl group, an oxadiazolyl group, a 1,2,3-thiadiazolyl group, a 1,2,4-thiadiazolyl group, a 1,3,4-thiadiazolyl group, a pyridyl group, a pyrazinyl group, a pyrimidinyl group, a pyridazinyl group, a 1,2,4-triazinyl group, a 1,3,5-triazinyl group, an indolyl group, a benzofuranyl group, a benzothienyl group, a benzimidazolyl group, a benzoxazolyl group, a benzisoxazolyl group, a benzothiazolyl group, a benzisothiazolyl group, a indazolyl group, a purinyl group, a quinolyl group, an isoquinolyl group, a phthalazinyl group, a naphthyridinyl group, a quinoxalinyl group, a quinazolinyl group, a cinnolinyl group, a pteridinyl group and a pyrido[3,2-b]pyridyl group.

The "C1-C6 alkylsulfonyl group" means a linear or branched alkylsulfonyl group having 1 to 6 carbon atoms, and examples thereof include a methylsulfonyl group, an ethylsulfonyl group, a propylsulfonyl group, an isopropylsulfonyl group, a butylsulfonyl group, a sec-butylsulfonyl group, an isobutylsulfonyl group, a tert-butylsulfonyl group, a pentylsulfonyl group, an isopentylsulfonyl group, a hexylsulfonyl group and an isohexylsulfonyl group.

The "hydroxy-C1-C6 alkyl group" means the above-mentioned C1-C6 alkyl group substituted with one or two or more, preferably one or two hydroxy groups at any substitutable positions, and examples thereof include a hydroxymethyl group, a 2-hydroxyethyl group, a 1-hydroxy-1-methylethyl group, a 1,2-dihydroxyethyl group and a 3-hydroxypropyl group.

The "hydroxy-C1-C6 alkylamino group" means an amino group monosubstituted with the above-mentioned hydroxy-C1-C6 alkyl group, and examples thereof include a hydroxymethylamino group, a 2-hydroxyethylamino group, a 1-hydroxy-1-methylethylamino group, a 1,2-dihydroxyethylamino group and a 3-hydroxypropylamino group.

The "hydroxy-C1-C6 alkylcarbamoyl group" means a carbamoyl group monosubstituted with the above-mentioned hydroxy-C1-C6 alkyl group, and examples thereof include a hydroxymethylcarbamoyl group, a 2-hydroxyethylcarbamoyl group, a 1-hydroxy-1-methylethylcarbamoyl group, a 1,2-dihydroxyethylcarbamoyl group and a 3-hydroxypropylcarbamoyl group.

The "C1-C6 alkylene group" means an alkylene group having 1 to 6 carbon atoms, and examples thereof include a methylene group, an ethylene group, a trimethylene group, a tetramethylene group, a pentamethylene group and a hexamethylene group.

The "C2-C6 alkenyl group" means a linear or branched alkenyl group having 2 to 6 carbon atoms, and examples thereof include a vinyl group, a 1-propenyl group, an allyl group, an isopropenyl group, a 3-butenyl group, a 2-butenyl group, a 1-butenyl group, a 1-methyl-2-propenyl group, a 1-methyl-1-propenyl group, a 1-ethyl-1-ethenyl group, a 2-methyl-2-propenyl group, a 2-methyl-1-propenyl group, a 3-methyl-2-butenyl group and a 4-pentenyl group.

The "pharmaceutically acceptable salt" of the compound of the invention means a commonly used pharmaceutically acceptable salt. For example, when the compound has a carboxyl group or a hydroxy group, a base addition salt at the carboxyl group or hydroxy group; when the compound has an amino group, a basic nitrogen-containing heterocyclic group or another heterocyclic group, an acid addition salt at the amino group, basic nitrogen-containing heterocyclic group or heterocyclic group can be exemplified.

Examples of the base addition salt include alkali metal salts such as sodium salts and potassium salts; alkaline earth metal salts such as calcium salts and magnesium salts; ammonium salts; and organic amine salts such as trimethylamine salts, triethylamine salts, dicyclohexylamine salts, ethanolamine salts, diethanolamine salts, triethanolamine salts, procaine salts and N,N'-dibenzylethylenediamine salts.

Examples of the acid addition salt include inorganic acid salts such as hydrochlorides, sulfates, nitrates, phosphates and perchlorates; organic acid salts such as maleates, fumarates, tartrates, citrates, ascorbates and trifluoroacetates; and sulfonates such as methanesulfonates, isethionates, benzenesulfonates and p-toluenesulfonates.

The "N-oxide derivative" of the compound of the invention means a compound in which any one or two or more nitrogen atoms capable of forming an N-oxide in the compound are oxidized to form an N-oxide and which is pharmaceutically acceptable. For example, a compound in which a nitrogen atom in the ring of a dihydropyrimido[4,5-d]pyrimidine skeleton of the compound of the invention is oxidized and the like can be exemplified.

For illustrating the compounds of the invention more specifically, the respective symbols to be used in this description and the like will be described in more detail with reference to preferred specific examples thereof.

$Ar^1$ denotes an aryl or heteroaryl group which may have a substituent selected from the group consisting of a halogen atom, a C1-C6 alkyl group, a halo-C1-C6 alkyl group, a hydroxy-C1-C6 alkyl group, a C1-C6 alkoxy group, a C2-C7 alkanoyl group, a hydroxy-C1-C6 alkylamino group, a carbamoyl group, a hydroxy-C1-C6 alkylcarbamoyl group, a heteroaryl group which may be substituted with a C1-C6 alkyl group and a group represented by $-Q^1-A^1-Q^2-A^2(R^{1a})R^{1b}$.

The "aryl or heteroaryl group which may have a substituent selected from the group consisting of a halogen atom, a C1-C6 alkyl group, a halo-C1-C6 alkyl group, a hydroxy-C1-C6 alkyl group, a C1-C6 alkoxy group, a C2-C7 alkanoyl group, a hydroxy-C1-C6 alkylamino group, a carbamoyl group, a hydroxy-C1-C6 alkylcarbamoyl group, a heteroaryl group which may be substituted with a C1-C6 alkyl group and a group represented by $-Q^1-A^1-Q^2-A^2(R^{1a})R^{1b}$" denoted by $Ar^1$ means the above-mentioned aryl or heteroaryl group which is unsubstituted or has a substituent at any substitutable position. As the substituent, one or two or more, preferably one or two groups which are the same or different can be selected from the group consisting of a halogen atom, a C1-C6 alkyl group, a halo-C1-C6 alkyl group, a hydroxy-C1-C6 alkyl group, a C1-C6 alkoxy group, a C2-C7 alkanoyl group, a hydroxy-C1-C6 alkylamino group, a carbamoyl group, a hydroxy-C1-C6 alkylcarbamoyl group, a heteroaryl group which may be substituted with a C1-C6 alkyl group and a group represented by $-Q^1-A^1-Q^2-A^2(R^{1a})R^{1b}$.

As the halogen atom as the substituent, for example, a fluorine atom, a chlorine atom or the like is preferred.

As the C1-C6 alkyl group as the substituent, for example, a methyl group, an ethyl group or the like is preferred.

As the halo-C1-C6 alkyl group as the substituent, for example, a fluoromethyl group, a difluoromethyl group, a trifluoromethyl group or the like is preferred.

As the hydroxy-C1-C6 alkyl group as the substituent, for example, a hydroxymethyl group, a 2-hydroxyethyl group or the like is preferred.

As the C1-C6 alkoxy group as the substituent, for example, a methoxy group, an ethoxy group or the like is preferred.

As the C2-C7 alkanoyl group as the substituent, for example, an acetyl group or the like is preferred.

As the hydroxy-C1-C6 alkylamino group as the substituent, for example, a hydroxymethylamino group, a 2-hydroxyethylamino group or the like is preferred.

As the hydroxy-C1-C6 alkylcarbamoyl group as the substituent, for example, a hydroxymethylcarbamoyl group, a 2-hydroxyethylcarbamoyl group or the like is preferred.

The "heteroaryl group which may be substituted with a C1-C6 alkyl group" as the substituent means the above-mentioned heteroaryl group which is unsubstituted or has one or two or more, preferably one or two of the above-mentioned C1-C6 alkyl groups which are the same or different at any substitutable positions, and for example, a 4-methyl-1-imidazolyl group, a 1-methyl-4-pyrazolyl group or the like is preferred.

In the group represented by -Q$^1$-A$^1$-Q$^2$-A$^2$(R$^{1a}$)R$^{1b}$ as the substituent, A$^1$ denotes a single bond, an oxygen atom or a sulfur atom, or denotes an imino group which may be substituted with a C1-C6 alkyl group; A$^2$ denotes a nitrogen atom, or denotes a methine group which may be substituted with a hydroxy group, a C1-C6 alkyl group or a hydroxy-C1-C6 alkyl group; Q$^1$ denotes a single bond, a carbonyl group or a methylene group which may be substituted with a C1-C6 alkyl group; Q$^2$ denotes a single bond or an ethylene or trimethylene group which may be substituted with a C1-C6 alkyl group; R$^{1a}$ and R$^{1b}$ each independently denote a hydrogen atom, a C1-C6 alkyl group or a hydroxy-C1-C6 alkyl group, or are combined together to denote a C1-C6 alkylene group, wherein one or two or more methylene groups constituting the C1-C6 alkylene group may be each independently replaced with an oxygen atom, a sulfur atom, a sulfinyl group, a sulfonyl group, a carbonyl group, a vinylene group or a group represented by —N(R$^{1c}$)— or may be substituted with a hydroxy group, a C1-C6 alkyl group or a group represented by —R$^{10c}$.

The "imino group which may be substituted with a C1-C6 alkyl group" denoted by A$^1$ means an unsubstituted imino group or an imino group substituted with the above-mentioned C1-C6 alkyl group. As the C1-C6 alkyl group as the substituent, for example, a methyl group, an ethyl group or the like is preferred.

The "methine group which may be substituted with a hydroxy group, a C1-C6 alkyl group or a hydroxy-C1-C6 alkyl group" denoted by A$^2$ means an unsubstituted methine group or a methine group having a substituent selected from the group consisting of a hydroxy group, a C1-C6 alkyl group and a hydroxy-C1-C6 alkyl group.

As the C1-C6 alkyl group as the substituent, for example, a methyl group, an ethyl group or the like is preferred.

As the hydroxy-C1-C6 alkyl group as the substituent, for example, a hydroxymethyl group, a 2-hydroxyethyl group or the like is preferred.

As the substituent, for example, a hydroxy group or the like is preferred.

The "methylene group which may be substituted with a C1-C6 alkyl group" denoted by Q$^1$ means an unsubstituted methylene group or a methylene group substituted with one or two of the above-mentioned C1-C6 alkyl groups which are the same or different.

As the C1-C6 alkyl group as the substituent, for example, a methyl group or the like is preferred.

The "ethylene or trimethylene group which may be substituted with a C1-C6 alkyl group" denoted by Q$^2$ means an unsubstituted ethylene or trimethylene group, or an ethylene or trimethylene group substituted with one or two or more, preferably one or two of the above-mentioned C1-C6 alkyl groups which are the same or different at any substitutable positions.

As the C1-C6 alkyl group as the substituent, for example, a methyl group or the like is preferred.

As the "C1-C6 alkyl group" denoted by R$^{1a}$ or R$^{1b}$, for example, a methyl group, an ethyl group, a propyl group, an isopropyl group or the like is preferred.

As the "hydroxy-C1-C6 alkyl group" denoted by R$^{1a}$ or R$^{1b}$, for example, a hydroxymethyl group, a 2-hydroxyethyl group or the like is preferred.

As the C1-C6 alkylene group formed by combining R$^{1a}$ and R$^{1b}$ together, for example, a trimethylene group, a tetramethylene group, a pentamethylene group, a hexamethylene group or the like is preferred. When "A$^2$" to which R$^{1a}$ and R$^{1b}$ are bound is a nitrogen atom, these denote, together with the nitrogen atom, a 1-azetidinyl group, a 1-pyrrolidinyl group, a piperidino group, a perhydro-1H-azepin-1-yl group or the like, respectively; and when "A$^2$" is a methine group, these denote, together with the methine group, a cyclobutyl group, a cyclopentyl group, a cyclohexyl group, a cycloheptyl group or the like respectively. Among these, a 1-pyrrolidinyl group, a piperidino group, a perhydro-1H-azepin-1-yl group, a cyclobutyl group, a cyclohexyl group, a 1-cyclohexenyl group or the like is more preferred.

One or two or more methylene groups constituting the above-mentioned C1-C6 alkylene group may be each independently replaced with an oxygen atom, a sulfur atom, a sulfinyl group, a sulfonyl group, a carbonyl group, a vinylene group or a group represented by —N(R$^{1c}$)—, and as such a group, for example, a group selected from groups represented by the formula (aa1) can be exemplified.

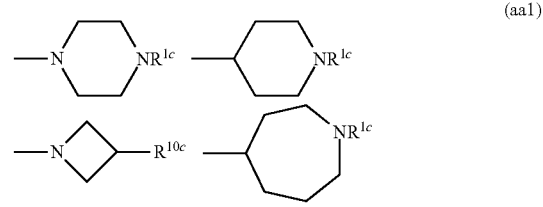

(aa1)

Among these, a group selected from groups represented by the formula (aa1') is preferred.

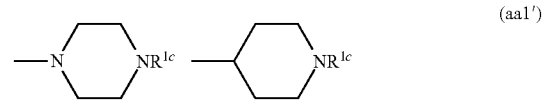

(aa1')

Here, the C1-C6 alkylene group formed by combining R$^{1a}$ and R$^{1b}$ together or the group represented by the formula (aa1) or the formula (aa1') may be substituted with a hydroxy group, a C1-C6 alkyl group or a group represented by —R$^{10c}$ at any substitutable position in the group.

In the group represented by —N(R$^{1c}$)—, R$^{1c}$ denotes a hydrogen atom, a formyl group, a C2-C6 alkenyl group or a group represented by -Q$^3$-A$^3$(R$^{1d}$)R$^{1e}$.

As the C2-C6 alkenyl group denoted by R$^{1c}$, for example, a vinyl group, an allyl group or the like is preferred.

In the group represented by -Q$^3$-A$^3$(R$^{1d}$)R$^{1e}$ denoted by R$^{1c}$, A$^3$ denotes a nitrogen atom, or denotes a methine group which may be substituted with a hydroxy group, a C1-C6 alkyl group or a hydroxy-C1-C6 alkyl group; Q$^3$ denotes a single bond or a C1-C6 alkylene group, wherein one or two or more methylene groups constituting the C1-C6 alkylene group may be each independently replaced with an oxygen atom, a sulfur atom, a carbonyl group, a sulfinyl group or a sulfonyl group, or may be substituted with a halogen atom, a cyano group, a hydroxy group or a C1-C6 alkyl group; $R^{1d}$ and $R^{1e}$ each independently denote a hydrogen atom, a halogen atom, a cyano group, a hydroxy group, a C1-C6 alkyl group or a hydroxy-C1-C6 alkyl group, or are combined together to denote a C1-C6 alkylene group, wherein one or two or more methylene groups constituting the C1-C6 alkylene group may be each independently replaced with an oxygen atom, a sulfur atom, a sulfinyl group, a sulfonyl group, a carbonyl group, a vinylene group or a group represented by —N($R^{1f}$)— or may be substituted with a hydroxy group or a C1-C6 alkyl group; and $R^{1f}$ denotes a hydrogen atom, a C1-C6 alkyl group, a halo-C1-C6 alkyl group, a C2-C6 alkenyl group or a C2-C7 alkanoyl group.

The "methine group which may be substituted with a hydroxy group, a C1-C6 alkyl group or a hydroxy-C1-C6 alkyl group" denoted by $A^3$ means an unsubstituted methine group or a methine group having a substituent selected from the group consisting of a hydroxy group, a C1-C6 alkyl group and a hydroxy-C1-C6 alkyl group.

As the C1-C6 alkyl group as the substituent, for example, a methyl group, an ethyl group or the like is preferred.

As the hydroxy-C1-C6 alkyl group as the substituent, for example, a hydroxymethyl group, a 2-hydroxyethyl group, a 2-hydroxypropyl group, a 2-methyl-2-hydroxypropyl group or the like is preferred.

As the substituent, for example, a hydroxy group, a C1-C6 alkyl group or the like is preferred.

As the C1-C6 alkylene group denoted by $Q^3$, for example, a methylene group, an ethylene group, a trimethylene group or the like is preferred.

One or two or more methylene groups constituting the C1-C6 alkylene group denoted by $Q^3$ may be each independently replaced with an oxygen atom, a sulfur atom, a carbonyl group, a sulfinyl group or a sulfonyl group, and as such a group, for example, a group selected from groups represented by the formula (aa2) is preferred.

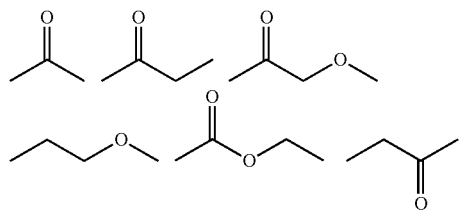

(aa2)

Here, the C1-C6 alkylene group or the group represented by the formula (aa2) denoted by $Q^3$ may be substituted with a halogen atom, a cyano group, a hydroxy group or a C1-C6 alkyl group at any substitutable position in the group.

As the "halogen atom" denoted by $R^{1d}$ or $R^{1e}$, for example, a fluorine atom, a chlorine atom or the like is preferred.

As the "C1-C6 alkyl group" denoted by $R^{1d}$ or $R^{1e}$, for example, a methyl group, an ethyl group or the like is preferred.

As the "hydroxy-C1-C6 alkyl group" denoted by $R^{1d}$ or $R^{1e}$, for example, a hydroxymethyl group, a 2-hydroxyethyl group or the like is preferred.

As the C1-C6 alkylene group formed by combining $R^{1d}$ and $R^{1e}$ together, for example, an ethylene group, a trimethylene group, a tetramethylene group or the like is preferred. When "$A^3$" to which $R^{1d}$ and $R^{1e}$ are bound is a nitrogen atom, these denote, together with the nitrogen atom, a 1-aziridinyl group, a 1-azetidinyl group, a 1-pyrrolidinyl group or the like, respectively; and when "$A^3$" is a methine group, these denote, together with the methine group, a cyclopropyl group, a cyclobutyl group, a cyclopentyl group or the like, respectively. Among these, a cyclopropyl group, a cyclobutyl group, a cyclopentyl group or the like is more preferred.

One or two or more methylene groups constituting the above-mentioned C1-C6 alkylene group may be each independently replaced with an oxygen atom, a sulfur atom, a sulfinyl group, a sulfonyl group, a carbonyl group, a vinylene group or a group represented by —N($R^{1f}$)—, and as such a group, for example, a group represented by the formula (aa3) is preferred.

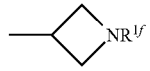

(aa3)

Here, the C1-C6 alkylene group or the group represented by the formula (aa3) denoted by $R^{1d}$ or $R^{1e}$ may be substituted with a hydroxy group or a C1-C6 alkyl group at any substitutable position in the group.

In the group represented by —N($R^{1f}$)—, $R^{1f}$ each independently denotes a hydrogen atom, a C1-C6 alkyl group, a halo-C1-C6 alkyl group, a C2-C6 alkenyl group or a C2-C7 alkanoyl group.

As the C1-C6 alkyl group denoted by $R^{1f}$, for example, a methyl group, an ethyl group or the like is preferred.

As the halo-C1-C6 alkyl group denoted by $R^{1f}$, for example, a fluoromethyl group, a difluoromethyl group or the like is preferred.

As the C2-C6 alkenyl group denoted by $R^{1f}$, for example, an allyl group or the like is preferred.

As the C2-C7 alkanoyl group denoted by $R^{1f}$, for example, an acetyl group or the like is preferred.

As $R^{1f}$, a C2-C7 alkanoyl group is preferred.

As a preferred embodiment of the group represented by -$Q^3$-$A^3$($R^{1d}$)$R^{1e}$, for example, the following cases can be exemplified:

(i) $A^3$ is a methine group which may be substituted with a hydroxy group or a C1-C6 alkyl group, $Q^3$ is a single bond, and $R^{1d}$ and $R^{1e}$ are each independently a hydrogen atom or a C1-C6 alkyl group;

(ii) $A^3$ is a methine group, $Q^3$ is a single bond or a C1-C6 alkylene group, and $R^{1d}$ and $R^{1e}$ are combined together to denote a C1-C6 alkylene group, wherein one methylene group constituting the C1-C6 alkylene group may be replaced with a group represented by —N($R^{1f}$)—;

(iii) $A^3$ is a methine group which may be substituted with a hydroxy group or a C1-C6 alkyl group, $Q^3$ is a C1-C6 alkylene group, wherein one or two methylene groups constituting the C1-C6 alkylene group may be each independently replaced with an oxygen atom, a carbonyl group or a sulfonyl group, or may be substituted with a hydroxy group, and $R^{1d}$ and $R^{1e}$ are each independently a hydrogen atom, a halogen atom, a cyano group or a C1-C6 alkyl group; and (iv) $A^3$ is a nitrogen atom, $Q^3$ is a C1-C6 alkylene group, wherein one methylene group constituting the C1-C6 alkylene group is replaced with a carbonyl group, and $R^{1d}$ and $R^{1e}$ are each independently a hydrogen atom or a C1-C6 alkyl group; and as a more preferred embodiment, the case of the above (i) and the like can be exemplified.

More specific examples of the group represented by -$Q^3$-$A^3$($R^{1d}$)$R^{1e}$ include a methyl group, an acetyl group, a 2-hydroxy-2-methylpropyl group, a 2-dimethylaminoacetyl group, an isopropyl group, a 2-hydroxy-2-methylpropionyl group, a cyclopropyl group, a 2-methoxyethyl group, a hydroxyacetyl group, a difluoroacetyl group, a methoxyacetyl group, a tert-butoxycarbonyl group, a dimethylcarbamoylmethyl group, a 2-methoxy-2-methylpropionyl group, a 2-hydroxyethoxy group and an ethoxycarbonyl group. Among these, preferred is a methyl group, an acetyl group, a 2-hydroxy-2-methylpropyl group, a 2-dimethylaminoacetyl group, a difluoroacetyl group, a methoxyacetyl group, a 2-methoxy-2-methylpropionyl group or the like, and more preferred is a methyl group, an acetyl group, a 2-hydroxy-2-methylpropyl group or the like.

As $R^{1c}$, preferred is a hydrogen atom, a formyl group or a group represented by $-Q^3-A^3(R^{1d})R^{1e}$, and more preferred is a group represented by $-Q^3-A^3(R^{1d})R^{1e}$.

$R^{10c}$ denotes a group represented by $-Q^{30}-A^{30}(R^{10d})R^{10e}$, wherein $A^{30}$ denotes a nitrogen atom, or denotes a methine group which may be substituted with a hydroxy group, a C1-C6 alkyl group or a hydroxy-C1-C6 alkyl group; $Q^{30}$ denotes a single bond or a C1-C6 alkylene group, wherein one or two or more methylene groups constituting the C1-C6 alkylene group may be each independently replaced with an oxygen atom, a sulfur atom, a carbonyl group, a sulfinyl group or a sulfonyl group, or may be substituted with a halogen atom, a cyano group, a hydroxy group or a C1-C6 alkyl group; $R^{10d}$ and $R^{10e}$ each independently denote a hydrogen atom, a halogen atom, a cyano group, a hydroxy group, a C1-C6 alkyl group or a hydroxy-C1-C6 alkyl group, or are combined together to denote a C1-C6 alkylene group, wherein one or two or more methylene groups constituting the C1-C6 alkylene group may be each independently replaced with an oxygen atom, a sulfur atom, a sulfinyl group, a sulfonyl group, a carbonyl group, a vinylene group or a group represented by $—N(R^{10f})—$ or may be substituted with a hydroxy group or a C1-C6 alkyl group; and $R^{10f}$ denotes a hydrogen atom, a C1-C6 alkyl group, a halo-C1-C6 alkyl group, a C2-C6 alkenyl group or a C2-C7 alkanoyl group.

The "methine group which may be substituted with a hydroxy group, a C1-C6 alkyl group or a hydroxy-C1-C6 alkyl group" denoted by $A^{30}$ means an unsubstituted methine group or a methine group having a substituent selected from the group consisting of a hydroxy group, a C1-C6 alkyl group and a hydroxy-C1-C6 alkyl group.

As the C1-C6 alkyl group as the substituent, for example, a methyl group, an ethyl group or the like is preferred.

As the hydroxy-C1-C6 alkyl group as the substituent, for example, a hydroxymethyl group, a 2-hydroxyethyl group, a 2-hydroxypropyl group, a 2-methyl-2-hydroxypropyl group or the like is preferred.

As the substituent, for example, a hydroxy group, a C1-C6 alkyl group or the like is preferred.

As the C1-C6 alkylene group denoted by $Q^{30}$, for example, a methylene group, an ethylene group, a trimethylene group or the like is preferred.

One or two or more methylene groups constituting the C1-C6 alkylene group denoted by $Q^{30}$ may be each independently replaced with an oxygen atom, a sulfur atom, a carbonyl group, a sulfinyl group or a sulfonyl group, and as such a group, for example, a group selected from groups represented by the formula (aa2') is preferred.

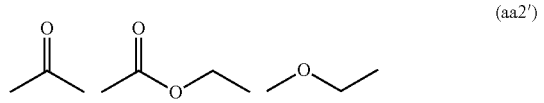
(aa2')

Here, the C1-C6 alkylene group or the group represented by the formula (aa2') denoted by $Q^{30}$ may be substituted with a halogen atom, a cyano group, a hydroxy group or a C1-C6 alkyl group at any substitutable position in the group.

As the "halogen atom" denoted by $R^{10d}$ or $R^{10e}$, for example, a fluorine atom, a chlorine atom or the like is preferred.

As the "C1-C6 alkyl group" denoted by $R^{10d}$ or $R^{10e}$, for example, a methyl group, an ethyl group or the like is preferred.

As the "hydroxy-C1-C6 alkyl group" denoted by $R^{10d}$ or $R^{10e}$, for example, a hydroxymethyl group, a 2-hydroxyethyl group or the like is preferred.

As the C1-C6 alkylene group formed by combining $R^{10d}$ and $R^{10e}$ together, for example, an ethylene group, a trimethylene group, a tetramethylene group or the like is preferred. When "$A^{30}$" to which $R^{10d}$ and $R^{10e}$ are bound is a nitrogen atom, these denote, together with the nitrogen atom, a 1-aziridinyl group, a 1-azetidinyl group, a 1-pyrrolidinyl group or the like, respectively; and when "$A^{30}$" is a methine group, these denote, together with the methine group, a cyclopropyl group, a cyclobutyl group, a cyclopentyl group or the like, respectively. Among these, a cyclopropyl group, a cyclobutyl group, a cyclopentyl group or the like is more preferred.

One or two or more methylene groups constituting the above-mentioned C1-C6 alkylene group may be each independently replaced with an oxygen atom, a sulfur atom, a sulfinyl group, a sulfonyl group, a carbonyl group, a vinylene group or a group represented by $—N(R^{10f})—$, and as such a group, for example, a group represented by the formula (aa3') or the like is preferred.

(aa3')

Here, the C1-C6 alkylene group or the group represented by the formula (aa3') denoted by $R^{10d}$ or $R^{10e}$ may be substituted with a hydroxy group or a C1-C6 alkyl group at any substitutable position in the group.

In the group represented by $—N(R^{10f})—$, $R^{10f}$ each independently denotes a hydrogen atom, a C1-C6 alkyl group, a halo-C1-C6 alkyl group, a C2-C6 alkenyl group or a C2-C7 alkanoyl group.

As the C1-C6 alkyl group denoted by $R^{10f}$, for example, a methyl group, an ethyl group or the like is preferred.

As the halo-C1-C6 alkyl group denoted by $R^{10f}$, for example, a fluoromethyl group, a difluoromethyl group or the like is preferred.

As the C2-C6 alkenyl group denoted by $R^{10f}$, for example, an allyl group or the like is preferred.

As the C2-C7 alkanoyl group denoted by $R^{10f}$, for example, an acetyl group or the like is preferred.

As $R^{10f}$, preferred is a hydrogen atom or a methyl group, and more preferred is a methyl group.

More specific examples of the group represented by $-Q^{30}-A^{30}(R^{10d})R^{10e}$ include a 2-hydroxy-2-propynyl group, an ethoxycarbonyl group and a 2-hydroxyethoxy group, and among these, a 2-hydroxy-2-propynyl group is preferred.

As a preferred embodiment of the group represented by $-Q^1-A^1-Q^2-A^2(R^{1a})R^{1b}$, for example, the following cases can be exemplified:

(i) $A^1$, $Q^1$ and $Q^2$ are a single bond, $A^2$ is a nitrogen atom, and $R^{1a}$ and $R^{1b}$ are combined together to denote a C1-C6 alkylene group, wherein one or two methylene groups constituting the C1-C6 alkylene group may be each independently replaced with an oxygen atom, a sulfonyl group, a carbonyl group or a group represented by —N($R^{1c}$)— (wherein, $R^{1c}$ has the same meaning as the definition in claim 1) or may be substituted with a hydroxy group;

(ii) $A^1$, $Q^1$ and $Q^2$ are a single bond, $A^2$ is a nitrogen atom, and $R^{1a}$ and $R^{1b}$ are combined together to denote a C1-C6 alkylene group, wherein one or two methylene groups constituting the C1-C6 alkylene group may be each independently substituted with a hydroxy group, a C1-C6 alkyl group or —$R^{10c}$;

(iii) $A^1$, $Q^1$ and $Q^2$ are a single bond, $A^2$ is a methine group which may be substituted with a hydroxy group, and $R^{1a}$ and $R^{1b}$ are combined together to denote a C1-C6 alkylene group, wherein one methylene group constituting the C1-C6 alkylene group is replaced with a group represented by —N($R^{1c}$)—;

(iv) $A^1$ is an oxygen atom, $A^2$ is a methine group, $Q^1$ and $Q^2$ are a single bond, and $R^{1a}$ and $R^{1b}$ are combined together to denote a C1-C6 alkylene group, wherein one methylene group constituting the C1-C6 alkylene group is replaced with a group represented by —N($R^{1c}$)—;

(v) $A^1$ is an oxygen atom, $A^2$ is a nitrogen atom, $Q^1$ is a single bond, $Q^2$ is an ethylene group or a trimethylene group, and $R^{1a}$ and $R^{1b}$ are each independently a C1-C6 alkyl group; and (vi) $A^1$ and $Q^2$ are a single bond, $A^2$ is a nitrogen atom, $Q^1$ is a methylene group, and $R^{1a}$ and $R^{1b}$ are combined together to denote a C1-C6 alkylene group, wherein one methylene group constituting the C1-C6 alkylene group may be replaced with a group represented by —N($R^{1c}$)—; and as a more preferred embodiment, the case of the above (i) and the like can be exemplified.

More specific examples of the group represented by -$Q^1$-$A^1$-$Q^2$-$A^2$($R^{1a}$)$R^{1b}$ include a 1-piperazinyl group, a 4-methyl-1-piperazinyl group, a 4-ethyl-1-piperazinyl group, a 4-propyl-1-piperazinyl group, a 4-isopropyl-1-piperazinyl group, a 4-tert-butyl-1-piperazinyl group, a 4-hydroxymethyl-1-piperazinyl group, a 4-(1-hydroxy-1-methylethyl)-1-piperazinyl group, a 4-(2-hydroxy-2-methylpropyl)-1-piperazinyl group, a 4-(2-hydroxy-2-methylpropionyl)-1-piperazinyl group, a 4-cyclopropyl-1-piperazinyl group, a 4-cyclobutyl-1-piperazinyl group, a 4-cyclopropylmethyl-1-piperazinyl group, a 4-(1-acetyl-3-azetidinyl)-1-piperazinyl group, a 4-cyclopentyl-1-piperazinyl group, a 4-(2-hydroxycyclopentyl)-1-piperazinyl group, a 4-(2-hydroxyethyl)-1-piperazinyl group, a 4-(2-methoxyethyl)-1-piperazinyl group, a 4-(formyl)-1-piperazinyl group, a 4-(hydroxyacetyl)-1-piperazinyl group, a 4-(2-ethoxyethyl)-1-piperazinyl group, a 4-(2-hydroxy-2-methylpropyl)-1-piperazinyl group, a 4-(3-fluoro-2-hydroxypropyl)-1-piperazinyl group, a 4-(difluoroacetyl)-1-piperazinyl group, a 4-acetyl-1-piperazinyl group, a 4-propionyl-1-piperazinyl group, a 4-methyl-2-methoxymethyl-1-piperazinyl group, a 4-(methoxyacetyl)-1-piperazinyl group, a 4-(2-dimethylaminomethylacetyl)-1-piperazinyl group, a 4-tert-butoxycarbonyl-1-piperazinyl group, a 4-methylsulfonyl-1-piperazinyl group, a 4-(2-(methylsulfonyl)ethyl)-1-piperazinyl group, a 4-(dimethylcarbamoyl) group, a 4-(dimethylcarbamoylmethyl)-1-piperazinyl group, a 4-(2-(dimethylamino)acetyl)-1-piperazinyl group, a 4-(2-methoxy-2-methylpropionyl)-1-piperazinyl group, a 4-methyl-3-oxo-1-piperazinyl group, a (4-methyl-1-piperazinyl)methyl group, a piperidino group, a 4-hydroxypiperidino group, a morpholino group, a 3-(dimethylaminomethyl)-1-morpholino group, a 3-hydroxymethyl-1-morpholino group, a thiomorpholino group, a 1,1-dioxidothiomorpholino group, a perhydro-1H-azepin-1-yl group, a perhydro-1H-1,4-diazepin-1-yl group, a 4-methylperhydro-1H-1,4-diazepin-1-yl group, a 5-oxo-perhydro-1H-1,4-diazepin-1-yl group, a 4-acetyl-perhydro-1H-1,4-diazepin-1-yl group, a 4-methyl-5-oxo-perhydro-1H-1,4-diazepin-1-yl group, a 3-azetidinyl group, a 3-hydroxy-1-azetidinyl group, a 3-(2-hydroxyethoxy)-1-azetidinyl group, a 3-dimethylamino-1-pyrrolidinyl group, a 3-(tert-butylamino)-1-pyrrolidinyl group, a 4-piperidyl group, a 1-methyl-4-piperidyl group, a 1-ethyl-4-piperidyl group, a 4-hydroxy-1-piperidyl group, a 4-(ethoxycarbonyl)-1-piperidinyl group, a 1-acetyl-4-piperidyl group, a 4-acetyl-1-piperidyl group, a 1-(2-hydroxyethyl)-4-piperidyl group, a 1-(2-methylsulfonylethyl)-4-piperidyl group, a 4-hydroxy-4-piperidyl group, a 4-hydroxy-1-methyl-4-piperidyl group, a 4-(2-hydroxy-2-propynyl)-1-piperidyl group, a 1-tert-butoxycarbonyl-4-hydroxy-4-piperidyl group, a 2-pyridylmethyl-(methyl)-amino group, a 3-azetidinyloxy group, a 1-methyl-3-azetidinyloxy group, a 1-ethyl-3-azetidinyloxy group, a 1-propyl-3-azetidinyloxy group, a 1-isopropyl-3-azetidinyloxy group, a 1-(2-hydroxyethyl)-3-azetidinyloxy group, a 4-piperidyloxy group, a 1-methyl-4-piperidyloxy group, a 1-ethyl-4-piperidyloxy group, a 1-cyclobutyl-4-piperidyloxy group, a 2-dimethylaminoethoxy group, a 3-(dimethylamino)-propyl group, a dimethylaminomethyl group, a diethylaminomethyl group, a methylpropylaminomethyl group, an isopropylmethylaminomethyl group, a 2-dimethylamino-1-methyl-ethoxy group, a 2-dimethylamino-propoxy group and a 3-dimethylamino-propoxy group. Among these, preferred is a 1-piperazinyl group, a 4-methyl-1-piperazinyl group, a 4-isopropyl-1-piperazinyl group, a 4-(2-hydroxy-2-methylpropyl)-1-piperazinyl group, a 4-(2-hydroxy-2-methylpropionyl)-1-piperazinyl group, a 4-cyclopropyl-1-piperazinyl group, a 4-(1-acetyl-3-azetidinyl)-1-piperazinyl group, a 4-(2-methoxyethyl)-1-piperazinyl group, a 4-(formyl)-1-piperazinyl group, a 4-(hydroxyacetyl)-1-piperazinyl group, a 4-(difluoroacetyl)-1-piperazinyl group, a 4-acetyl-1-piperazinyl group, a 4-(methoxyacetyl)-1-piperazinyl group, a 4-(2-dimethylaminomethylacetyl)-1-piperazinyl group, a 4-tert-butoxycarbonyl-1-piperazinyl group, a 4-(dimethylcarbamoylmethyl)-1-piperazinyl group, a 4-(2-methoxy-2-methylpropionyl)-1-piperazinyl group, a (4-methyl-1-piperazinyl)methyl group, a 4-methyl-perhydro-1H-1,4-diazepin-1-yl group, a 4-acetyl-perhydro-1H-1,4-diazepin-1-yl group, a 3-hydroxy-1-azetidinyl group, a 3-(2-hydroxyethoxy)-1-azetidinyl group, a 4-hydroxy-1-piperidyl group, a 4-(ethoxycarbonyl)-1-piperidinyl group, a 1-acetyl-4-piperidyl group, a 4-acetyl-1-piperidyl group, a 4-(2-hydroxy-2-propynyl)-1-piperidyl group, a 2-dimethylaminoethoxy group, a 3-dimethylamino-propoxy group or the like, more preferred is a 4-methyl-1-piperazinyl group, a 4-(2-hydroxy-2-methylpropyl)-1-piperazinyl group, a 4-(1-acetyl-3-azetidinyl)-1-piperazinyl group, a 4-acetyl-1-piperazinyl group, a 1-acetyl-4-piperidyl group or the like, and particularly preferred is a 4-methyl-1-piperazinyl group or the like.

As the substituent of $Ar^1$, preferred is, for example, a halogen atom, a C1-C6 alkyl group, a hydroxy-C1-C6 alkyl group, a C1-C6 alkoxy group, a group represented by -$Q^1$-$A^1$-$Q^2$-$A^2$($R^{1a}$)$R^{1b}$ or the like, and more preferred is a group represented by -$Q^1$-$A^1$-$Q^2$-$A^2$($R^{1a}$)$R^{1b}$ or the like.

As the "aryl group" per se of the aryl group which is denoted by $Ar^1$ and may have the above-mentioned substituent, for example, a phenyl group or the like is preferred. Further, as the "heteroaryl group" per se of the heteroaryl group which is denoted by $Ar^1$ and may have the above-mentioned substituent, for example, a pyrazolyl group, a pyridyl or the like is preferred.

Therefore, as $Ar^1$, preferred is, for example, a group obtained by substituting a phenyl group, a pyrazolyl group, a pyridyl group or the like with a halogen atom, a C1-C6 alkyl group, a hydroxy-C1-C6 alkyl group, a C1-C6 alkoxy group, a group represented by -Q$^1$-A$^1$-Q$^2$-A$^2$(R$^{1a}$)R$^{1b}$ or the like, and particularly preferred is a phenyl group substituted with one group represented by -Q$^1$-A$^1$-Q$^2$-A$^2$(R$^{1a}$)R$^{1b}$, a phenyl group substituted with one group represented by -Q$^1$-A$^1$-Q$^2$-A$^2$(R$^{1a}$)R$^{1b}$ and also with a C1-C6 alkyl group or the like, etc.

More specifically, as Ar$^1$, for example, a phenyl group, a 4-hydroxymethyl-3-methylphenyl group, a 4-isopropyloxyphenyl group, a 4-acetylphenyl group, a 3,5-dimethyl-4-(2-dimethylaminoethoxy)phenyl group, a 4(1-methyl-1H-pyrazol-4-yl)phenyl group, a 4-(1-piperazinyl)phenyl group, a 3-methyl-4-(1-piperazinyl)phenyl group, a 3-hydroxymethyl-4-(1-piperazinyl)phenyl group, a 4-(4-methyl-1-piperazinyl)phenyl group, a 3-methyl-4-(4-methyl-1-piperazinyl) phenyl group, a 3-hydroxymethyl-4-(4-methyl-1-piperazinyl)phenyl group, a 3-methoxy-(4-methyl-1-piperazinyl)phenyl group, a 4-(4-ethyl-1-piperazinyl)phenyl group, a 4-(4-isopropyl-1-piperazinyl)phenyl group, a 4-(4-ethyl-1-piperazinyl)-3-hydroxymethylphenyl group, a 4-(4-(2-hydroxy-2-methylpropyl)-1-piperazinyl)phenyl group, a 4-(4-(2-hydroxy-2-methylpropionyl)-1-piperazinyl)phenyl group, a 4(4-cyclopropyl-1-piperazinyl)phenyl group, a 4-(4-dimethylcarbamoylmethyl)-1-piperazinyl)phenyl group, a 4-(4-isopropyl-1-piperazinyl)phenyl group, a 3-methyl-4-(4-isopropyl-1-piperazinyl)phenyl group, a 4-(4-tert-butyl-1-piperazinyl)phenyl group, a 4-(4-cyclopropyl-1-piperazinyl) phenyl group, a 4-(4-cyclopropyl-1-piperazinyl)-3-methylphenyl group, a 4-(4-cyclopropyl-1-piperazinyl)-3-hydroxymethylphenyl group, a 4-(4-cyclobutyl-1-piperazinyl)phenyl group, a 4-(4-cyclobutyl-1-piperazinyl)-3-methylphenyl group, a 4-(4-cyclopropylmethyl-1-piperazinyl)phenyl group, a 4-(4-cyclopropylmethyl-1-piperazinyl)-3-methylphenyl group, a 4-(4-(1-acetyl-3-azetidinyl)-1-piperazinyl)phenyl group, a 4-(4-(2-hydroxyethyl)-1-piperazinyl)phenyl group, a 4-(4-(2-hydroxyethyl)-1-piperazinyl)-3-methylphenyl group, a 4-(4-(2-methoxyethyl)-1-piperazinyl)phenyl group, a 4-(4-acetyl-1-piperazinyl)phenyl group, a 3-methyl-4-(4-acetyl-1-piperazinyl)phenyl group, a 4-(4-(hydroxyacetyl)-1-piperazinyl)phenyl group, a 4-(4-(2-methoxyethyl)-1-piperazinyl)phenyl group, a 4-(4-(formyl)-1-piperazinyl)phenyl group, a 4-(4-(difluoroacetyl)-1-piperazinyl)phenyl group, a 4-(4-(2-methoxyacetyl)-1-piperazinyl)phenyl group, a 4-(4-(2-dimethylaminomethylacetyl)-1-piperazinyl)phenyl group, a 3-methyl-4-(4-tert-butoxycarbonyl-1-piperazinyl)phenyl group, a 3-hydroxymethyl-4-(4-(2-methoxyacetyl)-1-piperazinyl)phenyl group, a 4-(4-(2-methoxy-2-methylpropionyl)-1-piperazinyl)phenyl group, a 4-(4-methyl-2-methoxymethyl-1-piperazinyl)phenyl group, a 4-(4-methylsulfonyl-1-piperazinyl)phenyl group, a 3-methyl-4-(4-methylsulfonyl-1-piperazinyl)phenyl group, a 4-(4-(2-(dimethylamino)acetyl)-1-piperazinyl)phenyl group, a 4-(4-methyl-3-oxo-1-piperazinyl)phenyl group, a 3-methyl-4-(4-methyl-3-oxo-1-piperazinyl)phenyl group, a 4-(4-methyl-1-piperazinyl)methyl)phenyl group, a 4-(4-hydroxypiperidino)phenyl group, a 4-(4-hydroxypiperidino)-3-methylphenyl group, a 4-(4-hydroxypiperidino)-3-hydroxymethylphenyl group, a 4-morpholinophenyl group, a 3-methyl-4-morpholinophenyl group, a 3-hydroxymethyl-4-morpholinophenyl group, a 4-(3-(dimethylaminomethyl)-1-morpholino)phenyl group, a 4-(3-hydroxymethyl-1-morpholino)phenyl group, a 4-(1,1-dioxidothiomorpholino) phenyl group, a 3-methyl-4-(1,1-dioxidothiomorpholino)phenyl group, a 4-(4-methyl-perhydro-1H-1,4-diazepin-1-yl)phenyl group, a 4-(4-methyl-5-oxo-perhydro-1H-1,4-diazepin-1-yl)phenyl group, a 4-(4-acetyl-perhydro-1H-1,4-diazepin-1-yl)phenyl group, a 4-(3-hydroxymethyl-3-dimethylamino-1-pyrrolidinyl)phenyl group, a 4-(3-tert-butylamino)-1-pyrrolidinyl)phenyl group, a 4-(4-piperidyl)phenyl group, a 4-(1-methyl-4-piperidyl)phenyl group, a 3-methyl-4-(4-piperidyl)phenyl group, a 4-(4-hydroxy-4-piperidyl)phenyl group, a 4-(4-hydroxy-1-methyl-4-piperidyl)phenyl group, a 4-(1-(2-hydroxyethyl)-4-piperidyl)phenyl group, a 3-methyl-4-(4-hydroxy-1-piperidyl)phenyl group, a 4-(ethoxycarbonyl)-1-piperidinyl group, a 4-(1-acetyl-4-piperidyl)phenyl group, a 4-(4-acetyl-1-piperidyl)phenyl group, a 4-(1-(2-hydroxyethyl)-4-piperidyl)-3-methylphenyl group, a 4-(4-(2-hydroxy-2-propynyl)-1-piperidyl)phenyl group, a 4-(1-tert-butoxycarbonyl-4-hydroxy-4-piperidyl)phenyl group, a 3-methyl-4-(3-hydroxy-1-azetidinyl)phenyl group, a 4-(3-(2-hydroxyethoxy)-1-azetidinyl)phenyl group, a 4-(3-azetidinyloxy)phenyl group, a 4-(3-azetidinyloxy)-3-methylphenyl group, a 4-(1-ethyl-3-azetidinyloxy)phenyl group, a 4-(1-ethyl-3-azetidinyloxy)-3-methylphenyl group, a 4-(1-isopropyl-3-azetidinyloxy)phenyl group, a 4-(1-isopropyl-3-azetidinyloxy)-3-methylphenyl group, a 4-(1-(2-hydroxyethyl)-3-azetidinyloxy)phenyl group, a 4-(1-(2-hydroxyethyl)-3-azetidinyloxy)-3-methylphenyl group, a 4-(2-dimethylaminoethoxy)phenyl group, a 4-(3-(dimethylamino)-propyl)phenyl group, a 4-(dimethylaminomethyl) phenyl group, a 4-(2-dimethylamino-1-methyl-ethoxy)phenyl group, a 4-(2-dimethylamino-propoxy)phenyl group, a 3-(3-dimethylamino-propoxy)-4-methoxyphenyl group, a 4-(3-dimethylamino-propoxy)phenyl group or the like is suitable. Among these, preferred is a phenyl group, a 4-(1-piperazinyl)phenyl group, a 4-(4-methyl-1-piperazinyl)phenyl group, a 3-methyl-4-(4-methyl-1-piperazinyl)phenyl group, a 3-methoxy-(4-methyl-1-piperazinyl)phenyl group, a 4-(4-isopropyl-1-piperazinyl)phenyl group, a 4-(4-(2-hydroxy-2-methylpropyl)-1-piperazinyl)phenyl group, a 4-(4-(2-hydroxy-2-methylpropionyl)-1-piperazinyl)phenyl group, a 4-(4-cyclopropyl-1-piperazinyl)phenyl group, a 4-(4-dimethylcarbamoylmethyl)-1-piperazinyl)phenyl group, a 4-(4-(1-acetyl-3-azetidinyl)-1-piperazinyl)phenyl group, a 4-(4-acetyl-1-piperazinyl)phenyl group, a 3-methyl-4-(4-acetyl-1-piperazinyl)phenyl group, a 4-(4-(hydroxyacetyl)-1-piperazinyl)phenyl group, a 4-(4-(2-methoxyethyl)-1-piperazinyl)phenyl group, a 4-(4-(formyl)-1-piperazinyl)phenyl group, a 4-(4-(difluoroacetyl)-1-piperazinyl)phenyl group, a 4-(4-(2-methoxyacetyl)-1-piperazinyl)phenyl group, a 4-(4-(2-dimethylaminomethylacetyl)-1-piperazinyl)phenyl group, a 3-methyl-4-(4-tert-butoxycarbonyl-1-piperazinyl)phenyl group, a 4-(4-(2-methoxy-2-methylpropionyl)-1-piperazinyl)phenyl group, a 4-(4-methyl-1-piperazinyl)methyl)phenyl group, a 4-(4-methyl-perhydro-1H-1,4-diazepin-1-yl)phenyl group, a 4-(4-acetyl-perhydro-1H-1,4-diazepin-1-yl)phenyl group, a 3-methyl-4-(4-hydroxy-1-piperidyl)phenyl group, a 4-(ethoxycarbonyl)-1-piperidinyl group, a 4-(1-acetyl-4-piperidyl)phenyl group, a 4-(4-acetyl-1-piperidyl)phenyl group, a 4-(4-(2-hydroxy-2-propynyl)-1-piperidyl)phenyl group, a 3-methyl-4-(3-hydroxy-1-azetidinyl)phenyl group, a 4-(3-(2-hydroxyethoxy)-1-azetidinyl)phenyl group, a 4-(2-dimethylaminoethoxy) phenyl group, a 4-(3-dimethylamino-propoxy)phenyl group or the like, more preferred is a 4-(4-methyl-1-piperazinyl) phenyl group, a 3-methyl-4-(4-methyl-1-piperazinyl)phenyl group, a 4-(4-(2-hydroxy-2-methylpropyl)-1-piperazinyl) phenyl group, a 4-(4-(1-acetyl-3-azetidinyl)-1-piperazinyl) phenyl group, a 4-(4-acetyl-1-piperazinyl)phenyl group, a 3-methyl-4-(4-acetyl-1-piperazinyl)phenyl group, a 4-(1-acetyl-4-piperidyl)phenyl group or the like, and particularly preferred is a 3-methyl-4-(4-methyl-1-piperazinyl)phenyl group or the like.

$R^1$ denotes a hydrogen atom, or denotes a C1-C6 alkyl group which may have a substituent selected from the group consisting of a halogen atom, a hydroxy group, a cyano group, a C1-C6 alkoxy group, a C3-C6 cycloalkyl group, a C2-C7 alkanoyl group and a C1-C6 alkylsulfonyl group, or denotes an aryl, aralkyl or heteroaryl group which may have a substituent selected from the group consisting of a halogen atom, a hydroxy group, a cyano group, an amino group, a C1-C6 alkyl group, a C1-C6 alkoxy group, a halo-C1-C6 alkyl group and a hydroxy-C1-C6 alkyl group.

The "C1-C6 alkyl group which may have a substituent selected from the group consisting of a halogen atom, a hydroxy group, a cyano group, a C1-C6 alkoxy group, a C3-C6 cycloalkyl group, a C2-C7 alkanoyl group and a C1-C6 alkylsulfonyl group" denoted by $R^1$ means the above-mentioned C1-C6 alkyl group which is unsubstituted or substituted with a substituent selected from the group consisting of a halogen atom, a hydroxy group, a cyano group, a C1-C6 alkoxy group, a C3-C6 cycloalkyl group, a C2-C7 alkanoyl group and a C1-C6 alkylsulfonyl group, and one or two or more, preferably one to three of the above-mentioned substituents which are the same or different can be substituted for the respective groups at any substitutable positions.

As the halogen atom as the substituent, for example, a fluorine atom, a chlorine atom or the like is preferred.

As the C1-C6 alkyl group as the substituent, for example, a methyl group, an ethyl group or the like is preferred.

As the "C1-C6 alkyl group which may have a substituent selected from the group consisting of a halogen atom, a hydroxy group, a cyano group, a C1-C6 alkoxy group, a C3-C6 cycloalkyl group, a C2-C7 alkanoyl group and a C1-C6 alkylsulfonyl group" denoted by $R^1$, preferred is, for example, a methyl group, an ethyl group, a propyl group, an isopropyl group, a 2-hydroxyethyl group, a 2,2-difluoroethyl group, a 2,2,2-trifluoroethyl group or the like, and more preferred is a methyl group, an ethyl group, a 2-hydroxyethyl group or the like.

The "aryl, aralkyl or heteroaryl group which may have a substituent selected from the group consisting of a halogen atom, a hydroxy group, a cyano group, an amino group, a C1-C6 alkyl group, a C1-C6 alkoxy group, a halo-C1-C6 alkyl group and a hydroxy-C1-C6 alkyl group" denoted by $R^1$ means the above-mentioned aryl, aralkyl or heteroaryl group which is unsubstituted or has a substituent at any substitutable position, and as the substituent, one or two or more, preferably one or two members which are the same or different can be selected from the group consisting of a halogen atom, a hydroxy group, a cyano group, an amino group, a C1-C6 alkyl group, a C1-C6 alkoxy group, a halo-C1-C6 alkyl group and a hydroxy-C1-C6 alkyl group.

As the halogen atom as the substituent, for example, a fluorine atom, a chlorine atom or the like is preferred.

As the C1-C6 alkyl group as the substituent, for example, a methyl group, an ethyl group or the like is preferred.

As the aryl group which may have the above-mentioned substituent denoted by $R^1$, for example, a phenyl group, a 1-naphthyl group, a 2-chlorophenyl group, a 2,6-dichlorophenyl group, a 2-cyanophenyl group, a 2-chloro-6-cyanophenyl group or the like is preferred.

As the heteroaryl group which may have the above-mentioned substituent denoted by $R^1$, for example, a 2-pyridyl group, a 1-methyl-3-pyrazolyl group or the like is preferred.

As the aralkyl group which may have the above-mentioned substituent denoted by $R^1$, for example, a benzyl group, an α-methylbenzyl group or the like is preferred.

As a preferred embodiment of $R^1$, for example, a hydrogen atom, or a C1-C6 alkyl group which may be substituted with a halogen atom or a hydroxy group is preferred.

More specifically, for example, a hydrogen atom, a methyl group, an ethyl group, a 2-hydroxyethyl group or the like is suitable. Among these, preferred is a hydrogen atom, a methyl group, a 2-hydroxyethyl group or the like, and more preferred is a hydrogen atom, a methyl group or the like.

$R^2$ denotes an unsubstituted aralkyl group, or a group represented by the formula (a):

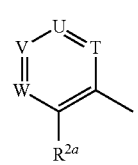

(a)

can be exemplified.

In the formula, $R^{2a}$ denotes a halogen atom, a hydroxy group, a cyano group, an amino group, a nitro group, a carbamoyl group, a C1-C6 alkyl group, a C1-C6 alkylsulfonyl group, a C1-C6 alkoxy group, a halo-C1-C6 alkyl group, a hydroxy-C1-C6 alkyl group or a C1-C6 alkoxy-C1-C6 alkyl group; T, U, V and W each independently denote a methine group which may be substituted with a halogen atom, a hydroxy group, a cyano group, an amino group, a nitro group, a carbamoyl group, a C1-C6 alkyl group, a C1-C6 alkylsulfonyl group, a C1-C6 alkoxy group, a halo-C1-C6 alkyl group, a hydroxy-C1-C6 alkyl group and a C1-C6 alkoxy-C1-C6 alkyl group or a nitrogen atom, at least two of which denote the methine group. As a more preferred embodiment of $R^2$, a case in which $R^2$ is a group represented by the formula (a), wherein $R^{2a}$ is a halogen atom, and T is a methine group substituted with a halogen atom or a C1-C6 alkyl group, and the like can be exemplified.

As the "halogen atom" denoted by $R^{2a}$, for example, a fluorine atom, a chlorine atom and the like can be exemplified, and preferred is a chlorine atom or the like.

As the "C1-C6 alkyl group" denoted by $R^{2a}$, for example, a methyl group or the like is preferred.

As the "C1-C6 alkylsulfonyl group" denoted by $R^{2a}$, for example, a methylsulfonyl group or the like is preferred.

As the "C1-C6 alkoxy group" denoted by $R^{2a}$, for example, a methoxy group or the like is preferred.

As the "halo-C1-C6 alkyl group" denoted by $R^{2a}$, for example, a fluoromethyl group, a trifluoromethyl group or the like is preferred.

As the "hydroxy-C1-C6 alkyl group" denoted by $R^{2a}$, for example, a hydroxymethyl group or the like is preferred.

As the "C1-C6 alkoxy-C1-C6 alkyl group" denoted by $R^{2a}$, for example, a methoxymethyl group or the like is preferred.

As $R^{2a}$, a chlorine atom is more preferred.

As T, an unsubstituted methine group; a methine group substituted with a halogen atom such as a fluorine atom or a chlorine atom; a methine group substituted with a C1-C6 alkyl group such as a methyl group; a methine group substituted with a halo-C1-C6 alkyl group such as a trifluoromethyl group or the like is suitable, and among these, preferred is a methine group substituted with a halogen atom such as a chlorine atom.

As W, an unsubstituted methine group or a nitrogen atom is preferred.

As U and V, an unsubstituted methine group is preferred for both.

As the "unsubstituted aralkyl group" denoted by $R^2$, for example, a benzyl group, a phenethyl group or the like is preferred.

As $R^2$, more specifically, for example, a phenyl group, a 2-chlorophenyl group, a 2-nitrophenyl group, a 2-cyanophenyl group, a 2-carbamoylphenyl group, a 2-methylsulfonylphenyl group, a 2-fluorophenyl group, a 2,5-dichlorophenyl group, a 2,6-dichlorophenyl group, a 2-chloro-3-fluorophenyl group, a 2-chloro-4-fluorophenyl group, a 2-chloro-5-fluorophenyl group, a 2-chloro-6-fluorophenyl group, a 2,6-dichloro-4-fluorophenyl group, a 2-chloro-4,6-difluorophenyl group, a 2-chloro-4-methylphenyl group, a 2-chloro-6-methylphenyl group, a 2-chloro-6-hydroxymethylphenyl group, a 2,6-dichloro-4-methylphenyl group, a 2-chloro-5-trifluoromethylphenyl group, a 2,6-dichloro-4-trifluoromethylphenyl group, a 2-cyanophenyl group, a 2-iodophenyl group, a 2-alkoxyphenyl group, a 2,6-dichloro-4-hydroxymethylphenyl group, a 2-methyl-6-methoxymethylphenyl group, a 2-methyl-6-fluoromethylphenyl group, a 2-methyl-6-methoxyphenyl group, a 2-chloro-3-pyridyl group, a 3-methyl-2-pyridyl group, a 2,4-dichloro-3-pyridyl group, a 2,6-difluorophenyl group, a benzyl group, a phenethyl group or the like is suitable, and among these, preferred is a 2-chlorophenyl group, a 2,6-dichlorophenyl group, a 2-chloro-6-fluorophenyl group, a 2-chloro-6-methylphenyl group, a 2-chloro-6-hydroxymethylphenyl group, a 2,4-dichloro-3-pyridyl group or the like, and particularly, more preferred is a 2,6-dichlorophenyl group, a 2-chloro-6-methylphenyl group or the like.

$R^3$ denotes a hydrogen atom or a C1-C6 alkyl group.

As the "C1-C6 alkyl group" denoted by $R^3$, for example, a methyl group or the like is preferred.

As $R^3$, a hydrogen atom is preferred.

As one embodiment of the invention, a group represented by the general formula (I-1):

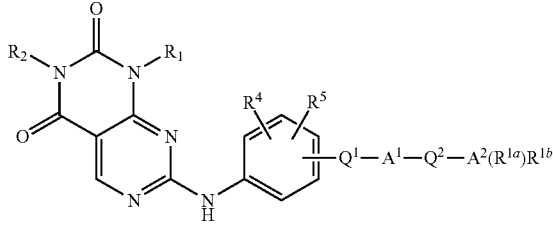

(I-1)

can be exemplified.

In the formula, $Q^1, Q^2, A^1, A^2, R^{1a}, R^{1b}, R^1$ and $R^2$ have the same meanings as described above, and preferred examples of the $Q^1, Q^2, A^1, A^2, R^{1a}, R^{1b}, R^1$ and $R^2$ are the same as the preferred examples for the formula (I); $R^4$ and $R^5$ each independently denote a hydrogen atom, a halogen atom, a C1-C6 alkyl group, a halo-C1-C6 alkyl group, a hydroxy-C1-C6 alkyl group, a C1-C6 alkoxy group, a C2-C7 alkanoyl group, a hydroxy-C1-C6 alkylamino group, a carbamoyl group or a hydroxy-C1-C6 alkylcarbamoyl group.

As the "halogen atom" denoted by $R^4$ or $R^5$, for example, a fluorine atom, a chlorine atom or the like is preferred.

As the "C1-C6 alkyl group" denoted by $R^4$ or $R^5$, for example, a methyl group, an ethyl group or the like is preferred.

As the "halo-C1-C6 alkyl group" denoted by $R^4$ or $R^5$, for example, a fluoromethyl group, a difluoromethyl group or a trifluoromethyl is preferred.

As the "hydroxy-C1-C6 alkyl group" denoted by $R^4$ or $R^5$, for example, a hydroxymethyl group, a 2-hydroxyethyl group or the like is preferred.

As the "C1-C6 alkoxy group" denoted by $R^4$ or $R^5$, for example, a methoxy group, an ethoxy group or the like is preferred.

As the "C2-C7 alkanoyl group" denoted by $R^4$ or $R^5$, for example, an acetyl group or the like is preferred.

As the "hydroxy-C1-C6 alkylamino group" denoted by $R^4$ or $R^5$, for example, a hydroxymethylamino group, a 2-hydroxyethylamino group, a 1-hydroxy-1-methylethylamino group, a 1,2-dihydroxyethylamino group, a 3-hydroxypropylamino group and the like can be exemplified, and among these, a hydroxymethylamino group, a 2-hydroxyethylamino group or the like is preferred.

As the "hydroxy-C1-C6 alkylcarbamoyl group" denoted by $R^4$ or $R^5$, for example, a hydroxymethylcarbamoyl group, a 2-hydroxyethylcarbamoyl group, a 1-hydroxy-1-methylethylcarbamoyl group, a 1,2-dihydroxyethylcarbamoyl group, a 3-hydroxypropylcarbamoyl group and the like can be exemplified, and among these, a hydroxymethylcarbamoyl group, a 2-hydroxyethylcarbamoyl group or the like is preferred.

More specific examples of $R^4$ or $R^5$ include a hydrogen atom, a fluorine atom, a chlorine atom, a methyl group, an ethyl group, a fluoromethyl group, a difluoromethyl group, a trifluoromethyl group, a hydroxymethyl group, a 2-hydroxyethyl group, a methoxy group, an ethoxy group, an acetyl group, a hydroxymethylamino group, a 2-hydroxyethylamino group, a 1-hydroxy-1-methylethylamino group, a 1,2-dihydroxyethylamino group, a 3-hydroxypropylamino group, a hydroxymethylcarbamoyl group, a 2-hydroxyethylcarbamoyl group, a 1-hydroxy-1-methylethylcarbamoyl group, a 1,2-dihydroxyethylcarbamoyl group and a 3-hydroxypropylcarbamoyl group. Among these, as a preferred embodiment of $R^4$ and $R^5$, a case in which one of $R^4$ and $R^5$ is a methyl group and the other is a hydrogen atom; a case in which both are a hydrogen atom, and the like can be exemplified, and particularly preferred is a case in which one of $R^4$ and $R^5$ is a methyl group and the other is a hydrogen atom, or the like.

In the case where a given variable (such as $R^{1a}$) appears more than once in a given constituent element, the definition thereof associated with each appearance is independent of all the other appearances thereof. Further, a combination of the substituent and the variable is allowed only when the combination results in a stable compound. A line drawn from a substituent to the inside of a ring system indicates that the indicated bond may be attached to any substitutable ring atom.

The term "any substitutable position" means a position where a substitutable hydrogen atom is attached to a carbon, nitrogen, oxygen and/or sulfur atom, substitution of the hydrogen atom is chemically allowed and the substitution results in a stable compound.

In the compounds of the invention, the replacement of a methylene group constituting the C1-C6 alkylene group with, for example, an oxygen atom, a sulfur atom, a sulfinyl, sulfonyl, carbonyl, vinylene or imino group is allowed when the replacement is chemically allowed and the replacement results in a stable compound.

Depending on the type of the substituent and the salt form thereof, the compounds of the invention may be in the form of a stereoisomer such as an optical isomer, a diastereomer or a geometrical isomer, or a tautomer, and the compounds of the invention include all these stereoisomers and tautomers and mixtures thereof.

The invention includes various crystals, amorphous forms, salts, hydrates and solvates of the compounds of the invention.

Further, prodrugs of the compounds of the invention are also within the scope of the invention. In general, such prodrugs are functional derivatives of the compounds of the invention which can be easily converted into compounds that are needed in the body. Accordingly, the term "administration" as used herein for the method of treating various diseases according to the invention includes not only administration of a specified compound but also administration of a compound which is converted into the specified compound in the body after it is administered to patients. A common procedure for selection and production of a suitable prodrug derivative is described in, for example, "Design of Prodrugs" ed. H. Bundgaard, Elsevier, 1985, etc., and the entire descriptions are referred to and incorporated herein as a part of the specification of the present application. Metabolites of these compounds include active compounds that are produced by leaving the compounds of the invention in a biological environment, and they are within the scope of the invention.

Specific examples of the compounds represented by the general formula (I), and salts and N-oxide derivatives thereof include the compounds, and salts and N-oxide derivatives thereof described in Examples, however, preferred examples of the compounds includes:

(1) 3-(2,6-dichlorophenyl)-7-{[3-methyl-4-(4-methylpiperazin-1-yl)phenyl]amino}pyrimido[4,5-d]pyrimidine-2,4(1H,3H)-dione;
(2) 3-(2-chloro-6-methylphenyl)-7-{[3-methyl-4-(4-methylpiperazin-1-yl)phenyl]amino}pyrimido[4,5-d]pyrimidine-2,4(1H,3H)-dione;
(3) 3-(2,6-dichlorophenyl)-1-methyl-7-{[3-methyl-4-(4-methylpiperazin-1-yl)phenyl]amino}pyrimido[4,5-d]pyrimidine-2,4(1H,3H)-dione;
(4) 3-(2,6-dichlorophenyl)-1-methyl-7-{[4-(4-methylpiperazin-1-yl)phenyl]amino}pyrimido[4,5-d]pyrimidine-2,4(1H,3H)-dione;
(5) 3-(2,6-dichlorophenyl)-1-(1-methyl-1H-pyrazol-3-yl)-7-{[3-methyl-4-(4-methylpiperazin-1-yl)phenyl]amino}pyrimido[4,5-d]pyrimidine-2,4(1H,3H)-dione;
(6) 3-(2,6-dichlorophenyl)-1-(2-hydroxyethyl)-7-{[3-methyl-4-(4-methylpiperazin-1-yl)phenyl]amino}pyrimido[4,5-d]pyrimidine-2,4(1H,3H)-dione;
(7) 3-(2,4-dichloropyridin-3-yl)-7-{[3-methyl-4-(4-methylpiperazin-1-yl)phenyl]amino}pyrimido[4,5-d]pyrimidine-2,4(1H,3H)-dione;
(8) 3-(2,6-dichlorophenyl)-1-ethyl-7-{[4-(4-methylpiperazin-1-yl)phenyl]amino}pyrimido[4,5-d]pyrimidine-2,4(1H,3H)-dione;
(9) 7-{[4-(4-acetylpiperazin-1-yl)-3-methylphenyl]amino}-3-(2,6-dichlorophenyl)pyrimido[4,5-d]pyrimidine-2,4(1H,3H)-dione;
(10) 7-({4-[4-(1-acetylazetidin-3-yl)piperazin-1-yl]phenyl}amino)-3-(2,6-dichlorophenyl)-1-methylpyrimido[4,5-d]pyrimidine-2,4(1H,3H)-dione;
(11) 3-(2,6-dichlorophenyl)-7-({4-[4-(2-hydroxy-2-methylpropyl)piperazin-1-yl]phenyl}amino)pyrimido[4,5-d]pyrimidine-2,4(1H,3H)-dione;
(12) 3-(2,6-dichlorophenyl)-7-[(4-{4-[(dimethylamino)acetyl]piperazin-1-yl}phenyl)amino]pyrimido[4,5-d]pyrimidine-2,4(1H,3H)-dione;
(13) 3-(2-chlorophenyl)-1-methyl-7-{[3-methyl-4-(4-methylpiperazin-1-yl)phenyl]amino}pyrimido[4,5-d]pyrimidine-2,4(1H,3H)-dione;
(14) 3-(2,6-dichlorophenyl)-7-{[4-(4-methypiperazin-1-yl)phenyl]amino}pyrimido[4,5-d]pyrimidine-2,4(1H,3H)-dione;
(15) 7-{[4-(1-acetylpiperidin-4-yl)phenyl]amino}-3-(2,6-dichlorophenyl)-1-methylpyrimido[4,5-d]pyrimidine-2,4(1H,3H)-dione;
(16) 3-(2,6-dichlorophenyl)-7-{[4-(3-hydroxyazetidin-1-yl)-3-methylphenyl]amino}pyrimido[4,5-d]pyrimidine-2,4(1H,3H)-dione;
(17) 3-(2,6-dichlorophenyl)-7-{[4-(4-hydroxypiperidin-1-yl)-3-methylphenyl]amino}pyrimido[4,5-d]pyrimidine-2,4(1H,3H)-dione;
(18) 7-{[4-(4-acetylpiperazin-1-yl)phenyl]amino}-1-ethyl-3-(2,6-dichlorophenyl)pyrimido[4,5-d]pyrimidine-2,4(1H,3H)-dione;
(19) 3-(2,6-dichlorophenyl)-7-({4-[4-(difluoroacetyl)piperazin-1-yl]phenyl}amino)pyrimido[4,5-d]pyrimidine-2,4(1H,3H)-dione;
(20) 3-(2-chlorophenyl)-7-{[3-methyl-4-(piperazin-1-yl)phenyl]amino}pyrimido[4,5-d]pyrimidine-2,4(1H,3H)-dione;
(21) 7-{[4(4-acetylpiperidin-1-yl)phenyl]amino}-3-(2,6-dichlorophenyl)pyrimido[4,5-d]pyrimidine-2,4(1H,3H)-dione;
(22) 3-(2-chlorophenyl)-7-{[3-methyl-4-(4-methylpiperazin-1-yl)phenyl]amino}pyrimido[4,5-d]pyrimidine-2,4(1H,3H)-dione;
(23) 3-(2,6-dichlorophenyl)-7-({4-[(4-methylpiperazin-1-yl)methyl]phenyl}amino)pyrimido[4,5-d]pyrimidine-2,4(1H,3H)-dione;
(24) 3-(2,6-dichlorophenyl)-7-({4-[4-(2-hydroxy-2-methylpropionyl)piperazin-1-yl]phenyl}amino)pyrimido[4,5-d]pyrimidine-2,4(1H,3H)-dione;
(25) 3-(2,6-dichlorophenyl)-7-({4-[4-(2-hydroxypropan-2-yl)piperidin-1-yl]phenyl}amino)pyrimido[4,5-d]pyrimidine-2,4(1H,3H)-dione;
(26) 7-{[4-(4-acetylpiperazin-1-yl)phenyl]amino}-3-(2,6-dichlorophenyl)pyrimido[4,5-d]pyrimidine-2,4(1H,3H)-dione;
(27) 3-(2,6-dichlorophenyl)-7-({4-[4-(methoxyacetyl)piperazin-1-yl]phenyl}amino)pyrimido[4,5-d]pyrimidine-2,4(1H,3H)-dione;
(28) 7-{[4-(4-acetyl-1,4-diazepan-1-yl)phenyl]amino}-3-(2,6-dichlorophenyl)pyrimido[4,5-d]pyrimidine-2,4(1H,3H)-dione;
(29) 2-[4-(4-{[6-(2,6-dichlorophenyl)-5,7-dioxo-5,6,7,8-tetrahydropyrimido[4,5-d]pyrimidin-2-yl]amino}phenyl)piperazin-1-yl]-N,N-dimethylacetamide;
(30) 3-(2,6-dichlorophenyl)-7-(phenylamino)pyrimido[4,5-d]pyrimidine-2,4(1H,3H)-dione;
(31) 3-(2,6-dichlorophenyl)-7-{[4-(4-methyl-1,4-diazepan-1-yl)phenyl]amino}pyrimido[4,5-d]pyrimidine-2,4(1H,3H)-dione;
(32) 3-(2,6-dichlorophenyl)-7-({4-[4-hydroxyacetyl)piperazin-1-yl]phenyl}amino)pyrimido[4,5-d]pyrimidine-2,4(1H,3H)-dione;
(33) 3-(2,6-dichlorophenyl)-7-({4-[4-(2-methoxy-2-methylpropionyl)piperazin-1-yl]phenyl}amino)pyrimido[4,5-d]pyrimidine-2,4(1H,3H)-dione;
(34) ethyl 1-(4-{[6-(2,6-dichlorophenyl)-5,7-dioxo-5,6,7,8-tetrahydropyrimido[4,5-d]pyrimidin-2-yl]amino}phenyl)piperidine-4-carboxylate;
(35) 4-(4-{[6-(2,6-dichlorophenyl)-5,7-dioxo-5,6,7,8-tetrahydropyrimido[4,5-d]pyrimidin-2-yl]amino}phenyl)piperazine-1-carbaldehyde;

(36) 3-(2,6-dichlorophenyl)-7-({4-[4-(methoxyacetyl)piperazin-1-yl]phenyl}amino)-1-methylpyrimido[4,5-d]pyrimidine-2,4(1H,3H)-dione;
(37) 3-[2-chloro-6-(hydroxymethyl)phenyl]-7-{[3-methyl-4-(4-methylpiperazin-1-yl)phenyl]amino}pyrimido[4,5-d]pyrimidine-2,4(1H,3H)-dione;
(38) 3-(2-chloro-6-fluorophenyl)-7-{[3-methyl-4-(4-methylpiperazin-1-yl)phenyl]amino}pyrimido[4,5-d]pyrimidine-2,4(1H,3H)-dione;
(39) 3-(2,6-dichlorophenyl)-7-({4-[3-(2-hydroxyethoxy)azetidin-1-yl]phenyl}amino)pyrimido[4,5-d]pyrimidine-2,4(1H,3H)-dione;
(40) 7-{[4-(4-acetylpiperazin-1-yl)-3-methylphenyl]amino}-3-(2-chlorophenyl)pyrimido[4,5-d]pyrimidine-2,4(1H,3H)-dione;
(41) 3-(2,6-dichlorophenyl)-7-({4-[3-(dimethylamino)propoxy]phenyl}amino)pyrimido[4,5-d]pyrimidine-2,4(1H,3H)-dione;
(42) 3-(2-chlorophenyl)-1-ethyl-7-{[3-methyl-4-(4-methylpiperazin-1-yl)phenyl]amino}pyrimido[4,5-d]pyrimidine-2,4(1H,3H)-dione;
(43) 3-(2-chloro-6-methylphenyl)-7-({4-[4-(2-hydroxy-2-methylpropyl)piperazin-1-yl]phenyl}amino)pyrimido[4,5-d]pyrimidine-2,4(1H,3H)-dione;
(44) 3-(2,6-dichlorophenyl)-1-(2-hydroxyethyl)-7-({4-[4-(methoxyacetyl)piperazin-1-yl]phenyl}amino)pyrimido[4,5-d]pyrimidine-2,4(1H,3H)-dione;
(45) 3-(2-chlorophenyl)-7-{[4-(4-cyclopropylpiperazin-1-yl)phenyl]amino}pyrimido[4,5-d]pyrimidine-2,4(1H,3H)-dione;
(46) 3-(2,6-difluorophenyl)-7-{[3-methyl-4-(4-methylpiperazin-1-yl)phenyl]amino}pyrimido[4,5-d]pyrimidine-2,4(1H,3H)-dione;
(47) 3-[2-(methoxymethyl)-6-methylphenyl]-7-{[3-methyl-4-(4-methylpiperazin-1-yl)phenyl]amino}pyrimido[4,5-d]pyrimidine-2,4(1H,3H)-dione;
(48) 3-[2-(hydroxymethyl)-6-methylphenyl]-7-{[3-methyl-4-(4-methylpiperazin-1-yl)phenyl]amino}pyrimido[4,5-d]pyrimidine-2,4(1H,3H)-dione;
(49) 3-(2-iodophenyl)-7-{[3-methyl-4-(4-methylpiperazin-1-yl)phenyl]amino}pyrimido[4,5-d]pyrimidine-2,4(1H,3H)-dione;
(50) 3-(2,6-dichlorophenyl)-7-({4-[2-(dimethylamino)ethoxy]phenyl}amino)pyrimido[4,5-d]pyrimidine-2,4(1H,3H)-dione;
(51) 3-(2-chlorophenyl)-7-{[4-(4-methylpiperazin-1-yl)phenyl]amino}pyrimido[4,5-d]pyrimidine-2,4(1H,3H)-dione;
(52) 3-(2-chlorophenyl)-7-({4-[4-(propan-2-yl)piperazin-1-yl]phenyl}amino)pyrimido[4,5-d]pyrimidine-2,4(1H,3H)-dione;
(53) 3-(2-chlorophenyl)-7-{[3-methoxy-4-(4-methylpiperazin-1-yl)phenyl]amino}pyrimido[4,5-d]pyrimidine-2,4(1H,3H)-dione;
(54) 1-ethyl-3-[2-(fluoromethyl)-6-methylphenyl]-7-{[3-methyl-4-(4-methylpiperazin-1-yl)phenyl]amino}pyrimido[4,5-d]pyrimidine-2,4(1H,3H)-dione;
(55) 3-(3,5-dichloropyridin-4-yl)-7-{[3-methyl-4-(4-methylpiperazin-1-yl)phenyl]amino}pyrimido[4,5-d]pyrimidine-2,4(1H,3H)-dione;
(56) 3-(2-methoxy-6-methylphenyl)-7-{[3-methyl-4-(4-methylpiperazin-1-yl)phenyl]amino}pyrimido[4,5-d]pyrimidine-2,4(1H,3H)-dione;
(57) 3-(2-chloro-4-fluorophenyl)-7-{[3-methyl-4-(4-methylpiperazin-1-yl)phenyl]amino}pyrimido[4,5-d]pyrimidine-2,4(1H,3H)-dione;
(58) 7-{[3-methyl-4-(4-methylpiperazin-1-yl)phenyl]amino}-3-(2-methylphenyl)pyrimido[4,5-d]pyrimidine-2,4(1H,3H)-dione;
(59) 7-{[3-methyl-4-(4-methylpiperazin-1-yl)phenyl]amino}-3-(2-nitrophenyl)pyrimido[4,5-d]pyrimidine-2,4(1H,3H)-dione;
(60) tert-butyl 4-(4-{[6-(2-chlorophenyl)-5,7-dioxo-5,6,7,8-tetrahydropyrimido[4,5-d]pyrimidin-2-yl]amino}-2-methylphenyl)piperazine-1-carboxylate;
(61) 3-(2-chlorophenyl)-7-({4-[4-(2-methoxyethyl)piperazin-1-yl]phenyl}amino)pyrimido[4,5-d]pyrimidine-2,4(1H,3H)-dione;
(62) 2-[7-{[3-methyl-4-(4-methylpiperazin-1-yl)phenyl]amino}-2,4-dioxo-1,4-dihydropyrimido[4,5-d]pyrimidin-3(2H)-yl]benzonitrile;
(63) 3-(2-methoxyphenyl)-7-{[3-methyl-4-(4-methylpiperazin-1-yl)phenyl]amino}pyrimido[4,5-d]pyrimidine-2,4(1H,3H)-dione;
(64) 2-[7-{[3-methyl-4-(4-methylpiperazin-1-yl)phenyl]amino}-2,4-dioxo-1,4-dihydropyrimido[4,5-d]pyrimidin-3(2H)-yl]benzamide;
(65) 3-benzyl-7-{[3-methyl-4-(4-methylpiperazin-1-yl)phenyl]amino}pyrimido[4,5-d]pyrimidine-2,4(1H,3H)-dione;
(66) 3-(2-chlorophenyl)-7-{[3-methyl-4-(4-methylpiperazin-1-yl)phenyl]amino}-1-(pyridin-2-yl)pyrimido[4,5-d]pyrimidine-2,4(1H,3H)-dione;
(67) 3-(2-chloropyridin-3-yl)-7-[3-methyl-4-(4-methylpiperazin-1-yl)phenyl]amino)pyrimido[4,5-d]pyrimidine-2,4(1H,3H)-dione;
(68) 3-(2-chlorophenyl)-7-{[3-methyl-4-(4-methylpiperazin-1-yl)phenyl]amino}-1-(1-methyl-1H-pyrazol-3-yl)pyrimido[4,5-d]pyrimidine-2,4(1H,3H)-dione;
(69) 7-{[3-methyl-4-(4-methylpiperazin-1-yl)phenyl]amino}-3-(2-phenylethyl)pyrimido[4,5-d]pyrimidine-2,4(1H,3H)-dione;
(70) 3-(2,5-dichlorophenyl)-7-{[3-methyl-4-(4-methylpiperazin-1-yl)phenyl]amino}pyrimido[4,5-d]pyrimidine-2,4(1H,3H)-dione;
(71) 7-{[3-methyl-4-(4-methylpiperazin-1-yl)phenyl]amino}-3-(3-methylpyridin-2-yl)pyrimido[4,5-d]pyrimidine-2,4(1H,3H)-dione; and
(72) 7-{[3-methyl-4-(4-methylpiperazin-1-yl)phenyl]amino}-3-[2-(methylsulfonyl)phenyl]pyrimido[4,5-d]pyrimidine-2,4(1H,3H)-dione. Among these, more preferred is:
(1) 3-(2,6-dichlorophenyl)-7-{[3-methyl-4-(4-methylpiperazin-1-yl)phenyl]amino}pyrimido[4,5-d]pyrimidine-2,4(1H,3H)-dione;
(2) 3-(2-chloro-6-methylphenyl)-7-{[3-methyl-4-(4-methylpiperazin-1-yl)phenyl]amino}pyrimido[4,5-d]pyrimidine-2,4(1H,3H)-dione;
(3) 3-(2,6-dichlorophenyl)-1-methyl-7-{[3-methyl-4-(4-methylpiperazin-1-yl)phenyl]amino}pyrimido[4,5-d]pyrimidine-2,4(1H,3H)-dione;
(4) 3-(2,6-dichlorophenyl)-1-methyl-7-{[4-(4-methylpiperazin-1-yl)phenyl]amino}pyrimido[4,5-d]pyrimidine-2,4(1H,3H)-dione;
(5) 3-(2,6-dichlorophenyl)-1-(1-methyl-1H-pyrazol-3-yl)-7-{[3-methyl-4-(4-methylpiperazin-1-yl)phenyl]amino}pyrimido[4,5-d]pyrimidine-2,4(1H,3H)-dione;
(6) 3-(2,6-dichlorophenyl)-1-(2-hydroxyethyl)-7-{[3-methyl-4-(4-methylpiperazin-1-yl)phenyl]amino}pyrimido[4,5-d]pyrimidine-2,4(1H,3H)-dione;
(7) 3-(2,4-dichloropyridin-3-yl)-7-{[3-methyl-4-(4-methylpiperazin-1-yl)phenyl]amino}pyrimido[4,5-d]pyrimidine-2,4(1H,3H)-dione;

(8) 3-(2,6-dichlorophenyl)-1-ethyl-7-{[4-(4-methylpiperazin-1-yl)phenyl]amino}pyrimido[4,5-d]pyrimidine-2,4(1H,3H)-dione;

(9) 7-{[4-(4-acetylpiperazin-1-yl)-3-methylphenyl]amino}-3-(2,6-dichlorophenyl)pyrimido[4,5-d]pyrimidine-2,4(1H,3H)-dione;

(10) 7-({4-[4-(1-acetylazetidin-3-yl)piperazin-1-yl]phenyl}amino)-3-(2,6-dichlorophenyl)-1-methylpyrimido[4,5-d]pyrimidine-2,4(1H,3H)-dione;

(11) 3-(2,6-dichlorophenyl)-7-({4-[4-(2-hydroxy-2-methylpropyl)piperazin-1-yl]phenyl}amino)pyrimido[4,5-d]pyrimidine-2,4(1H,3H)-dione;

(12) 3-(2,6-dichlorophenyl)-7-[(4-{4-[(dimethylamino)acetyl]piperazin-1-yl}phenyl)amino]pyrimido[4,5-d]pyrimidine-2,4(1H,3H)-dione;

(13) 3-(2-chlorophenyl)-1-methyl-7-{[3-methyl-4-(4-methylpiperazin-1-yl)phenyl]amino}pyrimido[4,5-d]pyrimidine-2,4(1H,3H)-dione;

(14) 3-(2,6-dichlorophenyl)-7-{[4-(4-methypiperazin-1-yl)phenyl]amino}pyrimido[4,5-d]pyrimidine-2,4(1H,3H)-dione;

(15) 7-{[4-(1-acetylpiperidin-4-yl)phenyl]amino}-3-(2,6-dichlorophenyl)-1-methylpyrimido[4,5-d]pyrimidine-2,4(1H,3H)-dione or the like, and particularly preferred is:

(1) 3-(2,6-dichlorophenyl)-7-{[3-methyl-4-(4-methylpiperazin-1-yl)phenyl]amino}pyrimido[4,5-d]pyrimidine-2,4(1H,3H)-dione;

(2) 3-(2-chloro-6-methylphenyl)-7-{[3-methyl-4-(4-methylpiperazin-1-yl)phenyl]amino}pyrimido[4,5-d]pyrimidine-2,4(1H,3H)-dione;

(3) 3-(2,6-dichlorophenyl)-1-methyl-7-{[3-methyl-4-(4-methylpiperazin-1-yl)phenyl]amino}pyrimido[4,5-d]pyrimidine-2,4(1H,3H)-dione;

(9) 7-{[4-(4-acetylpiperazin-1-yl)-3-methylphenyl]amino}-3-(2,6-dichlorophenyl)pyrimido[4,5-d]pyrimidine-2,4(1H,3H)-dione or the like.

Subsequently, methods for producing the compounds according to the invention will be described.

The compounds (I) of the invention can be produced according to the following production methods, or the methods shown in Examples and Production Examples described below. However, the methods for producing the compounds (I) of the invention are not limited to these reaction examples.

Production Method 1

A compound represented by the general formula (II):

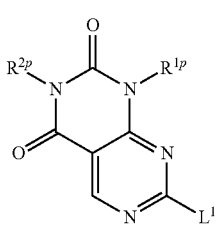

wherein $R^{1p}$ denotes a hydrogen atom, or denotes a C1-C6 alkyl group which may have a substituent selected from the group consisting of a halogen atom, an optionally protected hydroxy group, a cyano group, a C1-C6 alkoxy group, a C3-C6 cycloalkyl group, a C2-C7 alkanoyl group and a C1-C6 alkylsulfonyl group, or denotes an aryl, aralkyl or heteroaryl group which may have a substituent selected from the group consisting of a halogen atom, an optionally protected hydroxy group, a cyano group, an optionally protected amino group, a C1-C6 alkyl group, a C1-C6 alkoxy group, a halo-C1-C6 alkyl group and an optionally protected hydroxy-C1-C6 alkyl group;

$R^{2p}$ denotes an unsubstituted aralkyl group, or denotes a group represented by the formula (ap):

$R^{2ap}$ denotes a halogen atom, an optionally protected hydroxy group, a cyano group, an optionally protected amino group, a nitro group, a carbamoyl group, a C1-C6 alkyl group, a C1-C6 alkylsulfonyl group, a C1-C6 alkoxy group, a halo-C1-C6 alkyl group, an optionally protected hydroxy-C1-C6 alkyl group or a C1-C6 alkoxy-C1-C6 alkyl group;

T, U, V and W each independently denote a methine group which may have a substituent selected from the group consisting of a halogen atom, an optionally protected hydroxy group, a cyano group, an optionally protected amino group, a nitro group, a carbamoyl group, a C1-C6 alkyl group, a C1-C6 alkylsulfonyl group, a C1-C6 alkoxy group, a halo-C1-C6 alkyl group, an optionally protected hydroxy-C1-C6 alkyl group and a C1-C6 alkoxy-C1-C6 alkyl group or a nitrogen atom, at least two of which denote the methine group; and $L^1$ denotes a leaving group, is reacted with a compound represented by the general formula (III):

wherein $Ar^{1p}$ denotes an aryl or heteroaryl group which may have a substituent selected from the group consisting of a halogen atom, a C1-C6 alkyl group, a halo-C1-C6 alkyl group, an optionally protected hydroxy-C1-C6 alkyl group, a C1-C6 alkoxy group, a C2-C7 alkanoyl group, an optionally protected hydroxy-C1-C6 alkylamino group, a carbamoyl group, an optionally protected hydroxy-C1-C6 alkylcarbamoyl group, a heteroaryl group which may be substituted with a C1-C6 alkyl group and a group represented by -$Q^{1p}$-$A^{1p}$-$Q^{2p}$-$A^{2p}$($R^{1ap}$)$R^{1bp}$;

$A^{1p}$ denotes a single bond, an oxygen atom or a sulfur atom, or denotes an imino group which may be substituted with a C1-C6 alkyl group or a protective group;

$A^{2p}$ denotes a nitrogen atom, or denotes a methine group which may be substituted with an optionally protected hydroxy group, a C1-C6 alkyl group or an optionally protected hydroxy-C1-C6 alkyl group;

$Q^{1p}$ denotes a single bond, a carbonyl group or a methylene group which may be substituted with a C1-C6 alkyl group;

$Q^{2p}$ denotes a single bond or an ethylene or trimethylene group which may be substituted with a C1-C6 alkyl group;

$R^{1ap}$ and $R^{1bp}$ each independently denote a protective group for an amino or imino group, a hydrogen atom, a C1-C6 alkyl group or an optionally protected hydroxy-C1-C6 alkyl group, or are combined together to denote a C1-C6 alkylene group, wherein one or two or more methylene groups constituting the C1-C6 alkylene group may be each independently replaced with an oxygen atom, a sulfur atom, a sulfinyl group, a sulfonyl group, an optionally protected carbonyl group, a vinylene group or a group represented by —N($R^{1cp}$)— or may be substituted with an optionally protected hydroxy group, a C1-C6 alkyl group or a group represented by —$R^{10cp}$;

$R^{1cp}$ denotes a hydrogen atom, an optionally protected formyl group, a C2-C6 alkenyl group or a group represented by -$Q^3$-$A^3$($R^{1d}$)$R^{1e}$;

$R^{10cp}$ denotes a group represented by -$Q^{30p}$-$A^{30p}$($R^{10dp}$)$R^{10ep}$;

$A^{3p}$ and $A^{30p}$ each independently denote a nitrogen atom, or denote a methine group which may be substituted with an optionally protected hydroxy group, a C1-C6 alkyl group or an optionally protected hydroxy-C1-C6 alkyl group;

$Q^{3p}$ and $Q^{30p}$ each independently denote a single bond or a C1-C6 alkylene group, wherein one or two or more methylene groups constituting the C1-C6 alkylene group may be each independently replaced with an oxygen atom, a sulfur atom, an optionally protected carbonyl group, a sulfinyl group or a sulfonyl group, or substituted with a halogen atom, a cyano group, an optionally protected hydroxy group or a C1-C6 alkyl group;

$R^{1dp}$ and $R^{1ep}$ each independently denote a protective group for an amino or imino group, a hydrogen atom, a halogen atom, a cyano group, an optionally protected hydroxy group, a C1-C6 alkyl group or an optionally protected hydroxy-C1-C6 alkyl group, or are combined together to denote a C1-C6 alkylene group, wherein one or two or more methylene groups constituting the C1-C6 alkylene group may be each independently replaced with an oxygen atom, a sulfur atom, a sulfinyl group, a sulfonyl group, an optionally protected carbonyl group, a vinylene group or a group represented by —N($R^{1fp}$)— or may be substituted with an optionally protected hydroxy group or a C1-C6 alkyl group; $R^{1fp}$ and $R^{10fp}$ each independently denote a hydrogen atom, a C1-C6 alkyl group, a halo-C1-C6 alkyl group, a C2-C6 alkenyl group or a C2-C7 alkanoyl group;

$R^{10dp}$ and $R^{10ep}$ each independently denote a protective group for an amino or imino group, a hydrogen atom, a halogen atom, a cyano group, an optionally protected hydroxy group, a C1-C6 alkyl group or an optionally protected hydroxy-C1-C6 alkyl group, or are combined together to denote a C1-C6 alkylene group, wherein one or two or more methylene groups constituting the C1-C6 alkylene group may be each independently replaced with an oxygen atom, a sulfur atom, a sulfinyl group, a sulfonyl group, an optionally protected carbonyl group, a vinylene group or a group represented by —N($R^{10fp}$)— or may be substituted with an optionally protected hydroxy group or a C1-C6 alkyl group; and $R^3$ denotes a hydrogen atom or a C1-C6 alkyl group, or a salt thereof to form a compound represented by the general formula (IV):

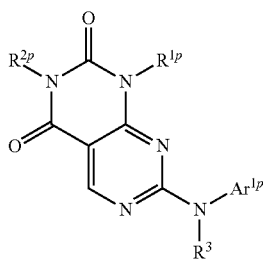

(IV)

wherein $Ar^{1p}$, $R^{1p}$, $R^{2p}$ and $R^3$ have the same meanings as described above, and in the case where the compound (IV) has a protective group for an amino, imino, hydroxy or carbonyl group, (1) a step of removing the protective group; or (2) in the case where the objective compound is an N-oxide derivative, a step of oxidizing a nitrogen atom in the compound is appropriately selected and carried out, whereby a compound represented by the general formula (I) or an N-oxide derivative thereof can be produced.

In the case where the compound of the general formula (N) does not have a protective group for an amino, imino, hydroxy or carbonyl group, the compound (IV) represents a compound of the general formula (I).

As the leaving group denoted by $L^1$, for example, a halogen atom such as a fluorine atom, a chlorine atom, a bromine atom or an iodine atom; an organic sulfonyl group such as a methylsulfinyl group, a methylsulfonyl group, an ethylsulfonyl group or a phenylsulfonyl group; an organic sulfonyloxy group such as a methylsulfonyloxy group, a trifluoromethylsulfonyloxy group or a p-tolylsulfonyloxy group and the like can be exemplified, and among these, preferred is a chlorine atom, a methylsulfinyl group, a methylsulfonyl group or the like.

This production method is a general production method for the compounds represented by the general formula (I).

In the above reaction, in the case where an amino group, an imino group, a hydroxy group, a carbonyl group or the like which is not involved in the reaction is present in the reaction substance, after the amino, imino, hydroxy or carbonyl group is properly protected by a protective group for an amino or imino group, a protective group for a hydroxy group, or a protective group for a carbonyl group, the reaction is carried out, and the protective group can be removed after the reaction.

The "protective group for an amino or imino group" is not particularly limited as long as it has its function, and examples thereof include aralkyl groups such as a benzyl group, a p-methoxybenzyl group, a 3,4-dimethoxybenzyl group, an o-nitrobenzyl group, a p-nitrobenzyl group, a benzhydryl group and a trityl group; lower alkanoyl groups such as a formyl group, an acetyl group, a propionyl group, a butyryl group and a pivaloyl group; a benzoyl group; arylalkanoyl groups such as a phenylacetyl group and a phenoxyacetyl group; lower alkoxycarbonyl groups such as a methoxycarbonyl group, an ethoxycarbonyl group, a propyloxycarbonyl group and a tert-butoxycarbonyl group; aralkyloxycarbonyl groups such as a benzyloxycarbonyl group, a p-nitrobenzyloxycarbonyl group and a phenethyloxycarbonyl group; lower alkylsilyl groups such as a trimethylsilyl group and a tert-butyldimethylsilyl group; a tetrahydropyranyl group; a trimethylsilylethoxymethyl group; lower alkylsulfonyl groups such as a methylsulfonyl group and an ethylsulfonyl group; and arylsulfonyl groups such as a benzenesulfonyl group and a toluenesulfonyl group, and particularly preferred is an acetyl group, a benzoyl group, a tert-butoxycarbonyl group, a trimethylsilylethoxymethyl group, a methylsulfonyl group or the like.

The "protective group for a hydroxy group" is not particularly limited as long as it has its function, and examples thereof include lower alkyl groups such as a methyl group, an ethyl group, a propyl group, an isopropyl group and a tert-butyl group; lower alkylsilyl groups such as a trimethylsilyl group and a tert-butyldimethylsilyl group; lower alkoxymethyl groups such as a methoxymethyl group and a 2-methoxyethoxymethyl group; a tetrahydropyranyl group; a trimethylsilylethoxymethyl group; aralkyl groups such as a benzyl group, a p-methoxybenzyl group, a 2,3-dimethoxybenzyl group, an o-nitrobenzyl group, a p-nitrobenzyl group and a trityl group; and acyl groups such as a formyl group and an acetyl group, and particularly preferred is a methyl group, a methoxymethyl group, a tetrahydropyranyl group, a trityl group, a trimethylsilylethoxymethyl group, a tert-butyldimethylsilyl group, an acetyl group or the like.

The "protective group for a carbonyl group" is not particularly limited as long as it has its function, and examples thereof include acetals and ketals such as ethylene ketal, trimethylene ketal and dimethyl ketal.

The reaction of the compound represented by the general formula (II) with the compound represented by the general formula (III) is generally carried out using the compound (III) in an amount of from 1 mole to excess moles, preferably from 1 mole to 1.5 moles per mole of the compound (II).

The reaction is generally carried out in an inert solvent which does not adversely affect the reaction. As the inert solvent, a nonpolar solvent such as an aromatic hydrocarbon, for example, toluene, benzene, xylene or the like; a polar solvent such as methylene chloride, chloroform, tetrahydrofuran, dioxane, dimethylformamide, N-methylpyrrolidone, dimethyl sulfoxide or the like; or a polar solvent such as an alcohol, for example, methanol, ethanol, butanol, isopropanol or the like; or a mixed solvent thereof is preferred.

Further, the above-mentioned reaction is preferably carried out in the presence of a base or an acid.

As the acid, for example, an inorganic acid such as hydrochloric acid, sulfuric acid, nitric acid, phosphoric acid or perchloric acid; an organic acid such as maleic acid, fumaric acid, tartaric acid, citric acid, ascorbic acid or trifluoroacetic acid; sulfonic acid such as methanesulfonic acid, isethionic acid, benzenesulfonic acid or p-toluenesulfonic acid; or Lewis acid such as hafnium trifluoromethanesulfonate, ytterbium trifluoromethanesulfonate or scandium trifluoromethanesulfonate can be used, and preferred is p-toluenesulfonic acid, hafnium trifluoromethanesulfonate or the like.

The used amount of the acid is generally from 0.01 moles to excess moles, preferably from 0.02 to 1.5 moles per mole of the compound represented by the general formula (II).

As the base, an organic base such as triethylamine, diisopropylethylamine, pyridine or 4-dimethylaminopyridine; or an inorganic base such as sodium hydrogen carbonate, sodium carbonate, potassium carbonate, cesium carbonate, sodium hydroxide or potassium hydroxide can be used.

The used amount of the base is generally from 1 mole to excess moles, preferably from 1 to 3 moles per mole of the compound represented by the general formula (II).

The reaction temperature is generally from 0° C. to 200° C., preferably from 20° C. to 150° C.

The reaction time is generally from 5 minutes to 7 days, preferably from 30 minutes to 24 hours.

After completion of the reaction, a common treatment is carried out, whereby a crude product of the compound represented by the general formula (IV) can be obtained. The thus obtained compound represented by the general formula (IV) is purified according to a common procedure or is not purified, and in the case where the compound (IV) has a protective group for an amino, imino, hydroxy or carbonyl group, (1) a step of removing the protective group; or
(2) in the case where the objective compound is an N-oxide derivative, a step of oxidizing a nitrogen atom in the compound is appropriately selected and carried out, whereby a compound represented by the general formula (I) or an N-oxide derivative thereof can be produced.

The method for removing the protective group varies depending on the type of the protective group, the stability of the objective compound (I) or the like, however, the protective group can be removed by appropriately combining removal reactions of the protective groups for an amino, hydroxy and carbonyl group. For example, the protective group is removed according to the method described in the document [see Protective Groups in Organic Synthesis, Third Ed., by T. W. Greene, John Wiley & Sons, (1999)] or a modified method thereof, for example, by solvolysis using an acid or a base, i.e., by a method of treating the compound with a 0.01 moles to a large excess amount of an acid, preferably trifluoroacetic acid, formic acid, hydrochloric acid or the like, or with an equimolar amount to a large excess amount of a base, preferably potassium hydroxide, calcium hydroxide or the like; by chemical reduction using a metal hydride complex or the like, or by catalytic reduction using a palladium-carbon catalyst, a Raney nickel catalyst or the like.

The step of producing an N-oxide derivative by oxidizing a nitrogen atom is carried out using an oxidizing agent such as m-chloroperbenzoic acid, dioxirane, sodium periodate or hydrogen peroxide.

The used amount of the oxidizing agent is generally from 0.5 moles to excess moles, preferably from 1 to 5 moles per mole of the compound represented by the general formula (IV).

The reaction is generally carried out in a solvent appropriately selected according to the oxidizing agent to be used in the reaction. For example, when m-chloroperbenzoic acid is used as the oxidizing agent, a solvent such as methylene chloride or chloroform is preferred, and when dioxirane is used as the oxidizing agent, a solvent such as acetone or water is preferred.

The reaction temperature is generally from −50° C. to 100° C., preferably from −20° C. to 50° C.

The reaction time is generally from 15 minutes to 7 days, preferably from 30 minutes to 24 hours.

The compound of the general formula (I) or an N-oxide derivative thereof can be easily isolated and purified by a common separation method. As such a method, for example, solvent extraction, recrystallization, column chromatography, preparative thin-layer chromatography and the like can be exemplified.

These compounds can be converted into pharmaceutically acceptable salts thereof according to a common procedure, and conversely, such salts can also be converted into the corresponding free compounds according to a common procedure.

The "salt" of the compound represented by the general formula (III) means a salt commonly used in the field of organic chemistry, and examples thereof include acid addition salts of the compound, when the compound has an amino group or a basic heterocyclic group, with an acid added to the amino group or basic heterocyclic group.

Examples of the acid addition salt include inorganic acid salts such as hydrochlorides, sulfates, nitrates, phosphates and perchlorates; organic acid salts such as maleates, fumarates, tartrates, citrates, ascorbates and trifluoroacetates; and sulfonates such as methanesulfonates, isethionates, benzenesulfonates and p-toluenesulfonates.

As the compound represented by the general formula (II) or (III), for example, a commercially available product is used, or the compound can be produced by appropriately combining the methods described in the documents (see WO 2007/067506, WO 2004/104007, Journal of Medicinal Chemistry, Vol. 48, pp. 2371-2387), modified methods thereof, the following methods, methods described in Examples and Production Examples and the like as needed.

Production Method A

This production method is a method for producing the compound represented by the general formula (II).

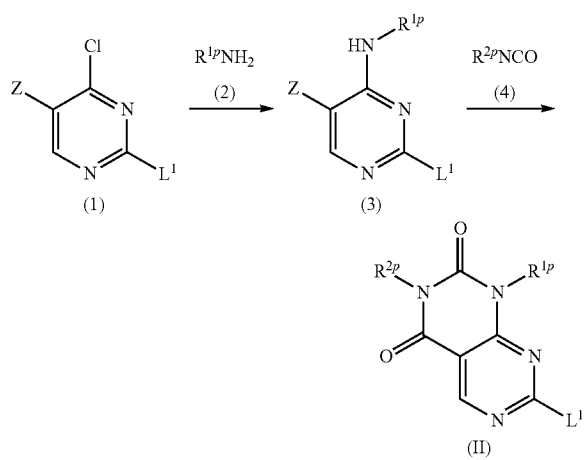

In the formula, Z denotes a group represented by —CO-OR$^{p1}$; R$^{p1}$ denotes an ester residue; and R$^{1p}$, R$^{2p}$ and L$^1$ have the same meanings as described above.

According to this production method, the compound represented by the general formula (II) can be produced by reacting a compound represented by the formula (1) with an amine represented by the formula (2) to form a compound represented by the formula (3) and then reacting the compound (3) with an isocyanate represented by the formula (4).

The step of reacting a compound represented by the formula (1) with an amine represented by the formula (2) to form a compound represented by the formula (3) is generally carried out using the amine (2) in an amount of from 0.5 moles to excess moles, preferably from 1 mole to 3.0 moles per mole of the compound (1).

The reaction is generally carried out in an inert solvent. As the inert solvent, for example, methylene chloride, chloroform, tetrahydrofuran, ethyl ether, benzene, toluene, dimethylformamide or the like or a mixed solvent thereof or the like is preferred.

Further, the above-mentioned reaction is preferably carried out in the presence of a base. As the base, for example, an organic base such as triethylamine, diisopropylethylamine, pyridine or 4-dimethylaminopyridine; or an inorganic base such as sodium hydroxide, potassium hydroxide, sodium carbonate, potassium carbonate or sodium hydrogen carbonate can be used.

In general, the base is preferably used in an amount of from 1 mole to excess moles per mole of the compound (1). Further, in the case where the base is in the form of a liquid, the base can be used as both solvent and base.

The reaction temperature is generally from −78° C. to 100° C., preferably from 20° C. to 80° C.

The reaction time is generally from 5 minutes to 7 days, preferably from 30 minutes to 24 hours.

The step of reacting a compound (3) with an isocyanate represented by the formula (4) to produce a compound represented by the general formula (II) is generally carried out using the isocyanate (4) in an amount of from 0.5 moles to excess moles, preferably from 1 mole to 3.0 moles per mole of the compound (3).

The reaction is generally carried out in an inert solvent. As the inert solvent, preferred is, for example, methylene chloride, chloroform, tetrahydrofuran, ethyl ether, benzene, toluene, dimethylformamide or the like or a mixed solvent thereof or the like, and more preferred is dimethylformamide or the like.

Further, the above-mentioned reaction is generally carried out in the presence of a base. As the base, for example, an organic base such as triethylamine, diisopropylethylamine, pyridine or 4-dimethylaminopyridine; or an inorganic base such as sodium hydride, potassium tert-butoxide or sodium tert-butoxide can be used.

In general, the base is preferably used in an amount of from 1 mole to excess moles per mole of the compound (3). Further, in the case where the base is in the form of a liquid, the base can be used as both solvent and base.

The reaction temperature is generally from −78° C. to 100° C., preferably from 20° C. to 80° C.

The reaction time is generally from 5 minutes to 7 days, preferably from 30 minutes to 24 hours.

As the compound represented by the general formula (1), (2) or (4), a commercially available product is used, or the compound can be produced by appropriately combining known methods, methods described in Examples and modified methods thereof as needed.

(Alternative Method)

With respective to a compound represented by the general formula (I), a compound represented by the above-mentioned formula (3) is reacted with a compound represented by the general formula (III) or a salt thereof to form a compound represented by the general formula (V-1):

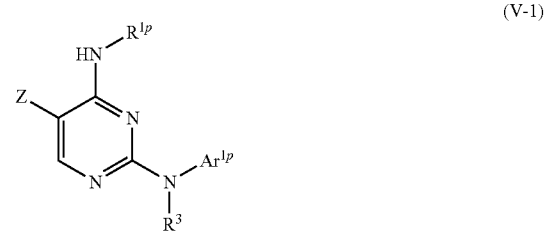

wherein Z, Ar$^{1p}$, R$^{1p}$ and R$^3$ have the same meanings as described above, and the compound (V-1) is reacted with an isocyanate represented by the above-mentioned formula (4) to form a compound represented by the general formula (IV):

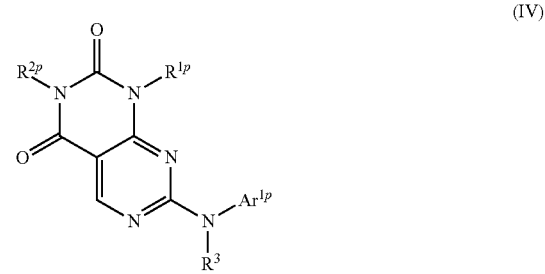

wherein Ar$^{1p}$, R$^{1p}$, R$^{2p}$ and R$^3$ have the same meanings as described above, and in the case where the compound has a protective group for an amino, imino, hydroxy or carbonyl group, (1) a step of removing the protective group; or (2) in the case where the objective compound is an N-oxide derivative, a step of oxidizing a nitrogen atom in the compound is appropriately selected and carried out, whereby the compound represented by the general formula (I) or an N-oxide derivative thereof can be produced.

The step of producing a compound represented by the general formula (V-1) by reacting a compound represented by the formula (3) with a compound represented by the general formula (III) or a salt thereof can be carried out according to the step of producing a compound represented by the formula (IV) by reacting a compound represented by the formula (II) with a compound represented by the formula (III) or a salt thereof in the above-mentioned Production Method 1.

As the salt of the compound represented by the formula (III) which can be used in this step, the salts of the compound represented by the formula (II) illustrated in the Production Method 1 can be exemplified.

The step of producing a compound represented by the general formula (IV) by reacting a compound (V-1) with an isocyanate represented by the formula (4) can be carried out according to the step of producing a compound represented by the general formula (II) by reacting a compound (3) with an isocyanate represented by the formula (4) in the above-mentioned Production Method A.

The step of removing the protective group and/or the step of producing an N-oxide derivative to be carried out as needed can be carried out in the same manner as described in the Production Method 1.

Hereinafter, Pharmacological Test Examples for the compounds of the invention will be shown.

Pharmacological Test 1 (Wee1 Kinase Inhibitory Effect)
(1) Purification of Wee1 Kinase A cDNA of Wee1 kinase with glutathione-S-transferase (GST) fused at the amino terminal thereof was inserted into a baculovirus expression vector to construct a recombinant baculovirus, with which cells of an insect cell line Sf9 were infected to overexpress the target protein. The infected cells were collected and lysed, and then the GST-tagged Wee1 kinase protein was adsorbed to a glutathione column and eluted from the column with glutathione, and the active fraction was desalted in a desalting column to give a purified enzyme.

(2) Measurement of Wee1 Kinase Activity

In measurement of the Wee1 kinase activity, a synthetic peptide, Poly(Lys, Tyr) hydrobromide (Lys:Tyr (4:1)) purchased from Sigma was used as the substrate.

The amount of the reaction mixture was 21.1 µL; and the composition of the reaction buffer was 50 mM Tris-HCl buffer (pH 7.4)/10 mM magnesium chloride/1 mM dithiothreitol. The purified Wee1 kinase, 2.5 µg of the substrate peptide, 10 µM of non-labeled adenosine triphosphate (ATP) and 1 µCi of [$\gamma$-$^{33}$P]-labeled ATP (2500 Ci/mmol or more) were added to the reaction buffer, and the resulting mixture was incubated at 30° C. for 30 minutes. Thereafter, 10 µL of 350 mM phosphate buffer was added to the reaction system to stop the reaction. The substrate peptide was adsorbed on a P81 paper filter 96-well plate and the plate was washed several times with 130 mM phosphate buffer, and the radioactivity thereof was counted using a liquid scintillation counter. The [$\gamma$-$^{33}$P]-labeled ATP was purchased from Amersham Bioscience, Ltd.

The addition of a test compound to the reaction system was carried out by preparing a series of dilutions of the compound with dimethyl sulfoxide (DMSO) and adding 1.1 µL of each dilution to the reaction system. As a control, 1.1 µL of DMSO was added to the reaction system.

As shown in Table 1, the compounds according to the invention exhibit an excellent Wee1 inhibitory effect.

TABLE 1

| Example | Wee1 Inhibitory activity (IC50, nM) |
|---------|-------------------------------------|
| 1       | 7                                   |
| 2       | 9                                   |
| 3       | 8                                   |
| 4       | 33                                  |
| 9       | 4                                   |
| 31      | 4                                   |
| 32      | 6                                   |
| 33      | 9                                   |

Subsequently, an inhibitory effect of the compound of the general formula (I) according to the invention on Cdc2 tyrosine-15 phosphorylation in cells will be described below.

Pharmacological Test 2 (Method for Determining Drug Effect Using Cells (Inhibitory Effect on Cdc2 (Cdk1) Tyrosine-15 Phosphorylation))

a) Reagents

Fetal bovine serum (FBS) was purchased from Morgate, Inc.; an RPMI-1640 medium and a DMEM medium were purchased from Invitrogen, Inc.; camptothecin was purchased from Sigma Co.; gemcitabine was purchased from Eli Lilly Japan K.K.; nocodazole and protease inhibitor cocktail were purchased from Sigma Co.; a rabbit anti-Cdc2 antibody and a mouse anti-Cdc2 antibody were purchased from Santa Cruz Biotechnology, Inc.; a rabbit anti-tyrosine-15-phosphorylated Cdc2 antibody and a horseradish peroxidase-labeled anti-mouse IgG antibody were purchased from Cell Signaling Technology, Inc.; and Sure Blue Reserve TMB peroxidase substrate was purchased from Kirkegaard & Perry Laboratories, Inc.

b) Cells

A human non-small cell lung cancer cell line (NCI-H1299) and a human colon cancer cell line (WiDr) can be obtained from American Type Culture Collection (ATCC).

c) Method for Determining Effect

In the method using NCI-H1299 cells, the cells were suspended in an RPMI-1640 medium supplemented with 10% FBS, and 100 µl, of the resulting cell suspension was dispensed in a Nunclon Delta treated 96-well plastic plate purchased from Nunc, Inc. at a density of 2000 cells per well, and the plate was incubated overnight at 37° C. under an atmosphere of 5% $CO_2$ and 95% air. Camptothecin was dissolved in dimethyl sulfoxide (DMSO) and further the resulting solution was diluted with an RPMI-1640 medium supplemented with 10% FBS. Then, 50 µL of the diluted solution was added to each well of the plate in which the cells were seeded in advance such that the final concentration of camptothecin was 200 nM, and the plate was incubated at 37° C. under an atmosphere of 5% $CO_2$ and 95% air for 16 hours. A test compound was serially diluted with DMSO, and further diluted with an RPMI-1640 medium supplemented with 10% FBS containing 4000 nM nocodazole. Then, 50 µL of the test compound solution was added to each well of the plate in which the cells treated with camptothecin were seeded, and the plate was incubated at 37° C. under an atmosphere of 5% $CO_2$ and 95% air for 8 hours. Then, the culture medium was removed from each well and 100 µL of a cell lysis buffer was added to each well, and the plate was shaken at 4° C. for 2 hours, and thereafter the liquid in the plate was frozen at −80° C. and then thawed, which was used as a lysed cell solution. Cdc2 and tyrosine-15-phosphorylated Cdc2 in this lysed cell solution were measured by an enzyme-linked immunosorbent assay (ELISA method), and a ratio of tyrosine-15-phosphorylated Cdc2 to Cdc2 was calculated to determine a 50% effective concentration ($EC_{50}$, nM) of the test compound for inhibition of phosphorylation in cells. The cell lysis buffer as used herein is an aqueous solution containing 20 mM HEPES (pH 7.5), 150 mM sodium chloride, 1 mM disodium ethylenediamine tetraacetate, 0.1% polyoxyethylene (10) octylphenyl ether, 1% protease inhibitor cocktail, 1 mM dithiothreitol, 2 mM sodium orthovanadate, 10 mM sodium fluoride and 10 mM glycerol diphosphate. The measurement of Cdc2 by the ELISA method was carried out as follows. 50 μL of a solution of a rabbit anti-Cdc2 antibody obtained by diluting the antibody to 200 times with 50 mM carbonate-bicarbonate buffer (pH 9.6) was dispensed into each well of a 96-well Maxisorb immunoplate purchased from Nunc, Inc., and the immunoplate was let stand overnight at 4° C. to immobilize the antibody thereto. Subsequently, each well was washed three times with phosphate buffered saline (PBS), and 300 μL of PBS containing 5% bovine serum albumin (5% BSA/PBS) was added to each well, and then, the immunoplate was let stand at room temperature for 2 hours. Thereafter, each well was washed again three times with PBS, and 50 μL of a solution of a mouse anti-Cdc2 antibody obtained by diluting the antibody to 100 times with Tris-HCl buffered saline containing 0.05% polyoxyethylene sorbitan monolaurate and 1% BSA (1% BSA/TBS-T) was added to each well and also 5 μL of the lysed cell solution was added thereto, and then, the immunoplate was let stand overnight at 4° C. Subsequently, each well was washed three times with Tris-HCl buffered saline containing 0.05% polyoxyethylene sorbitan monolaurate and 0.1% BSA (0.1% BSA/TBS-T), and 70 μL of a solution of a horseradish peroxidase-labeled anti-mouse IgG antibody obtained by diluting the antibody to 2000 times with 1% BSA/TBS-T was added to each well, and then, the immunoplate was let stand at room temperature for 3 hours. Finally, each well was washed five times with 0.1% BSA/TBS-T, and 100 μL of Sure Blue Reserve TMB peroxidase substrate was added to each well, and a chromogenic reaction was allowed to proceed for 15 minutes in a dark place at room temperature. Thereafter, 100 μL of 1 M hydrochloric acid was added to each well to stop the reaction, and measurement was carried out by the colorimetric method. The measurement of tyrosine-15-phosphorylated Cdc2 by the ELISA method was carried out as follows. 50 μL of a solution of a rabbit anti-tyrosine-15-phosphorylated Cdc2 antibody obtained by diluting the antibody to 100 times with 50 mM carbonate-bicarbonate buffer (pH 9.6) was dispensed into each well of a 96-well Maxisorb immunoplate, and the immunoplate was let stand overnight at 4° C. to immobilize the antibody thereto. Subsequently, each well was washed three times with PBS, and 300 μL of 5% BSA/PBS was added to each well, and then, the immunoplate was let stand at room temperature for 2 hours. Thereafter, each well was washed again three times with PBS, and 50 μL of a solution of a mouse anti-Cdc2 antibody obtained by diluting the antibody to 100 times with 1% BSA/TBS-T was added to each well and also 5 μL of the lysed cell solution was added thereto, and then, the immunoplate was let stand overnight at 4° C. Subsequently, each well was washed three times with 0.1% BSA/TBS-T, and 70 μL of a solution of a horseradish peroxidase-labeled anti-mouse IgG antibody obtained by diluting the antibody to 2000 times with 1% BSA/TBS-T was added to each well, and then, the immunoplate was let stand at room temperature for 3 hours. Finally, each well was washed five times with 0.1% BSA/TBS-T, and 100 μL of Sure Blue Reserve TMB peroxidase substrate was added to each well, and a chromogenic reaction was allowed to proceed for 5 minutes in a dark place at room temperature. Thereafter, 100 μt of 1 M hydrochloric acid was added to each well to stop the reaction, and measurement was carried out by the colorimetric method. The results are shown in Table 2.

In the method using WiDr cells, the cells are suspended in a DMEM medium supplemented with 10% FBS, and 100 μL of the resulting cell suspension is dispensed in a Nunclon Delta treated 96-well plastic plate at a density of 2000 cells per well, and the plate is incubated overnight at 37° C. under an atmosphere of 5% $CO_2$ and 95% air. Gemcitabine is dissolved in PBS and further the resulting solution is diluted with a DMEM medium supplemented with 10% FBS. Then, 50 μL of the diluted solution is added to each well of the plate in which the cells have been seeded in advance such that the final concentration of gemcitabine is 100 nM, and the plate is incubated at 37° C. under an atmosphere of 5% $CO_2$ and 95% air for 24 hours. A test compound is serially diluted with DMSO, and further diluted with a DMEM medium supplemented with 10% FBS containing 1200 nM nocodazole. Then, 50 μL of the test compound solution is added to each well of the plate in which the cells treated with gemcitabine have been seeded, and the plate is incubated at 37° C. under an atmosphere of 5% $CO_2$ and 95% air for 8 hours. Then, the culture medium is removed from each well and 100 of a cell lysis buffer is added to each well, and the plate is shaken at 4° C. for 2 hours, and thereafter the liquid in the plate is frozen at −80° C. and then thawed, which is used as a lysed cell solution. Cdc2 and tyrosine-15-phosphorylated Cdc2 in this lysed cell solution are measured by the ELISA method, and a ratio of tyrosine-15-phosphorylated Cdc2 to Cdc2 is calculated to determine a 50% effective concentration ($EC_{50}$, nM) of the test compound for inhibition of phosphorylation in cells. The measurement of Cdc2 by the ELISA method is carried out as follows. 50 μL of a solution of a rabbit anti-Cdc2 antibody obtained by diluting the antibody to 200 times with 50 mM carbonate-bicarbonate buffer (pH 9.6) is dispensed into each well of a 96-well Maxisorb plastic plate, and the plate is let stand overnight at 4° C. to immobilize the antibody thereto. Thereafter, each well is washed three times with PBS, and 300 μL of 5% BSA/PBS is added to each well, and then, the plate is let stand at room temperature for 2 hours. Thereafter, each well is washed again three times with PBS, and 50 μL of a solution of a mouse anti-Cdc2 antibody obtained by diluting the antibody to 100 times with 1% BSA/TBS-T is added to each well and also 10 μL of the lysed cell solution is added thereto, and then, the plate is let stand overnight at 4° C. Subsequently, each well is washed three times with 0.1% BSA/TBS-T, and 70 μL of a solution of a horseradish peroxidase-labeled anti-mouse IgG antibody obtained by diluting the antibody to 2000 times with 1% BSA/TBS-T is added to each well, and then, the plate is let stand at room temperature for 3 hours. Finally, each well is washed five times with 0.1% BSA/TBS-T, and 100 μL of Sure Blue Reserve TMB peroxidase substrate is added to each well, and a chromogenic reaction is allowed to proceed for 15 minutes in a dark place at room temperature. Thereafter, 100 μL of 1 M hydrochloric acid is added to each well to stop the reaction, and measurement is carried out by the colorimetric method. The measurement of tyrosine-15-phosphorylated Cdc2 by the ELISA method is carried out as follows. 50 μL of a solution of a rabbit anti-tyrosine-15-phosphorylated Cdc2 antibody obtained by diluting the antibody to 100 times with 50 mM carbonate-bicarbonate buffer (pH 9.6) is dispensed into each well of a 96-well Maxisorb plastic plate, and the plate is let stand overnight at 4° C. to immobilize the antibody thereto. Thereafter, each well is washed three times with PBS, and 300 μL of 5% BSA/PBS is added to each well, and then, the plate is let stand at room temperature for 2 hours. Thereafter, each well is washed again three times with PBS, and 50

µL of a solution of a mouse anti-Cdc2 antibody obtained by diluting the antibody to 100 times with 1% BSA/TBS-T is added to each well and also 10 µL of the lysed cell solution is added thereto, and then, the plate is let stand overnight at 4° C. Subsequently, each well is washed three times with 0.1% BSA/TBS-T, and 70 µL of a solution of a horseradish peroxidase-labeled anti-mouse IgG antibody obtained by diluting the antibody to 2000 times with 1% BSA/TBS-T is added to each well, and then, the plate is let stand at room temperature for 3 hours. Finally, each well is washed five times with 0.1% BSA/TBS-T, and 100 µL of Sure Blue Reserve TMB peroxidase substrate is added to each well, and a chromogenic reaction is allowed to proceed for 10 minutes in a dark place at room temperature. Thereafter, 100 µL of 1 M hydrochloric acid is added to each well to stop the reaction, and measurement is carried out by the colorimetric method.

As shown in Table 2, the compounds according to the invention exhibit an excellent inhibitory effect on Cdc2 tyrosine-15 phosphorylation against human-derived cancer cell lines.

TABLE 2

| Example | Inhibitory effect on Cdc2 tyrosine-15 phosphorylation (IC50, nM) |
|---|---|
| 1 | 87 |
| 2 | 79 |
| 3 | 45 |
| 4 | 33 |

Subsequently, a checkpoint abrogating effect of the compound of the general formula (I) according to the invention on cells will be described below.

Pharmacological Test 3 (Method for Determining Drug Effect Using Cells (Checkpoint Abrogating Effect))

a) Reagents

Fetal bovine serum (FBS) can be obtained from Morgate, Inc.; a DMEM medium can be obtained from Invitrogen, Inc.; gemcitabine can be obtained from Eli Lilly Japan K.K.; nocodazole and 4',6-diamidino-2-phenylindole can be obtained from Sigma Co.; a rabbit anti-phosphorylated histone H3 antibody can be obtained from Upstate, Inc.; and an anti-rabbit IgG antibody fluorescently labeled with Alexa Fluor 488 can be obtained from Molecular Probe, Inc.

b) Cells

A human colon cancer cell line (WiDr) can be obtained from American Type Culture Collection (ATCC).

c) Method for Determining Effect

The cells are suspended in a DMEM medium supplemented with 10% FBS, and 100 µL of the resulting cell suspension is dispensed in a poly-D-lysine coated 96-well plastic plate purchased from Becton, Dickinson and Company at a density of 2000 cells per well, and the plate is incubated overnight at 37° C. under an atmosphere of 5% $CO_2$ and 95% air. Gemcitabine is dissolved in phosphate buffered saline (PBS) and further the resulting solution is diluted with a DMEM medium supplemented with 10% FBS. Then, 50 µL of the diluted solution is added to each well of the plate in which the cells have been seeded in advance such that the final concentration of gemcitabine is 100 nM, and the plate is incubated at 37° C. under an atmosphere of 5% $CO_2$ and 95% air for 24 hours. A test compound is serially diluted with dimethyl sulfoxide, and further diluted with a DMEM medium supplemented with 10% FBS containing 1200 nM nocodazole. Then, 50 µL of the test compound solution is added to each well of the plate in which the cells treated with gemcitabine have been seeded, and the plate is incubated at 37° C. under an atmosphere of 5% $CO_2$ and 95% air for 8 hours. Then, the culture medium is removed from each well and 100 µL of methanol previously chilled to −20° C. is added to each well, and the plate is let stand overnight at −20° C. to fix the cells. Thereafter, the cells fixed with methanol are washed PBS, and 50 µL of PBS containing 1% bovine serum albumin (1% BSA/PBS) is added to each well, and then, the plate is let stand at room temperature for 30 minutes. Thereafter, 50 µL of a solution of a rabbit anti-phosphorylated histone H3 antibody obtained by diluting the antibody to 250 times with 1% BSA/PBS is added to each well, and then, the plate is let stand at room temperature for 90 minutes. Then, after the cells are washed with PBS, 50 µL of a solution containing 4',6-diamidino-2-phenylindole diluted to 10 µg/mL with 1% BSA/PBS and an anti-rabbit IgG antibody fluorescently labeled with Alexa Fluor 488 diluted to 250 times with 1% BSA/PBS is added to each well and a reaction is allowed to proceed for 60 minutes in a dark place at room temperature. Finally, after the cells are washed with PBS, the fluorescence intensity is measured. Then, a ratio of phosphorylated histone H3 positive cells (cells which proceed to cell division phase by abrogating checkpoint) is calculated to determine a 50% effective concentration ($EC_{50}$, nM) of the test compound for checkpoint abrogation in cells.

As described above, an excellent checkpoint abrogating effect of the compound according to the invention on human-derived cancer cells (WiDr) can be determined.

Pharmacological Test 4 (Inhibitory Effect on Tumor Growth)

A human colon cancer cell line WiDr (obtained from ATCC) is implanted into the subcutaneous area of the back of F344/N Jc1-rnu nude rats. 12 days after the implantation, gemcitabine (Gemzar injection, Eli Lilly and Company) is intravenously administered to the rats at a dose of 5 mg/kg. At 24 hours thereafter, a test compound is suspended in a solvent (0.5% methyl cellulose) and orally administered to the rats. This procedure is repeated once a week for 3 weeks. A tumor volume (0.5×(major diameter)×(minor diameter)$^2$) is measured on days 0, 3, 6, 10, 13, 17, 20, 24 and 27. Day 0 means the day on which gemcitabine is first administered. A relative tumor volume is calculated based on the tumor volume on day 0 the value of which is taken as 1. Further, a tumor growth ratio (% T/C) is calculated from the following equation.

In the case where a change in tumor volume from day 0 in the test compound administration group is more than 0 (>0):

% T/C=[(a change in tumor volume in each test compound group on day 3, 6, 10, 13, 17, 20, 24 or 27)/(a change in tumor volume in the control group on day 3, 6, 10, 13, 17, 20, 24 or 27)]×100.

In the case where a change in tumor volume from day 0 in the test compound administration group is less than 0 (<0):

% T/C=[(a change in tumor volume in each test compound group on day 3, 6, 10, 13, 17, 20, 24 or 27)/(tumor volume in each test compound group on day 0)]×100.

As described above, it can be determined that the compound of the invention potentiates the effect of any other anticancer agents by using the compound of the invention in combination with the anticancer agent.

Pharmacological Test 5 (Method for Determining Drug Effect Using Cells (Radiation (X-Ray) Sensitizing Effect))

a) Reagents

Fetal bovine serum (FBS) can be obtained from Morgate, Inc.; an RPMI 1640 medium and 0.25% trypsin EDTA can be obtained from Invitrogen, Inc.; a cycle test plus DNA reagent kit can be obtained from Becton, Dickinson and Company; and a nylon net filter can be obtained from Millipore, Inc.

b) Cells

A human non-small cell lung cancer cell line (NCI-H1299) can be obtained from ATCC.

c) Method for Determining Effect

NCI-H1299 cells are suspended in an RPMI-1640 medium supplemented with 10% FBS, and 2 mL of the resulting cell suspension is dispensed in a Nunclon Delta treated 6-well plastic plate purchased from Nunc, Inc. at a density of 100000 cells per well, and the plate is incubated overnight at 37° C. under an atmosphere of 5% $CO_2$ and 95% air. The cells are irradiated with 5000 R X-ray using M-150 WE available from Softex, and then, the plate is further incubated for 16 hours at 37° C. under an atmosphere of 5% $CO_2$ and 95% air. A test compound is serially diluted with DMSO and 2 µL of the test compound solution is added to each well of the plate in which the cells treated with X-rays have been seeded in advance. Then, after the plate is incubated for 8 hours at 37° C. under an atmosphere of 5% $CO_2$ and 95% air, the culture medium is taken out and kept as a part of each sample, and the cells remaining in the plate is suspended by adding 600 µL of 0.25% trypsin to each well and letting the suspension stand at room temperature to prepare a single cell suspension. The thus obtained single cell suspension and the previously taken culture medium are mixed for each sample, and then, the resulting mixture is centrifuged and the supernatant is removed. Sampling is thus completed. The thus obtained sample is suspended in 1 mL of a buffer in a cycle test plus DNA reagent kit and the resulting suspension is cryopreserved at −80° C. The cryopreserved sample is thawed on the test date and centrifuged and the supernatant is removed. Then, the residue is suspended in 250 µL of a solution in the cycle test plus and the resulting suspension is let stand at room temperature for 10 minutes, and then 150 µL of B solution is added thereto, and the resulting mixture is further let stand at room temperature for 10 minutes. Subsequently, 150 µL of C solution is added thereto, and the resulting mixture is let stand at 4° C. for 10 minutes, and then filtered through a nylon net filter thereby completing staining of DNA. The DNA amount in each cell is quantitatively determined by the FACS method using FACS Calibur available from Becton, Dickinson and Company, and a ratio of cells having caused DNA fragmentation is determined.

As described above, an excellent DNA fragmentation inducing effect of the compound of the invention on a human-derived cancer cell line (NCI-H1299) can be determined and the X-ray sensitizing effect of the compound of the invention can be determined.

The compound represented by the general formula (I) can be administered orally or parenterally, and by formulating the compound into a preparation suitable for such an administration route, the compound can be used as a pharmaceutical composition or an anticancer agent.

The term "cancer" as used herein includes various sarcomas and carcinomas and includes solid cancers and hematopoietic cancers. Here, the solid cancers include, for example, brain tumor, head and neck cancer, esophageal cancer, thyroid cancer, small cell cancer, non-small cell cancer, breast cancer, lung cancer, stomach cancer, gallbladder and bile duct cancer, liver cancer, pancreatic cancer, colon cancer, rectal cancer, ovarian cancer, chorioepithelioma, endometrial cancer, cervical cancer, renal pelvic and ureteral cancer, bladder cancer, prostate cancer, penile cancer, testicular cancer, embryonal carcinoma, Wilms' tumor, skin cancer, malignant melanoma, neuroblastoma, osteosarcoma, Ewing's tumor, soft tissue sarcoma and the like. On the other hand, the hematopoietic cancers include, for example, acute leukemia, chronic lymphocytic leukemia, chronic myeloid leukemia, polycythemia vera, malignant lymphoma, multiple myeloma, Hodgkin's lymphoma, non-Hodgkin's lymphoma and the like.

The term "treatment of cancer" as used herein means that an anticancer agent is administered to a cancer patient so as to inhibit the growth of the cancer cells. Preferably, the treatment enables the regression of cancer growth, i.e., the reduction of the size of detectable cancer. More preferably, the treatment eradicates cancer completely.

Preferred examples of the cancer on which the therapeutic effect of the compound according to the invention is expected include human solid cancers. Examples of the human solid cancers include brain tumor, head and neck cancer, esophageal cancer, thyroid cancer, small cell cancer, non-small cell cancer, breast cancer, lung cancer, stomach cancer, gallbladder and bile duct cancer, liver cancer, pancreatic cancer, colon cancer, rectal cancer, ovarian cancer, chorioepithelioma, endometrial cancer, cervical cancer, renal pelvic and ureteral cancer, bladder cancer, prostate cancer, penile cancer, testicular cancer, embryonal carcinoma, Wilms' tumor, skin cancer, malignant melanoma, neuroblastoma, osteosarcoma, Ewing's tumor, soft tissue sarcoma, acute leukemia, chronic lymphocytic leukemia, chronic myeloid leukemia and Hodgkin's lymphoma.

The pharmaceutical composition or anticancer agent according to the invention may contain a pharmaceutically acceptable carrier or diluent. Here, the "pharmaceutically acceptable carrier or diluent" means an excipient (for example, a fat, beeswax, a semi-solid or liquid polyol, a natural or hydrogenated oil, etc.); water (for example, distilled water, particularly distilled water for injection, etc.), physiological saline, an alcohol (for example, ethanol), glycerol, a polyol, an aqueous glucose solution, mannitol, a vegetable oil, etc.; an additive (for example, an expander, a disintegrant, a binder, a lubricant, a wetting agent, a stabilizer, an emulsifier, a dispersant, a preservative, a sweetener, a colorant, a seasoning agent or a flavor, a thickening agent, a diluent, a buffer substance, a solvent or a solubilizing agent, a chemical for providing a storage effect, a salt for changing osmotic pressure, a coating agent or an antioxidant) or the like.

The preparation related to the pharmaceutical composition or anticancer agent of the invention can have any of various dosage forms, and examples thereof include oral preparations such as tablets, capsules, powders, granules and liquids, sterilized liquid parenteral preparations such as solutions and suspensions, suppositories and ointments.

A solid preparation can be prepared in the form of a tablet, a capsule, a granule or a powder as such, or can be prepared using an appropriate carrier (additive). Examples of such carrier (additive) include saccharides such as lactose and glucose; starches of corn, wheat and rice; fatty acids such as stearic acid; inorganic salts such as magnesium metasilicate aluminate and anhydrous calcium phosphate; synthetic polymers such as polyvinylpyrrolidone and polyalkylene glycol; fatty acid salts such as calcium stearate and magnesium stearate; alcohols such as stearyl alcohol and benzyl alcohol; synthetic cellulose derivatives such as methyl cellulose, carboxymethyl cellulose, ethyl cellulose and hydroxypropyl methyl cellulose; and other conventionally used additives such as gelatin, talc, vegetable oils and gum arabic.

These solid preparations such as tablets, capsules, granules and powders may generally contain, as an active ingredient, for example, 0.1 to 100% by weight, preferably 5 to 98% by weight of the compound represented by the above-mentioned formula (I) based on the total weight of the preparation.

A liquid preparation is produced in the form of a suspension, a syrup, an injection or a drip infusion (intravenous infusion) using an appropriate additive which is conventionally used in a liquid preparation such as water, an alcohol or a plant-derived oil such as soybean oil, peanut oil or sesame oil.

In particular, as an appropriate solvent or diluent when the preparation is administered parenterally in the form of an intramuscular injection, an intravenous injection or a subcutaneous injection, distilled water for injection, an aqueous solution of lidocaine hydrochloride (for intramuscular injection), physiological saline, an aqueous glucose solution, ethanol, polyethylene glycol, propylene glycol, a liquid for intravenous injection (for example, an aqueous solution of citric acid, sodium citrate or the like) or an electrolytic solution (for intravenous drip infusion or intravenous injection), or a mixed solution thereof can be exemplified.

Such an injection may be also in the form of a preliminarily dissolved solution, or in the form of a powder per se or a powder with the addition of a suitable carrier (additive) which is dissolved at the time of use. The injection liquid can contain, for example, 0.1 to 10% by weight of an active ingredient based on the total weight of the preparation.

The liquid preparation such as a suspension or a syrup for oral administration can contain, for example, 0.1 to 10% by weight of an active ingredient based on the total weight of the preparation.

Such a preparation can be easily produced by a person skilled in the art according to a common procedure or a conventional technique. For example, in the case of an oral preparation, it can be produced by, for example, mixing an appropriate amount of the compound of the invention with an appropriate amount of lactose and filling this mixture into a hard gelatin capsule suitable for oral administration. On the other hand, in the case where the preparation containing the compound of the invention is an injection, it can be produced by, for example, mixing an appropriate amount of the compound of the invention with an appropriate amount of 0.9% physiological saline and filling this mixture in a vial for injection.

The compound of the invention can be used by combining it with any other agent useful for treatment of various cancers or with radiotherapy. The individual ingredients in the case of such a combination can be administered at different times or at the same time as divided preparations or a single preparation during the period of treatment. Accordingly, the invention should be so interpreted that it includes all modes of administration at the same time or at different times, and the administration in the invention should be interpreted so. The scope of the combination of the compound of the invention with any other agent useful for the treatment of the above-mentioned diseases should include, in principle, every combination thereof with every pharmaceutical preparation useful for the treatment of the above-mentioned diseases.

The radiation therapy itself means an ordinary method in the field of treatment of cancer. In the radiation therapy, any of various radiations such as an X-ray, a γ-ray, a neutron ray, an electron beam and a proton beam, and radiation sources is used. The most common radiation therapy is one which is carried out by external radiation using a linear accelerator, and in which a γ-ray is irradiated.

The compound of the invention can potentiate the therapeutic effect of the radiation therapy by combining the compound of the invention with the radiation therapy and therefore can be useful as a radiation sensitizer in the field of treatment of cancer.

Another aspect of the compound of the invention is that the compound of the invention is also useful as a sensitizer for any other anticancer agents in the field of treatment of cancer.

The compound of the invention can be used by combining it with radiation therapy and/or any other anticancer agents described below.

The "sensitizer" of radiation or for an anticancer agent as used herein means a medicinal agent which, when it is used by combining it with radiation therapy and/or chemotherapy using an anticancer agent, additively or synergistically potentiates the therapeutic effect of the radiation therapy and/or chemotherapy in the field of treatment of cancer.

The respective preparations in the combined preparation according to the invention can have any form, and they can be produced in the same manner as that for the above-mentioned preparation. A drug combination containing the compound of the invention and any other anticancer agents can also be easily produced by a person skilled in the art according to a common procedure or a conventional technique.

The above-mentioned combination includes a combination of the composition of the invention not only with one other active substance but also with two or more other active substances. There are a lot of examples of the combination of the composition of the invention with one or two or more active substances selected from the therapeutic agents for the above-mentioned diseases.

The agents to be combined with the compositions include, for example, an anticancer agent selected from the group consisting of anticancer alkylating agents, anticancer antimetabolites, anticancer antibiotics, plant-derived anticancer agents, anticancer platinum coordination compounds, anticancer camptothecin derivatives, anticancer tyrosine kinase inhibitors, monoclonal antibodies, interferons, biological response modifiers and other anticancer agents as well as pharmaceutically acceptable salt(s) or ester(s) thereof.

The term "anticancer alkylating agent" as used in the present specification refers to an alkylating agent having anticancer activity, and the term "alkylating agent" herein generally refers to an agent giving an alkyl group in the alkylation reaction in which a hydrogen atom of an organic compound is substituted with an alkyl group. The term "anticancer alkylating agent" may be exemplified by nitrogen mustard N-oxide, cyclophosphamide, ifosfamide, melphalan, busulfan, mitobronitol, carboquone, thiotepa, ranimustine, nimustine, temozolomide or carmustine.

The term "anticancer antimetabolite" as used in the specification refers to an antimetabolite having anticancer activity, and the term "antimetabolite" herein includes, in a broad sense, substances which disturb normal metabolism and substances which inhibit the electron transfer system to prevent the production of energy-rich intermediates, due to their structural or functional similarities to metabolites that are important for living organisms (such as vitamins, coenzymes, amino acids and saccharides). The term "anticancer antimetabolites" may be exemplified methotrexate, 6-mercaptopurine riboside, mercaptopurine, 5-fluorouracil, tegafur, doxifluridine, carmofur, cytarabine, cytarabine ocfosfate, enocitabine, S-1, gemcitabine, fludarabine or pemetrexed disodium, and preferred are cytarabine, gemcitabine and the like.

The term "anticancer antibiotic" as used in the specification refers to an antibiotic having anticancer activity, and the "antibiotic" herein includes substances that are produced by microorganisms and inhibit cell growth and other functions of microorganisms and of other living organisms. The term "anticancer antibiotic" may be exemplified by actinomycin D, doxorubicin, daunorubicin, neocarzinostatin, bleomycin, peplomycin, mitomycin C, aclarubicin, pirarubicin, epirubicin, zinostatin stimalamer, idarubicin, sirolimus or valrubicin, and preferred are doxorubicin, mitomycin C and the like.

The term "plant-derived anticancer agent" as used in the specification includes compounds having anticancer activities which originate from plants, or compounds prepared by applying chemical modification to the foregoing compounds. The term "plant-derived anticancer agent" may be exemplified by vincristine, vinblastine, vindesine, etoposide, sobuzoxane, docetaxel, paclitaxel and vinorelbine, and preferred are etoposide and the like.

The term "anticancer camptothecin derivative" as used in the specification refers to compounds that are structurally related to camptothecin and inhibit cancer cell growth, including camptothecin per se. The term "anticancer camptothecin derivative" is not particularly limited to, but may be exemplified by, camptothecin, 10-hydroxycamptothecin, topotecan, irinotecan or 9-aminocamptothecin, with camptothecin being preferred. Further, irinotecan is metabolized in vivo and exhibits anticancer effect as SN-38. The action mechanism and the activity of the camptothecin derivatives are believed to be virtually the same as those of camptothecin (e.g., Nitta, et al., *Gan to Kagaku Ryoho*, 14, 850-857 (1987)).

The term "anticancer platinum coordination compound" as used in the specification refers to a platinum coordination compound having anticancer activity, and the term "platinum coordination compound" herein refers to a platinum coordination compound which provides platinum in ion form. Preferred platinum compounds include cisplatin; cis-diamminediaquoplatinum (II)-ion; chloro(diethylenetriamine)-platinum (II) chloride; dichloro(ethylenediamine)-platinum (II); diammine(1,1-cyclobutanedicarboxylato) platinum (II) (carboplatin); spiroplatin; iproplatin; diammine(2-ethylmalonato)platinum (II); ethylenediaminemalonatoplatinum (II); aqua(1,2-diaminodicyclohexane)sulfatoplatinum (II); aqua (1,2-diaminodicyclohexane)malonatoplatinum (II); (1,2-diaminocyclohexane)malonatoplatinum (II); (4-carboxyphthalato)(1,2-diaminocyclohexane) platinum (II); (1,2-diaminocyclohexane)-(isocitrato)platinum (1); (1,2-diaminocyclohexane)oxalatoplatinum (II); ormaplatin; tetraplatin; carboplatin, nedaplatin and oxaliplatin, and preferred is carboplatin or cisplatin. Further, other anticancer platinum coordination compounds mentioned in the specification are known and are commercially available and/or producible by a person having ordinary skill in the art by conventional techniques.

The term "anticancer tyrosine kinase inhibitor" as used in the specification refers to a tyrosine kinase inhibitor having anticancer activity, and the term "tyrosine kinase inhibitor" herein refers to a chemical substance inhibiting "tyrosine kinase" which transfers a γ-phosphate group of ATP to a hydroxyl group of a specific tyrosine in protein. The term "anticancer tyrosine kinase inhibitor" may be exemplified by gefitinib, imatinib or erlotinib.

The term "monoclonal antibody" as used in the specification, which is also known as single clonal antibody, refers to an antibody produced by a monoclonal antibody-producing cell, and examples thereof include cetuximab, bevacizumab, rituximab, alemtuzumab and trastuzumab.

The term "interferon" as used in the specification refers to an interferon having anticancer activity, and it is a glycoprotein having a molecular weight of about 20,000 which is produced and secreted by most animal cells upon viral infection. It has not only the effect of inhibiting viral growth but also various immune effector mechanisms including inhibition of growth of cells (in particular, tumor cells) and enhancement of the natural killer cell activity, thus being designated as one type of cytokine. Examples of "interferon" include interferon α, interferon α-2a, interferon α-2b, interferon β, interferon γ-1a and interferon γ-n1.

The term "biological response modifier" as used in the specification is the so-called biological response modifier or BRM and is generally the generic term for substances or drugs for modifying the defense mechanisms of living organisms or biological responses such as survival, growth or differentiation of tissue cells in order to direct them to be useful for an individual against tumor, infection or other diseases. Examples of the "biological response modifier" include krestin, lentinan, sizofuran, picibanil and ubenimex.

The term "other anticancer agent" as used in the specification refers to an anticancer agent which does not belong to any of the above-described agents having anticancer activities. Examples of the "other anticancer agent" include mitoxantrone, L-asparaginase, procarbazine, dacarbazine, hydroxycarbamide, pentostatin, tretinoin, alefacept, darbepoetin alfa, anastrozole, exemestane, bicalutamide, leuprorelin, flutamide, fulvestrant, pegaptanib octasodium, denileukin diftitox, aldesleukin, thyrotropin alfa, arsenic trioxide, bortezomib, capecitabine, and goserelin.

The above-described terms "anticancer alkylating agent", "anticancer antimetabolite", "anticancer antibiotic", "plant-derived anticancer agent", "anticancer platinum coordination compound", "anticancer camptothecin derivative", "anticancer tyrosine kinase inhibitor", "monoclonal antibody", "interferon", "biological response modifier" and "other anticancer agent" are all known and are either commercially available or producible by a person skilled in the art by methods known per se or by well-known or conventional methods. The process for preparation of gefitinib is described, for example, in U.S. Pat. No. 5,770,599; the process for preparation of cetuximab is described, for example, in WO 96/40210; the process for preparation of bevacizumab is described, for example, in WO 94/10202; the process for preparation of oxaliplatin is described, for example, in U.S. Pat. Nos. 5,420,319 and 5,959,133; the process for preparation of gemcitabine is described, for example, in U.S. Pat. Nos. 5,434,254 and 5,223,608; and the process for preparation of camptothecin is described in U.S. Pat. Nos. 5,162,532, 5,247,089, 5,191,082, 5,200,524, 5,243,050 and 5,321,140; the process for preparation of irinotecan is described, for example, in U.S. Pat. No. 4,604,463; the process for preparation of topotecan is described, for example, in U.S. Pat. No. 5,734,056; the process for preparation of temozolomide is described, for example, in JP-B No. 4-5029; and the process for preparation of rituximab is described, for example, in JP-W No. 2-503143.

The above-mentioned anticancer alkylating agents are commercially available, as exemplified by the following: nitrogen mustard N-oxide from Mitsubishi Pharma Corp. as Nitromin (tradename); cyclophosphamide from Shionogi & Co., Ltd. as Endoxan (tradename); ifosfamide from Shionogi & Co., Ltd. as Ifomide (tradename); melphalan from GlaxoSmithKline Corp. as Alkeran (tradename); busulfan from Takeda Pharmaceutical Co., Ltd. as Mablin (tradename); mitobronitol from Kyorin Pharmaceutical Co., Ltd. as Myebrol (tradename); carboquone from Sankyo Co., Ltd. as Esquinon (tradename); thiotepa from Sumitomo Pharmaceutical Co., Ltd. as Tespamin (tradename); ranimustine from Mitsubishi Pharma Corp. as Cymerin (tradename); nimustine from Sankyo Co., Ltd. as Nidran (tradename); temozolomide from Schering Corp. as Temodar (tradename); and carmustine from Guilford Pharmaceuticals Inc. as Gliadel Wafer (tradename).

The above-mentioned anticancer antimetabolites are commercially available, as exemplified by the following: methotrexate from Takeda Pharmaceutical Co., Ltd. as Methotrexate (tradename); 6-mercaptopurine riboside from Aventis Corp. as Thioinosine (tradename); mercaptopurine from Takeda Pharmaceutical Co., Ltd. as Leukerin (tradename); 5-fluorouracil from Kyowa Hakko Kogyo Co., Ltd. as 5-FU (tradename); tegafur from Taiho Pharmaceutical Co., Ltd. as Futraful (tradename); doxyfluridine from Nippon Roche Co., Ltd. as Furutulon (tradename); carmofur from Yamanouchi Pharmaceutical Co., Ltd. as Yamafur (tradename); cytarabine from Nippon Shinyaku Co., Ltd. as Cylocide (tradename); cytarabine ocfosfate from Nippon Kayaku Co., Ltd. as Strasid (tradename); enocitabine from Asahi Kasei Corp. as Sanrabin (tradename); S-1 from Taiho Pharmaceutical Co., Ltd. as TS-1 (tradename); gemcitabine from Eli Lilly & Co. as Gemzar (tradename); fludarabine from Nippon Schering Co., Ltd. as Fludara (tradename); and pemetrexed disodium from Eli Lilly & Co. as Alimta (tradename).

The above-mentioned anticancer antibiotics are commercially available, as exemplified by the following: actinomycin D from Banyu Pharmaceutical Co., Ltd. as Cosmegen (tradename); doxorubicin from Kyowa Hakko Kogyo Co., Ltd. as Adriacin (tradename); daunorubicin from Meiji Seika Kaisha Ltd. as Daunomycin; neocarzinostatin from Yamanouchi Pharmaceutical Co., Ltd. as Neocarzinostatin (tradename); bleomycin from Nippon Kayaku Co., Ltd. as Bleo (tradename); pepromycin from Nippon Kayaku Co, Ltd. as Pepro (tradename); mitomycin C from Kyowa Hakko Kogyo Co., Ltd. as Mitomycin (tradename); aclarubicin from Yamanouchi Pharmaceutical Co., Ltd. as Aclacinon (tradename); pirarubicin from Nippon Kayaku Co., Ltd. as Pinorubicin (tradename); epirubicin from Pharmacia Corp. as Pharmorubicin (tradename); zinostatin stimalamer from Yamanouchi Pharmaceutical Co., Ltd. as Smancs (tradename); idarubicin from Pharmacia Corp. as Idamycin (tradename); sirolimus from Wyeth Corp. as Rapamune (tradename); and valrubicin from Anthra Pharmaceuticals Inc. as Valstar (tradename).

The above-mentioned plant-derived anticancer agents are commercially available, as exemplified by the following: vincristine from Shionogi & Co., Ltd. as Oncovin (tradename); vinblastine from Kyorin Pharmaceutical Co., Ltd. as Vinblastine (tradename); vindesine from Shionogi & Co., Ltd. as Fildesin (tradename); etoposide from Nippon Kayaku Co., Ltd. as Lastet (tradename); sobuzoxane from Zenyaku Kogyo Co., Ltd. as Perazolin (tradename); docetaxel from Aventis Corp. as Taxsotere (tradename); paclitaxel from Bristol-Myers Squibb Co. as Taxol (tradename); and vinorelbine from Kyowa Hakko Kogyo Co., Ltd. as Navelbine (tradename).

The above-mentioned anticancer platinum coordination compounds are commercially available, as exemplified by the following: cisplatin from Nippon Kayaku Co., Ltd. as Randa (tradename); carboplatin from Bristol-Myers Squibb Co. as Paraplatin (tradename); nedaplatin from Shionogi & Co., Ltd. as Aqupla (tradename); and oxaliplatin from Sanofi-Synthelabo Co. as Eloxatin (tradename).

The above-mentioned anticancer camptothecin derivatives are commercially available, as exemplified by the following: irinotecan from Yakult Honsha Co., Ltd. as Campto (tradename); topotecan from GlaxoSmithKline Corp. as Hycamtin (tradename); and camptothecin from Aldrich Chemical Co., Inc., U.S.A.

The above-mentioned anticancer tyrosine kinase inhibitors are commercially available, as exemplified by the following: gefitinib from AstraZeneca Corp. as Iressa (tradename); imatinib from Novartis AG as Gleevec (tradename); and erlotinib from OSI Pharmaceuticals Inc. as Tarceva (tradename).

The above-mentioned monoclonal antibodies are commercially available, as exemplified by the following: cetuximab from Bristol-Myers Squibb Co. as Erbitux (tradename); bevacizumab from Genentech, Inc. as Avastin (tradename); rituximab from Biogen Idec Inc. as Rituxan (tradename); alemtuzumab from Berlex Inc. as Campath (tradename); and trastuzumab from Chugai Pharmaceutical Co., Ltd. as Herceptin (tradename).

The above-mentioned interferons are commercially available, as exemplified by the following: interferon α from Sumitomo Pharmaceutical Co., Ltd. as Sumiferon (tradename); interferon α-2a from Takeda Pharmaceutical Co., Ltd. as Canferon-A (tradename); interferon α-2b from Schering-Plough Corp. as Intron A (tradename); interferon β from Mochida Pharmaceutical Co., Ltd. as IFNβ (tradename); interferon γ-1a from Shionogi & Co., Ltd. as Immunomax-γ (tradename); and interferon γ-n1 from Otsuka Pharmaceutical Co., Ltd. as Ogamma (tradename).

The above-mentioned biological response modifiers are commercially available, as exemplified by the following: krestin from Sankyo Co., Ltd. as Krestin (tradename); lentinan from Aventis Corp. as Lentinan (tradename); sizofuran from Kaken Seiyaku Co., Ltd. as Sonifuran (tradename); picibanil from Chugai Pharmaceutical Co., Ltd. as Picibanil (tradename); and ubenimex from Nippon Kayaku Co., Ltd. as Bestatin (tradename).

The above-mentioned other anticancer agents are commercially available, as exemplified by the following: mitoxantrone from Wyeth Lederle Japan, Ltd. as Novantrone (tradename); L-asparaginase from Kyowa Hakko Kogyo Co., Ltd. as Leunase (tradename); procarbazine from Nippon Roche Co., Ltd. as Natulan (tradename); dacarbazine from Kyowa Hakko Kogyo Co., Ltd. as Dacarbazine (tradename); hydroxycarbamide from Bristol-Myers Squibb Co. as Hydrea (tradename); pentostatin from Kagaku Oyobi Kessei Ryoho Kenkyusho as Coforin (tradename); tretinoin from Nippon Roche Co., Ltd. As Vesanoid (tradename); alefacept from Biogen Idec Inc. as Amevive (tradename); darbepoetin alfa from Amgen Inc. as Aranesp (tradename); anastrozole from AstraZeneca Corp. as Arimidex (tradename); exemestane from Pfizer Inc. as Aromasin (tradename); bicalutamide from AstraZeneca Corp. as Casodex (tradename); leuprorelin from Takeda Pharmaceutical Co., Ltd. as Leuplin (tradename); flutamide from Schering-Plough Corp. as Eulexin (tradename); fulvestrant from AstraZeneca Corp. as Faslodex (tradename); pegaptanib octasodium from Gilead Sciences, Inc. as Macugen (tradename); denileukin diftitox from Ligand Pharmaceuticals Inc. as Ontak (tradename); aldesleukin from Chiron Corp. as Proleukin (tradename); thyrotropin alfa from Genzyme Corp. as Thyrogen (tradename); arsenic trioxide from Cell Therapeutics, Inc. as Trisenox (tradename); bortezomib from Millennium Pharmaceuticals, Inc. as Velcade (tradename); capecitabine from Hoffmann-La Roche, Ltd. as Xeloda (tradename); and goserelin from AstraZeneca Corp. as Zoladex (tradename).

The invention also relates to a method for the treatment of cancer, which comprises administering to a subject in need thereof a therapeutically-effective amount of the compound of the invention or a pharmaceutically acceptable salt or ester thereof.

In the process according to the invention, preferred therapeutic unit may vary in accordance with, for example, the administration route of the compound of the invention, the type of the compound of the invention used, and the dosage form of the compound of the invention used; the type, administration route and dosage form of the other anticancer agent used in combination; and the type of cells to be treated, the condition of patient, and the like. The optimal treatment under the given conditions can be determined by a person skilled in the art, based on the set conventional therapeutic unit and/or based on the content of the present specification.

In the process according to the invention, the therapeutic unit for the compound of the invention may vary in accordance with, specifically, the type of compound used, the type of compounded composition, application frequency and the specific site to be treated, seriousness of the disease, age of the patient, doctor's diagnosis, the type of cancer, or the like. However, as an exemplary reference, the daily dose for an adult may be within a range of, for example, 1 to 1,000 mg in the case of oral administration. In the case of parenteral administration, preferably intravenous administration, and more preferably intravenous drip infusion, the daily dose may be within a range of, for example, 1 to 100 mg/m$^2$ (body surface area). Here, in the case of intravenous drip infusion, administration may be continuously carried out for, for example, 1 to 48 hours. Moreover, the administration frequency may vary depending on the administering method and symptoms, but it is, for example, once to five times a day. Alternatively, periodically intermittent administration such as administration every other day, administration every two days or the like may be employed as well in the administering method. The period of withdraw from medication in the case of parenteral administration is, for example, 1 to 6 weeks.

Although the therapeutic unit for the other anticancer agent used in combination with the compound of the invention is not particularly limited, it can be determined, if needed, by those skilled in the art according to known literatures. Examples may be as follows.

The therapeutic unit of 5-fluorouracil (5-FU) is such that, in the case of oral administration, for example, 200 to 300 mg per day is administered in once to three times consecutively, and in the case of injection, for example, 5 to 15 mg/kg per day is administered once a day for the first 5 consecutive days by intravenous injection or intravenous drip infusion, and then 5 to 7.5 mg/kg is administered once a day every other day by intravenous injection or intravenous drip infusion (the dose may be appropriately increased or decreased).

The therapeutic unit of S-1 (Tegafur, Gimestat and Ostat potassium) is such that, for example, the initial dose (singe dose) is set to the following standard amount in accordance with the body surface area, and it is orally administered twice a day, after breakfast and after dinner, for 28 consecutive days, followed by withdrawal from medication for 14 days. This is set as one course of administration, which is repeated. The initial standard amount per unit body surface area (Tegafur equivalent) is 40 mg in one administration for an area less than 1.25 m$^2$; 50 mg in one administration for an area of 1.25 m$^2$ to less than 1.5 m$^2$; 60 mg in one administration for an area of 1.5 m$^2$ or more. This dose is appropriately increased or decreased depending on the condition of the patient.

The therapeutic unit for gemcitabine is, for example, 1 g as gemcitabine/m$^2$ in one administration, which is administered by intravenous drip infusion over a period of 30 minutes, and one administration per week is continued for 3 weeks, followed by withdrawal from medication on the fourth week. This is set as one course of administration, which is repeated. The dose is appropriately decreased in accordance with age, symptom or development of side-effects.

The therapeutic unit for doxorubicin (e.g., doxorubicin hydrochloride) is such that, for example, in the case of intravenous injection, 10 mg (0.2 mg/kg) (titer) is administered once a day by intravenous one-shot administration for 4 to 6 consecutive days, followed by withdrawal from medication for 7 to 10 days. This is set as one course of administration, which is repeated two or three times. Here, the total dose is preferably 500 mg (titer)/m$^2$ (body surface area) or less, and it may be appropriately increased or decreased within the range.

The therapeutic unit for etoposide is such that, for example, in the case of intravenous injection, 60 to 100 mg/m$^2$ (body surface area) per day is administered for 5 consecutive days, followed by withdrawal from medication for three weeks (the dose may be appropriately increased or decreased). This is set as one course of administration, which is repeated. Meanwhile, in the case of oral administration, for example, 175 to 200 mg per day is administered for 5 consecutive days, followed by withdrawal from medication for three weeks (the dose may be appropriately increased or decreased). This is set as one course of administration, which is repeated.

The therapeutic unit for docetaxel (docetaxel hydrate) is such that, for example, 60 mg as docetaxel/m$^2$ (body surface area) is administered once a day by intravenous drip infusion over a period of 1 hour or longer at an interval of 3 to 4 weeks (the dose may be appropriately increased or decreased).

The therapeutic unit of paclitaxel is such that, for example, 210 mg/m$^2$ (body surface area) is administered once a day by intravenous drip infusion over a period of 3 hours, followed by withdrawal from medication for at least 3 weeks. This is set as one course of administration, which is repeated. The dose may be appropriately increased or decreased.

The therapeutic unit for cisplatin is such that, for example, in the case of intravenous injection, 50 to 70 mg/m$^2$ (body surface area) is administered once a day, followed by withdrawal from medication for 3 weeks or longer (the dose may be appropriately increased or decreased). This is set as one course of administration, which is repeated.

The therapeutic unit for carboplatin is such that, for example, 300 to 400 mg/m$^2$ is administered once a day by intravenous drip infusion over a period of 30 minutes or longer, followed by withdrawal from medication for at least 4 weeks (the dose may be appropriately increased or decreased). This is set as one course of administration, which is repeated.

The therapeutic unit for oxaliplatin is such that 85 mg/m$^2$ is administered once a day by intravenous injection, followed by withdrawal from medication for two weeks. This is set as one course of administration, which is repeated.

The therapeutic unit for irinotecan (e.g., irinotecan hydrochloride) is such that, for example, 100 mg/m$^2$ is administered once a day by intravenous drip infusion for 3 or 4 times at an interval of one week, followed by withdrawal from medication for at least two weeks.

The therapeutic unit for topotecan is such that, for example, 1.5 mg/m$^2$ is administered once a day by intravenous drip infusion for 5 days, followed by withdrawal from medication for at least 3 weeks.

The therapeutic unit for cyclophosphamide is such that, for example, in the case of intravenous injection, 100 mg is administered once a day by intravenous injection for consecutive days. If the patient can tolerate, the daily dose may be increased to 200 mg. The total dose is 3,000 to 8,000 mg, which may be appropriately increased or decreased. If necessary, it may be injected or infused intramuscularly, intrathoracically or intratumorally. On the other hand, in the case of oral administration, for example, 100 to 200 mg is administered a day.

The therapeutic unit for gefitinib is such that 250 mg is orally administered once a day.

The therapeutic unit for cetuximab is such that, for example, 400 mg/m$^2$ is administered on the first day by intravenous drip infusion, and then 250 mg/m$^2$ is administered every week by intravenous drip infusion.

The therapeutic unit for bevacizumab is such that, for example, 3 mg/kg is administered every week by intravenous drip infusion.

The therapeutic unit for trastuzumab is such that, for example, typically for an adult, once a day, 4 mg as trastuzumab/kg (body weight) is administered initially, followed by intravenous drip infusion of 2 mg/kg over a period of 90 minutes or longer every week from the second administration.

The therapeutic unit for exemestane is such that, for example, typically for an adult, 25 mg is orally administered once a day after meal.

The therapeutic unit for leuprorelin (e.g., leuprorelin acetate) is such that, for example, typically for an adult, 11.25 mg is subcutaneously administered once in 12 weeks.

The therapeutic unit for imatinib is such that, for example, typically for an adult in the chronic phase of chronic myelogenous leukemia, 400 mg is orally administered once a day after meal.

The therapeutic unit for a combination of 5-FU and leucovorin is such that, for example, 425 mg/m$^2$ of 5-FU and 200 mg/m$^2$ of leucovorin are administered from the first day to the fifth day by intravenous drip infusion, and this course is repeated at an interval of 4 weeks.

The compounds of the invention have an excellent Wee1 kinase inhibitory effect, and therefore are useful in the field of medicine, especially in the field of treatment of various cancers.

The invention will be more specifically described with reference to Examples and Production Examples, however, the invention is by no means limited to these.

EXAMPLES

In thin-layer chromatography in Examples and Production Examples, Silica gel$_{60}$ F$_{254}$ (Merck) was used as a plate, and a UV detector was used as a detection unit. Wakogel™ C-300 or C-200 (Wako Pure Chemical Industries, Ltd.) or NH (Fuji Silysia Chemical) was used as a column silica gel. MS spectra were measured using JMS-SX102A (JEOL) or QUATTRO II (Micromass). NMR spectra were measured using dimethyl sulfoxide as an internal standard in the case of performing the measurement in a deuteriated dimethyl sulfoxide solution with a JNM-AL 400 (400 MHz; JEOL), Mercury 400 (400 MHz; Varian) or Inova 400 (400 MHz; Varian) spectrometer, and all δ values are indicated in ppm.

The meanings of the abbreviations in Production Examples and Examples will be shown below.
s: singlet
d: doublet
dd: double doublet
ddd: double double doublet
t: triplet
dt: double triplet
ddt: double double triplet
q: quartet
m: multiplet
br: broad
J: coupling constant
Hz: hertz
DMSO-d$_6$: deuteriated dimethyl sulfoxide
CDCl$_3$: deuteriated chloroform
CD$_3$OD: deuteriated methanol
mCPBA: 3-chlorobenzoic acid
DIPEA: N,N-diisopropylethylamine
DBU: diazabicycloundecene
THP: 2-tetrahydropyranyl group
Et: ethyl group Production Example 1

Production of 3-(2,6-dichlorophenyl)-7-(methylsulfanyl)pyrimido[4,5-d]pyrimidine-2,4(1H,3H)-dione To a solution of 1.0 g of ethyl 4-amino-2-(methylsulfanyl)pyrimidine-5-carboxylate in 15 mL of N,N-dimethylformamide, 315 mg of sodium hydride was added, and the resulting mixture was stirred at room temperature for 5 minutes. To the reaction mixture, 970 mg of 2,6-dichlorophenyl isocyanate was added, and the resulting mixture was stirred at room temperature for 1 hour. To the reaction mixture, ethyl acetate and a 1 N aqueous hydrochloric acid solution were added and the organic layer was separated. The organic layer was washed with saturated saline and dried over anhydrous sodium sulfate, and then, the solvent was distilled off. The precipitated solid was solidified with methanol and collected by filtration, whereby 1.43 g of the title compound was obtained as a white solid.

$^1$H-NMR (400 MHz, DMSO-d$_6$) δ: 12.93 (1H, br s), 9.01 (1H, s), 7.68 (2H, d, J=8.0 Hz), 7.54 (1H, t, J=8.0 Hz). 2.57 (3H, s).

ESI-MS Found: m/z[M+H] 354

Production Example 2

Production of 3-(2-chloro-6-methylphenyl)-7-(methylsulfanyl)pyrimido[4,5-d]pyrimidine-2,4(1H,3H)-dione To a solution of 100 mg of ethyl 4-amino-2-(methylsulfanyl)pyrimidine-5-carboxylate in 4 mL of N,N-dimethylformamide, 56 mg of sodium hydride was added, and the resulting mixture was stirred at room temperature for 5 minutes. To the reaction mixture, 118 mg of 2-chloro-6-methylphenyl isocyanate was added, and the resulting mixture was stirred at room temperature for 1 hour. To the reaction mixture, ethyl acetate and a 1 N aqueous hydrochloric acid solution were added and the organic layer was separated. The organic layer was washed with saturated saline and dried over anhydrous sodium sulfate, and then, the solvent was distilled off. The precipitated solid was solidified with methanol and collected by filtration, whereby 100 mg of the title compound was obtained as a white solid.

ESI-MS Found: m/z[M+H] 335

Production Example 3

Production of 3-(2,6-dichlorophenyl)-1-methyl-7-(methylsulfanyl)pyrimido[4,5-d]pyrimidine-2,4(1H,3H)-dione

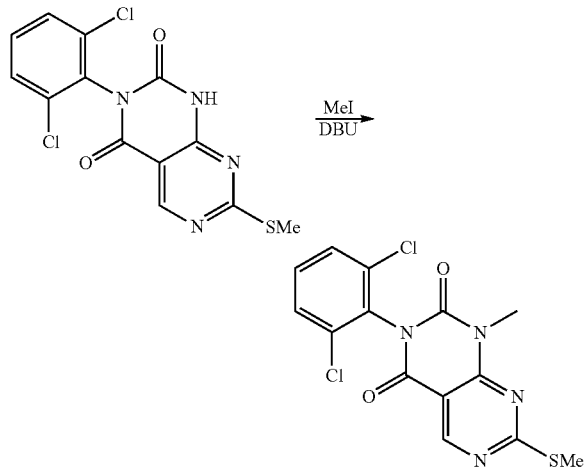

To a solution of 500 mg of 3-(2,6-dichlorophenyl)-7-(methylsulfanyl)pyrimido[4,5-d]pyrimidine-2,4(1H,3H)-dione obtained in the Production Example 1 in 5 mL of N,N-dimethylformamide, 211 µL of DBU and 105 µL of methyl iodide were added, and the resulting mixture was stirred at room temperature for 1 hour. The reaction mixture was added to a 0.5 N aqueous hydrochloric acid solution along with ethyl acetate while stirring and the organic layer was separated. The organic layer was washed with saturated saline and dried over anhydrous sodium sulfate, and then, the solvent was distilled off. The crude product was solidified from methanol, whereby 420 mg of the title compound was obtained as a yellow solid.

$^1$H-NMR (400 MHz, DMSO-$d_6$) δ: 9.11 (1H, s), 7.69 (2H, d, J=8.0 Hz), 7.56 (1H, t, J=8.0 Hz), 3.55 (3H, s), 2.65 (3H, s).

ESI-MS Found: m/z[M+H]+368

Production Example 4

Production of 3-(2,6-dichlorophenyl)-7-(methylsulfanyl)-1-[2-(tetrahydro-2H-pyran-2-yloxy)ethyl]pyrimido[4,5-d]pyrimidine-2,4(1H,3H)-dione

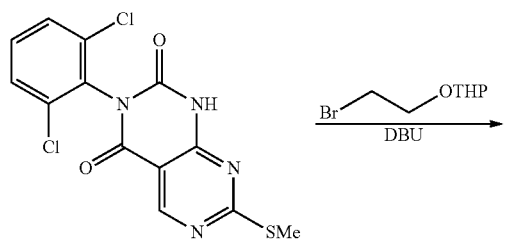

-continued

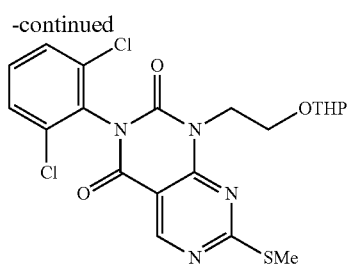

To a solution of 40 mg of 3-(2,6-dichlorophenyl)-7-(methylsulfanyl)pyrimido[4,5-d]pyrimidine-2,4(1H,3H)-dione obtained in the Production Example 1 in 2 mL of N,N-dimethylformamide, 26 mg of DBU and 31 mg of 2-(2-bromoethoxy)tetrahydro-2H-pyran were added, and the resulting mixture was stirred at room temperature for 12 hours. The reaction mixture was added to water along with ethyl acetate while stirring and the organic layer was separated. The organic layer was washed with saturated saline and dried over anhydrous sodium sulfate, and then, the solvent was distilled off. The crude product was purified by silica gel column chromatography, whereby 20 mg of the title compound was obtained as a yellow solid.

ESI-MS Found: m/z[M+H]+484

Production Example 5

Production of 3-(2,4-dichloropyridin-3-yl)-7-(methylsulfanyl)pyrimido[4,5-d]pyrimidine-2,4(1H,3H)-dione

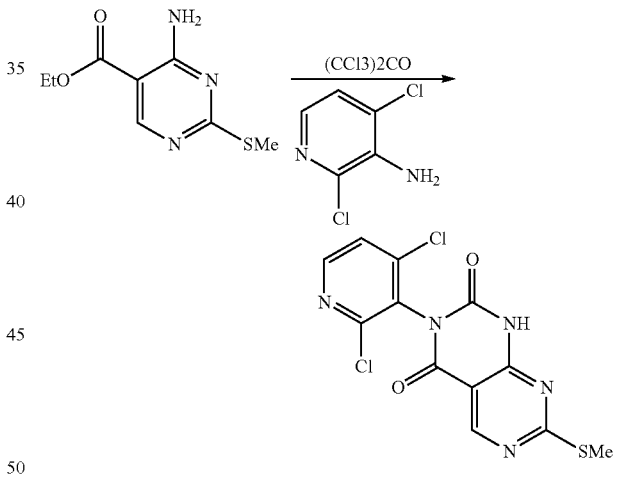

To a solution of 100 mg of ethyl 4-amino-2-(methylsulfanyl)pyrimidine-5-carboxylate in 10 mL of dichloromethane, 56 mg of triphosgene and 142 mg of triethylamine were added, and the resulting mixture was stirred for 1 hour. After the mixture was concentrated, the residue was dissolved in 5 mL of N,N-dimethylformamide, and then, 76 mg of 2,4-dichloropyridin-3-amine and 25 mg of sodium hydride were added thereto, and the resulting mixture was stirred at room temperature for 1 hour. To the reaction mixture, chloroform and a 1 N aqueous hydrochloric acid solution were added and the organic layer was separated. The organic layer was washed with saturated saline and dried over anhydrous sodium sulfate, and then, the solvent was distilled off. The crude product was purified by silica gel column chromatography, whereby 35 mg of the title compound was obtained as a yellow solid.

ESI-MS Found: m/z[M+H] 355

Example 1

Production of 3-(2,6-dichlorophenyl)-7-{[3-methyl-4-(4-methylpiperazin-1-yl)phenyl]amino}pyrimido[4,5-d]pyrimidine-2,4(1H,3H)-dione

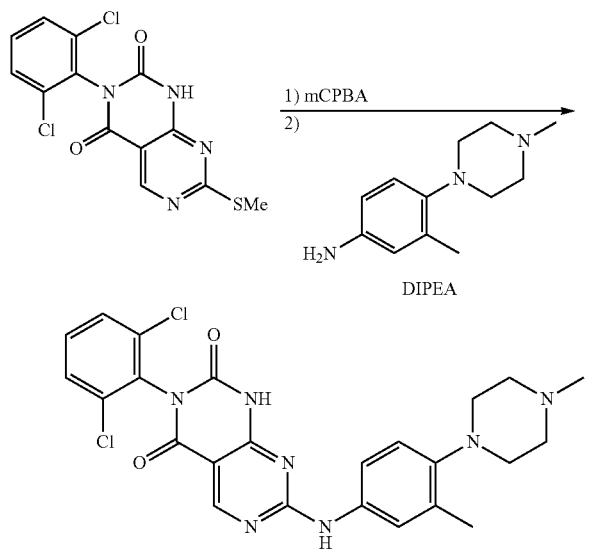

To 6 mL of a chloroform solution containing 50 mg of 3-(2,6-dichlorophenyl)-7-(methylsulfanyl)pyrimido[4,5-d]pyrimidine-2,4(1H,3H)-dione obtained in the Production Example 1, 49 mg of mCPBA was added, and the resulting mixture was stirred at room temperature for 15 minutes, and then, the solvent was distilled off. The thus obtained crude product was dissolved in 7 mL of toluene, and 29 mg of 3-methyl-4-(4-methylpiperazin-1-yl)aniline and 55 mg of DIPEA were added thereto, and the resulting mixture was stirred at 90° C. for 12 hours. The reaction liquid was distilled off, and the thus obtained crude purified product was purified by basic silica gel column chromatography, whereby 17 mg (yield: 24%) of 3-(2,6-dichlorophenyl)-7-{[3-methyl-4-(4-methylpiperazin-1-yl)phenyl]amino}pyrimido[4,5-d]pyrimidine-2,4(1H,3H)-dione was obtained as a yellow solid.

$^1$H-NMR (400 MHz, CD$_3$OD-d$_6$) δ: 8.93 (1H, s), 7.50-7.37 (3H, m), 7.35-7.29 (2H, m), 7.06 (1H, d, J=8.4 Hz), 2.95 (4H, br), 2.63 (4H, br), 2.38 (3H, s), 2.33 (3H, s), 2.21 (3H, s).

ESI-MS Found: m/z[M+H] 512

Example 2

Production of 3-(2-chloro-6-methylphenyl)-7-{[3-methyl-4-(4-methylpiperazin-1-yl)phenyl]amino}pyrimido[4,5-d]pyrimidine-2,4(1H,3H)-dione

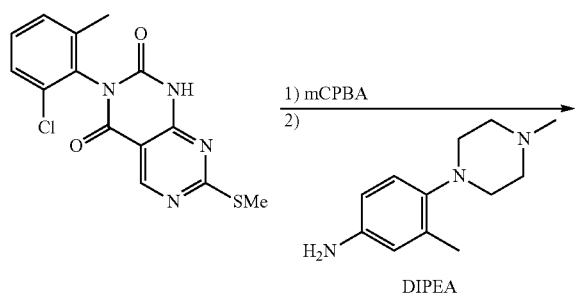

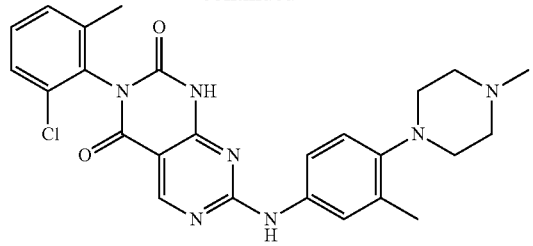

To 4 mL of a chloroform solution containing 40 mg of 3-(2-chloro-6-methylphenyl)-7-(methylsulfanyl)pyrimido[4,5-d]pyrimidine-2,4(1H,3H)-dione obtained in the Production Example 2, 41 mg of mCPBA was added, and the resulting mixture was stirred at room temperature for 15 minutes, and then, the solvent was distilled off. The thus obtained crude product was dissolved in 4 mL of toluene, and 25 mg of 3-methyl-4-(4-methylpiperazin-1-yl)aniline and 40 mg of DIPEA were added thereto, and the resulting mixture was stirred at 90° C. for 12 hours. The solid in the reaction mixture was collected by filtration and purified by basic silica gel column chromatography, whereby 9 mg (yield: 15%) of 3-(2-chloro-6-methylphenyl)-7-{[3-methyl-4-(4-methylpiperazin-1-yl)phenyl]amino}pyrimido[4,5-d]pyrimidine-2,4(1H,3H)-dione was obtained as a yellow solid.

$^1$H-NMR (400 MHz, CD$_3$OD) δ: 8.93 (1H, s), 7.50-7.37 (3H, m), 7.35-7.29 (2H, m), 7.06 (1H, d, J=8.4 Hz), 2.95 (4H, br), 2.63 (4H, br), 2.38 (3H, s), 2.33 (3H, s), 2.21 (3H, s).

ESI-MS Found: m/z[M+H] 492

Example 3

Production of 3-(2,6-dichlorophenyl)-1-methyl-7-{[3-methyl-4-(4-methylpiperazin-1-yl)phenyl]amino}pyrimido[4,5-d]pyrimidine-2,4(1H,3H)-dione

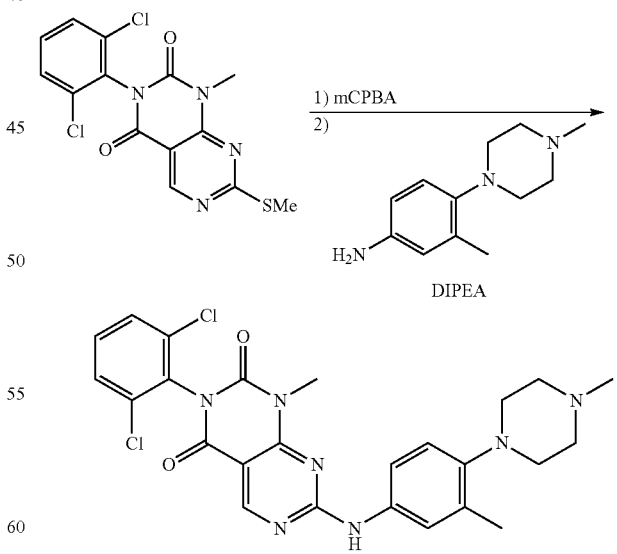

To 15 mL of a chloroform solution containing 40 mg of 3-(2,6-dichlorophenyl)-1-methyl-7-(methylsulfanyl)pyrimido[4,5-d]pyrimidine-2,4(1H,3H)-dione obtained in the Production Example 3, 37 mg of mCPBA was added, and the resulting mixture was stirred at room temperature for 15 minutes, and then, the solvent was distilled off. The thus obtained crude product was dissolved in a mixed solvent containing 10 mL of toluene and 1 mL of N,N-dimethylformamide, and 22 mg of 3-methyl-4-(4-methylpiperazin-1-yl)aniline and 42 mg of DIPEA were added thereto, and the resulting mixture was stirred at 90° C. for 12 hours. The reaction liquid was distilled off and the thus obtained crude purified product was purified by basic silica gel column chromatography, whereby 13 mg (yield: 22%) of 3-(2,6-dichlorophenyl)-1-methyl-7-{[3-methyl-4-(4-methylpiperazin-1-yl)phenyl]amino}pyrimido[4,5-d]pyrimidine-2,4(1H,3H)-dione was obtained as a yellow solid.

$^1$H-NMR (400 MHz, CD$_3$OD-d$_6$) δ: 8.95 (1H, s), 7.56-7.50 (4H, m), 7.45 (2H, d, J=7.6 Hz), 7.09 (1H, d, J=8.4 Hz), 3.69 (3H, s), 2.98 (4H, br), 2.67 (4H, br), 2.39 (3H, s), 2.35 (3H, s).

ESI-MS Found: m/z[M+H] 526

Example 4

Production of 3-(2,6-dichlorophenyl)-1-methyl-7-{[4-(4-methylpiperazin-1-yl)phenyl]amino}pyrimido[4,5-d]pyrimidine-2,4(1H,3H)-dione

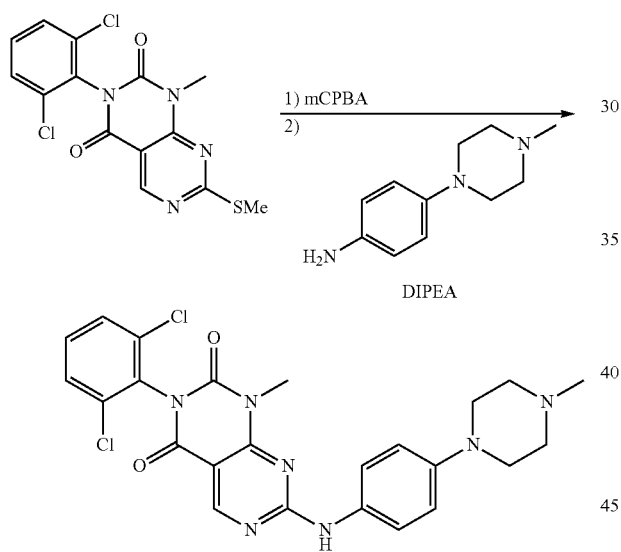

To 15 mL of a chloroform solution containing 35 mg of 3-(2,6-dichlorophenyl)-1-methyl-7-(methylsulfanyl)pyrimido[4,5-d]pyrimidine-2,4(1H,3H)-dione obtained in the Production Example 3, 33 mg of mCPBA was added, and the resulting mixture was stirred at room temperature for 15 minutes, and then, the solvent was distilled off. The thus obtained crude product was dissolved in 15 mL of toluene, and 22 mg of 4-(4-methylpiperazin-1-yl)aniline and 42 mg of DIPEA were added thereto, and the resulting mixture was stirred at 90° C. for 12 hours. The reaction liquid was distilled off and the thus obtained crude purified product was purified by basic silica gel column chromatography, whereby 12 mg (yield: 24%) of 3-(2,6-dichlorophenyl)-1-methyl-7-{[4-(4-methylpiperazin-1-yl)phenyl]amino}pyrimido[4,5-d]pyrimidine-2,4(1H,3H)-dione was obtained as a yellow solid.

$^1$H-NMR (400 MHz, CDCl$_3$) δ: 9.00 (1H, s), 7.74 (1H, br), 7.55-7.47 (3H, m), 7.37 (1H, t, J=7.4 Hz), 6.97 (2H, d, J=8.4 Hz), 3.66 (3H, s), 3.23 (4H, br), 2.61 (4H, br), 2.37 (3H, s).

ESI-MS Found: m/z[M+H] 512

Example 5

Production of 3-(2,6-dichlorophenyl)-1-(1-methyl-1H-pyrazol-3-yl)-7-{[3-methyl-4-(4-methylpiperazin-1-yl)phenyl]amino}pyrimido[4,5-d]pyrimidine-2,4(1H,3H)-dione 1) Ethyl 4-[(1-methyl-1H-pyrazol-3-yl)amino]-2-(methylsulfanyl)pyrimidine-5-carboxylate

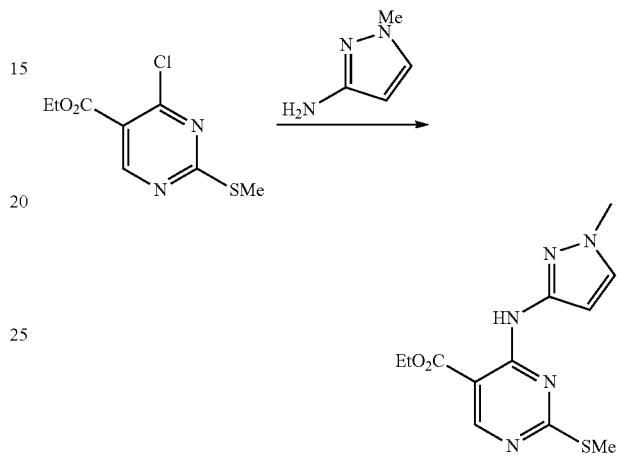

To a solution of 800 mg of ethyl 4-chloro-2-(methylsulfanyl)pyrimidine-5-carboxylate in 20 mL of THF, 890 mg of DIPEA and 368 mg of 1-methyl-1H-pyrazol-3-amine were added, and the resulting mixture was stirred under reflux for 2 hours, and then, the solvent was distilled off. The thus obtained crude product was purified by silica gel column chromatography, whereby 820 mg the title compound was obtained.

2) 3-(2,6-dichlorophenyl)-1-(1-methyl-1H-pyrazol-3-yl)-7-(methylsulfanyl)pyrimido[4,5-d]pyrimidine-2,4(1H,3H)-dione

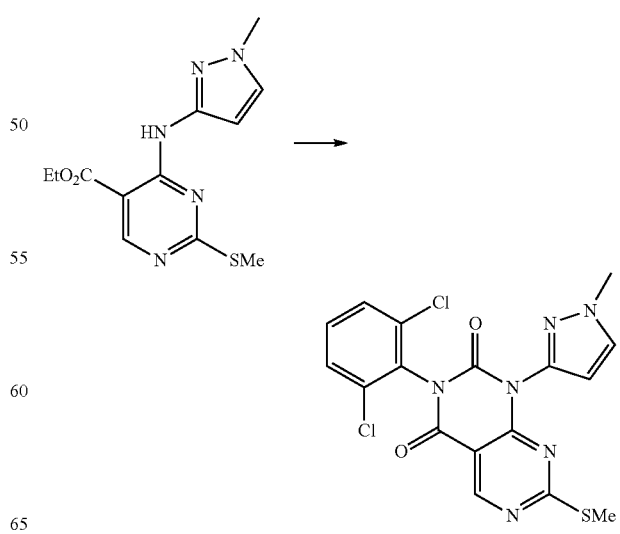

75 mg of the title compound was obtained in the same manner as in the Production Example 1 except that ethyl 4-[(1-methyl-1H-pyrazol-3-yl)amino]-2-(methylsulfanyl)pyrimidine-5-carboxylate obtained in the above 1) was used instead of ethyl 4-amino-2-(methylsulfanyl)pyrimidine-5-carboxylate used in the Production Example 1.

3) 3-(2,6-dichlorophenyl)-1-(1-methyl-1H-pyrazol-3-yl)-7-{[3-methyl-4-(4-methylpiperazin-1-yl)phenyl]amino)pyrimido[4,5-d]pyrimidine-2,4(1H,3H)-dione

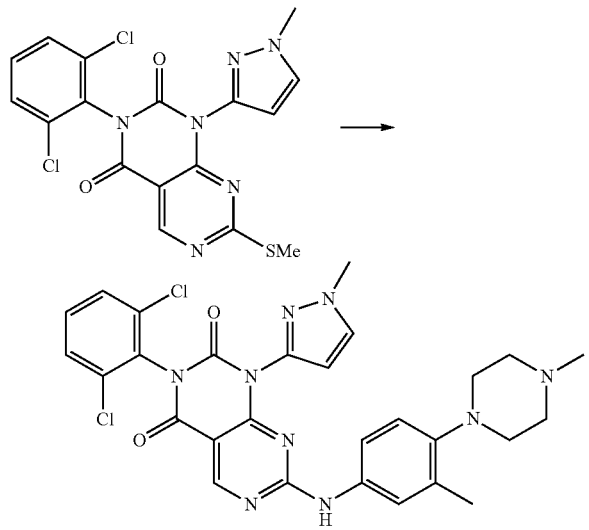

18 mg of the title compound was obtained as a yellow solid in the same manner as in the Example 2 except that 3-(2,6-dichlorophenyl)-1-(1-methyl-1H-pyrazol-3-yl)-7-(methylsulfanyl)pyrimido[4,5-d]pyrimidine-2,4(1H,3H)-dione obtained in the above 2) was used instead of 3-(2,6-dichlorophenyl)-7-(methylsulfanyl)pyrimido[4,5-d]pyrimidine-2,4(1H,3H)-dione used in the Production Example 2.

$^1$H-NMR (400 MHz, CDCl$_3$) δ: 9.04 (1H, s), 7.71 (1H, br), 7.57 (1H, br), 7.46 (2H, d, J=8.4 Hz), 7.37-7.26 (1H, m), 7.18-7.00 (1H, m), 6.85 (1H, br), 6.43 (1H, br), 4.00 (3H, s), 2.92 (4H, br), 2.62 (4H, br), 2.39 (3H, s), 2.20 (3H, s).
ESI-MS Found: m/z[M+H] 592

Example 6

Production of 3-(2,6-dichlorophenyl)-1-(2-hydroxyethyl)-7-{[3-methyl-4-(4-methylpiperazin-1-yl)phenyl]amino}pyrimido[4,5-d]pyrimidine-2,4(1H,3H)-dione

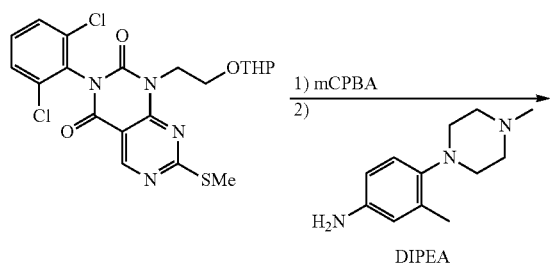

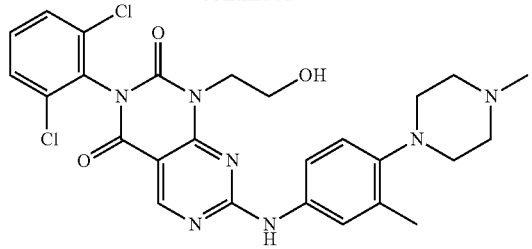

To 3 mL of a toluene solution containing 20 mg of 3-(2,6-dichlorophenyl)-7-(methylsulfanyl)-1-[2-(tetrahydro-2H-pyran-2-yloxy)ethyl]pyrimido[4,5-d]pyrimidine-2,4(1H,3H)-dione obtained in the Production Example 4, 14 mg of mCPBA was added, and the resulting mixture was stirred at room temperature for 15 minutes. Then, 8.5 mg of 3-methyl-4-(4-methylpiperazin-1-yl)aniline and 16 mg of DIPEA were added thereto, and the resulting mixture was stirred at 90° C. for 12 hours. The reaction liquid was distilled off, and the residue was dissolved in 10 mL of HCl-methanol, and the resulting mixture was stirred at room temperature for 15 minutes. After the reaction liquid was distilled off, 7 N ammonia-methanol was added to the residue, followed by neutralization and concentration. The thus obtained crude purified product was purified by basic silica gel column chromatography, whereby 4 mg (yield: 17%) of 3-(2,6-dichlorophenyl)-1-(2-hydroxyethyl)-7-{[3-methyl-4-(4-methylpiperazin-1-yl)phenyl]amino}pyrimido[4,5-d]pyrimidine-2,4(1H,3H)-dione was obtained as a yellow solid.

$^1$H-NMR (400 MHz, CD$_3$OD) δ: 8.95 (1H, s), 7.87 (2H, br), 7.58 (2H, d, J=8.4 Hz), 7.49 (1H, t, J=7.4 Hz), 7.10 (2H, d, J=8.4 Hz), 4.47 (2H, t, J=6.4 Hz), 3.91 (2H, t, J=6.4 Hz), 2.97 (4H, br), 2.66 (4H, br), 2.38 (3H, s), 3.36 (3H, s).
ESI-MS Found: m/z[M+H] 556

Example 7

Production of 3-(2,4-dichloropyridin-3-yl)-7-{[3-methyl-4-(4-methylpiperazin-1-yl)phenyl]amino}pyrimido[4,5-d]pyrimidine-2,4(1H,3H)-dione

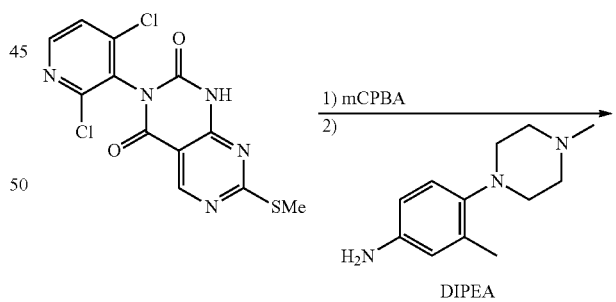

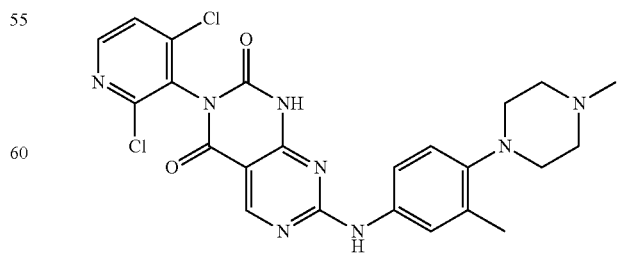

To 10 mL of a chloroform solution containing 35 mg of 3-(2,4-dichloropyridin-3-yl)-7-(methylsulfanyl)pyrimido[4,5-d]pyrimidine-2,4(1H,3H)-dione obtained in the Production Example 5, 36 mg of mCPBA was added, and the resulting mixture was stirred at room temperature for 15 minutes, and then, the solvent was distilled off. The thus obtained crude product was dissolved in 10 mL of toluene, and 21 mg of 3-methyl-4-(4-methylpiperazin-1-yl)aniline and 41 mg of DIPEA were added thereto, and the resulting mixture was stirred at 90° C. for 12 hours. The reaction liquid was distilled off, and the thus obtained crude purified product was purified by basic silica gel column chromatography, whereby 7 mg (yield: 13%) of 3-(2,4-dichloropyridin-3-yl)-7-{[3-methyl-4-(4-methylpiperazin-1-yl)phenyl]amino}pyrimido[4,5-d]pyrimidine-2,4(1H,3H)-dione was obtained as a yellow solid.

¹H-NMR (400 MHz, CD₃OD) δ: 8.87 (1H, s), 8.37 (1H, d, J=7.6 Hz), 7.59 (2H, d, J=7.6 Hz), 7.48 (2H, br), 7.05 (1H, d, J=8.4 Hz), 2.95 (4H, br), 2.66 (4H, br), 2.38 (3H, s), 2.33 (3H, s).

ESI-MS Found: m/z[M+H] 513

Compounds of Examples 8 to 72 were obtained in the same manner as in the above-mentioned Examples appropriately using corresponding raw materials (in the above or below-mentioned structural formulae, a hydrogen atom of the group represented by —NH— or —NH₂ is conveniently omitted, and —NH or —NH₂ is denoted by —N— or —N, respectively, in some cases).

Example 8

3-(2,6-dichlorophenyl)-1-ethyl-7-{[4-(4-methylpiperazin-1-yl)phenyl]amino}pyrimido[4,5-d]pyrimidine-2,4(1H,3H)-dione

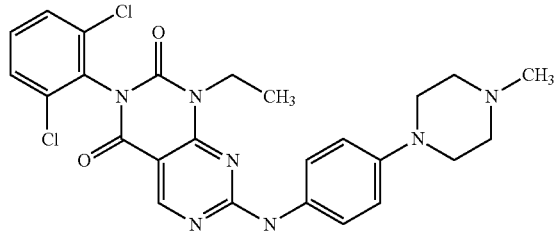 [SMILES: CCn1c(=O)n(-c2c(Cl)cccc2Cl)c(=O)c2cnc(Nc3ccc(N4CCN(C)CC4)cc3)nc21]

¹H-NMR (400 MHz, CDCl₃) δ: 9.00 (1H, s), 7.84 (1H, br), 7.50 (2H, br), 7.48 (2H, d, J=8.4 Hz), 7.34 (1H, t, J=7.4 Hz), 6.97 (2H, d, J=8.4 Hz), 4.33 (2H, q, J=7.2 Hz), 3.24 (4H, br), 2.61 (4H, br), 2.37 (3H, s), 1.35 (3H, t, J=7.2 Hz).

ESI-MS Found: m/z[M+H] 526

Example 9

7-{[4-(4-acetylpiperazin-1-yl)-3-methylphenyl]amino}-3-(2,6-dichlorophenyl)pyrimido[4,5-d]pyrimidine-2,4(1H,3H)-dione

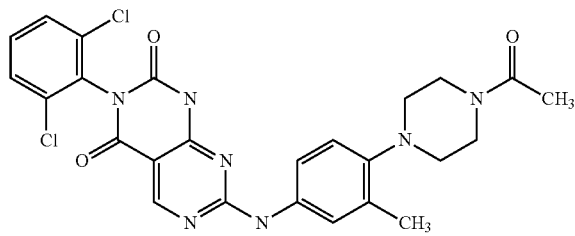 [SMILES: CC(=O)N1CCN(c2ccc(Nc3ncc4c(=O)n(-c5c(Cl)cccc5Cl)c(=O)[nH]c4n3)cc2C)CC1]

¹H-NMR (400 MHz, CD₃OD) δ: 8.96 (1H, s), 7.52-7.39 (5H, m), 7.02 (2H, d, J=8.8 Hz), 3.76 (2H, br), 3.66 (2H, br), 2.94 (2H, br), 2.88 (2H, br), 2.37 (3H, s), 2.17 (3H, s).

ESI-MS Found: m/z[M+H] 540

Example 10

7-({4-[4-(1-acetylazetidin-3-yl)piperazin-1-yl]phenyl}amino)-3-(2,6-dichlorophenyl)-1-methylpyrimido[4,5-d]pyrimidine-2,4(1H,3H)-dione

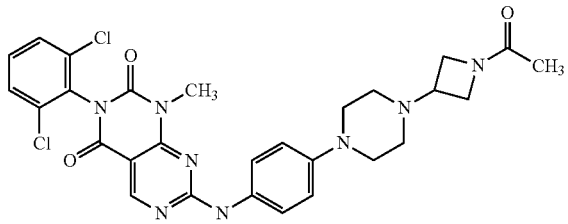 [SMILES: CC(=O)N1CC(N2CCN(c3ccc(Nc4ncc5c(=O)n(-c6c(Cl)cccc6Cl)c(=O)n(C)c5n4)cc3)CC2)C1]

¹H-NMR (400 MHz, CD₃OD) δ: 9.00 (1H, s), 7.91 (1H, br), 7.53 (2H, br), 7.48 (2H, d, J=8.8 Hz), 7.37 (2H, t, J=7.4 Hz), 6.97 (2H, d, J=8.8 Hz), 4.12-4.17 (1H, m), 4.09-4.03 (2H, m), 3.94-3.90 (1H, m), 3.66 (3H, s), 3.25 (5H, br), 2.67 (4H, br), 1.89 (3H, s).

ESI-MS Found: m/z[M+H] 595

Example 11

3-(2,6-dichlorophenyl)-7-({4-[4-(2-hydroxy-2-methylpropyl)piperazin-1-yl]phenyl}amino)pyrimido[4,5-d]pyrimidine-2,4(1H,3H)-dione

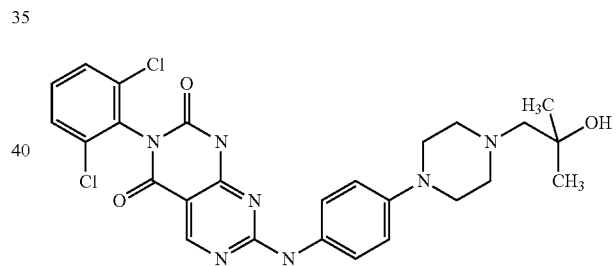

¹H-NMR (400 MHz, CD₃OD) δ: 8.96 (1H, s), 7.55-7.45 (4H, m), 7.42-7.35 (1H, m), 6.97 (2H, d, J=8.8 Hz), 3.21 (4H, br), 2.83 (4H, br), 2.43 (2H, s), 1.23 (6H, s).

ESI-MS Found: m/z[M+H] 556

Example 12

3-(2,6-dichlorophenyl)-7-[(4-{4-[(dimethylamino)acetyl]piperazin-1-yl}phenyl)amino]pyrimido[4,5-d]pyrimidine-2,4(1H,3H)-dione

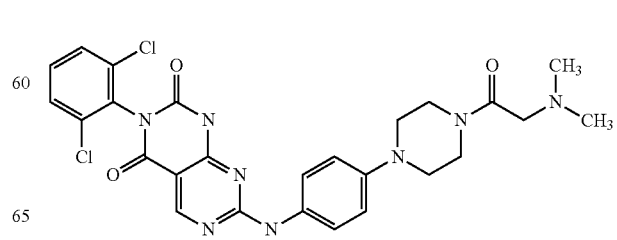

¹H-NMR (400 MHz, CD₃OD) δ: 8.96 (1H, s), 7.63 (2H, br), 7.52 (2H, d, J=8.4 Hz), 7.44-7.40 (1H, br), 6.98 (2H, d, J=8.4 Hz), 3.77 (4H, br), 3.78 (2H, s), 3.19 (4H, br), 2.36 (6H, s).
ESI-MS Found: m/z[M+H] 569

Example 13

3-(2-chlorophenyl)-1-methyl-7-{[3-methyl-4-(4-methylpiperazin-1-yl)phenyl]amino}pyrimido[4,5-d]pyrimidine-2,4(1H,3H)-dione

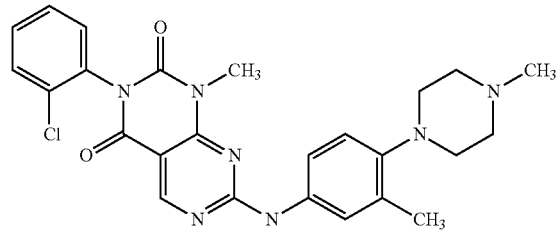 [SMILES: Cc1cc(Nc2ncc3c(=O)n(-c4ccccc4Cl)c(=O)n(C)c3n2)ccc1N1CCN(C)CC1]

¹H-NMR (400 MHz, CD₃OD) δ: 8.95 (1H, s), 7.98 (1H, br), 7.89 (1H, d, J=8.0 Hz), 7.49-7.43 (2H, m), 7.38-7.35 (2H, m), 7.10 (1H, d, J=8.8 Hz), 3.76 (3H, s), 3.11 (4H, br), 3.94 (4H, br), 2.67 (3H, s), 2.36 (3H, s).
ESI-MS Found: m/z[M+H] 492

Example 14

3-(2,6-dichlorophenyl)-7-{[4-(4-methypiperazin-1-yl)phenyl]amino}pyrimido[4,5-d]pyrimidine-2,4(1H,3H)-dione

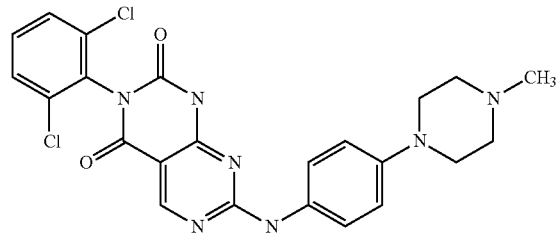 [SMILES: CN1CCN(c2ccc(Nc3ncc4c(=O)n(-c5c(Cl)cccc5Cl)c(=O)[nH]c4n3)cc2)CC1]

¹H-NMR (400 MHz, DMSO) δ: 8.86 (1H, s), 7.71-7.60 (4H, m), 7.57 (1H, t, J=7.6 Hz), 6.93 (1H, d, J=8.8 Hz), 3.12 (4H, br), 2.48 (4H, br), 2.25 (3H, s).
ESI-MS Found: m/z[M+H] 498

Example 15

7-{[4-(1-acetylpiperidin-4-yl)phenyl]amino}-3-(2,6-dichlorophenyl)-1-methylpyrimido[4,5-d]pyrimidine-2,4(1H,3H)-dione

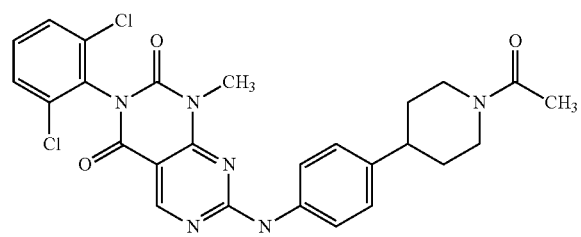 [SMILES: CC(=O)N1CCC(c2ccc(Nc3ncc4c(=O)n(-c5c(Cl)cccc5Cl)c(=O)n(C)c4n3)cc2)CC1]

¹H-NMR (400 MHz, CDCl₃) δ: 9.05 (1H, s), 7.70-7.59 (3H, m), 7.50 (1H, d, J=8.4 Hz), 7.37 (1H, t, J=7.4 Hz), 7.25 (2H, d, J=8.4 Hz), 4.84-4.79 (1H, m), 3.98-3.94 (1H, m), 3.69 (3H, s), 3.22-3.16 (1H, m), 2.78-2.70 (1H, m), 2.67-2.61 (1H, m), 2.14 (3H, s), 1.96-1.89 (2H, m), 1.67-1.59 (2H, m).
ESI-MS Found: m/z[M+H] 539

Example 16

3-(2,6-dichlorophenyl)-7-{[4-(3-hydroxyazetidin-1-yl)-3-methylphenyl]amino}pyrimido[4,5-d]pyrimidine-2,4(1H,3H)-dione

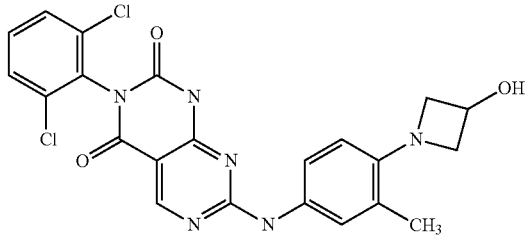 [SMILES: Cc1cc(Nc2ncc3c(=O)n(-c4c(Cl)cccc4Cl)c(=O)[nH]c3n2)ccc1N1CC(O)C1]

¹H-NMR (400 MHz, CD₃OD) δ: 8.94 (1H, s), 7.54 (2H, d, J=8.4 Hz), 7.44 (1H, d, J=7.4 Hz), 7.40-7.30 (2H, m), 6.59 (1H, d, J=8.4 Hz), 4.68-4.65 (1H, m), 4.24-4.20 (2H, m), 3.68-3.65 (2H, m), 2.27 (3H, s).
ESI-MS Found: m/z[M+H] 485

Example 17

3-(2,6-dichlorophenyl)-7-{[4-(4-hydroxypiperidin-1-yl)-3-methylphenyl]amino}pyrimido[4,5-d]pyrimidine-2,4(1H,3H)-dione

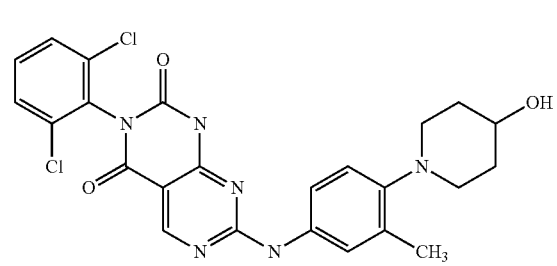 [SMILES: Cc1cc(Nc2ncc3c(=O)n(-c4c(Cl)cccc4Cl)c(=O)[nH]c3n2)ccc1N1CCC(O)CC1]

¹H-NMR (400 MHz, CD₃OD) δ: 8.93 (1H, s), 7.55-7.51 (3H, m), 7.45-7.40 (2H, m), 7.05 (1H, d, J=8.4 Hz), 3.77 (1H, br), 3.10-3.08 (2H, m), 2.76-2.70 (2H, m), 2.34 (3H, s), 2.05-1.99 (2H, m), 1.76-1.70 (2H, m).
ESI-MS Found: m/z[M+H] 513

Example 18

7-{[4-(4-acetylpiperazin-1-yl)phenyl]amino}-1-ethyl-3-(2,6-dichlorophenyl)pyrimido[4,5-d]pyrimidine-2,4(1H,3H)-dione

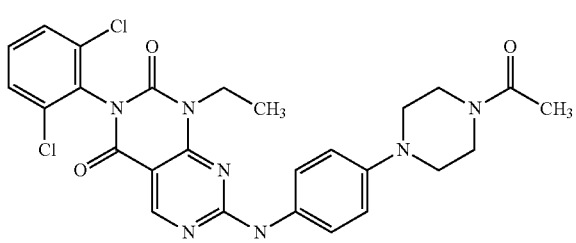 [SMILES: CCn1c(=O)n(-c2c(Cl)cccc2Cl)c(=O)c2cnc(Nc3ccc(N4CCN(C(C)=O)CC4)cc3)nc21]

$^1$H-NMR (400 MHz, CDCl$_3$) δ: 9.01 (1H, s), 7.54 (2H, br), 7.48 (2H, d, J=8.4 Hz), 7.34 (1H, t, J=7.4 Hz), 6.97 (2H, d, J=8.4 Hz), 4.33 (2H, q, J=7.2 Hz), 3.81 (2H, br), 3.65 (2H, br), 3.19 (4H, br), 2.16 (3H, s), 1.37 (3H, t, J=7.2 Hz).

ESI-MS Found: m/z[M+H] 554

Example 19

3-(2,6-dichlorophenyl)-7-({4-[4-(difluoroacetyl)piperazin-1-yl]phenyl}amino)pyrimido[4,5-d]pyrimidine-2,4(1H,3H)-dione

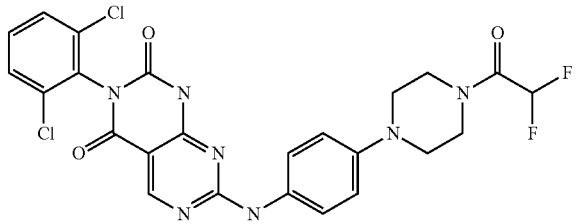 [SMILES: O=C(C(F)F)N1CCN(c2ccc(Nc3ncc4c(=O)n(-c5c(Cl)cccc5Cl)c(=O)[nH]c4n3)cc2)CC1]

$^1$H-NMR (400 MHz, CD$_3$OD) δ: 8.95 (1H, s), 7.64 (2H, br), 7.51 (2H, d, J=8.8 Hz), 7.42 (1H, t, J=8.3 Hz), 3.76 (2H, br), 6.98 (2H, d, J=8.8 Hz), 6.26 (1H, t, J=53 Hz), 3.82 (4H, br), 3.22 (4H, br).

ESI-MS Found: m/z[M+H] 562

Example 20

3-(2-chlorophenyl)-7-{[3-methyl-4-(piperazin-1-yl)phenyl]amino}pyrimido[4,5-d]pyrimidine-2,4(1H,3H)-dione

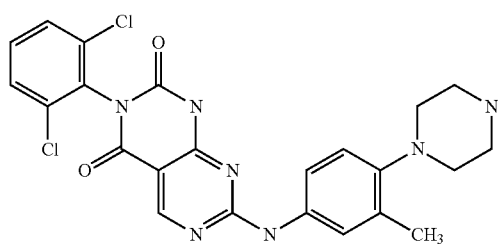 [SMILES: Cc1cc(Nc2ncc3c(=O)n(-c4c(Cl)cccc4Cl)c(=O)[nH]c3n2)ccc1N1CCNCC1]

$^1$H-NMR (400 MHz, CD$_3$OD) δ: 8.94 (1H, s), 7.59-7.57 (1H, m), 7.45-7.42 (4H, m), 7.36-7.33 (1H, m), 7.03 (2H, d, J=8.8 Hz), 3.02 (4H, br), 2.89 (4H, br), 2.33 (3H, s).

ESI-MS Found: m/z[M+H] 464

Example 21

7-{[4-(4-acetylpiperidin-1-yl)phenyl]amino}-3-(2,6-dichlorophenyl)pyrimido[4,5-d]pyrimidine-2,4(1H,3H)-dione

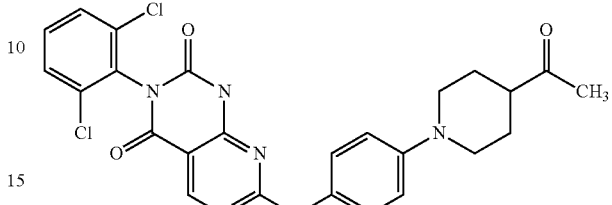

$^1$H-NMR (400 MHz, CD$_3$OD) δ: 8.93 (1H, s), 7.58 (2H, br), 7.51 (2H, d, J=8.4 Hz), 7.41 (1H, t, J=7.4 Hz), 6.99 (2H, d, J=8.4 Hz), 4.37 (3H, s), 3.65-3.61 (2H, m), 2.83-2.76 (2H, m), 2.41 (1H, br), 2.07-2.04 (2H, m), 1.92-1.87 (2H, m).

ESI-MS Found: m/z[M+H] 527

Example 22

3-(2-chlorophenyl)-7-{[3-methyl-4-(4-methylpiperazin-1-yl)phenyl]amino}pyrimido[4,5-d]pyrimidine-2,4(1H,3H)-dione

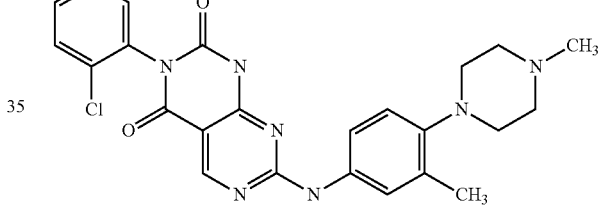

$^1$H-NMR (400 MHz, CDCl$_3$) δ: 9.00 (1H, s), 7.58-7.55 (1H, m), 7.44-7.41 (5H, m), 7.33-7.31 (1H, m), 7.07 (1H, d, J=8.4 Hz), 3.67 (3H, s), 2.96 (4H, br), 2.60 (4H, br), 2.38 (3H, s), 2.34 (3H, s).

ESI-MS Found: m/z[M+H] 492

Example 23

3-(2,6-dichlorophenyl)-7-({4-[(4-methylpiperazin-1-yl)methyl]phenyl}amino)pyrimido[4,5-d]pyrimidine-2,4(1H,3H)-dione

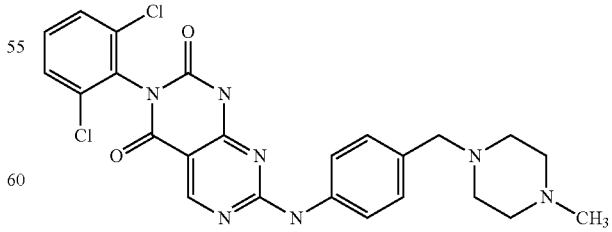

$^1$H-NMR (400 MHz, CD$_3$OD) δ: 8.97 (1H, s), 7.69 (2H, br), 7.52 (2H, d, J=8.8 Hz), 7.40 (1H, t, J=8.3 Hz), 7.32 (2H, d, J=8.8 Hz), 3.53 (2H, s), 2.54 (8H, br), 3.31 (3H, s).

ESI-MS Found: m/z[M+H] 512

Example 24

3-(2,6-dichlorophenyl)-7-({4-[4-(2-hydroxy-2-methylpropionyl)piperazin-1-yl]phenyl}amino)pyrimido[4,5-d]pyrimidine-2,4(1H,3H)-dione

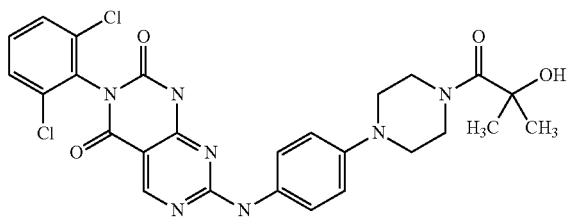 [SMILES: CC(C)(O)C(=O)N1CCN(c2ccc(Nc3ncc4c(=O)n(-c5c(Cl)cccc5Cl)c(=O)[nH]c4n3)cc2)CC1]

$^1$H-NMR (400 MHz, CDCl$_3$) δ: 9.06 (1H, s), 7.60 (2H, br), 7.52 (2H, d, J=8.4 Hz), 7.40 (1H, t, J=7.6 Hz), 7.00 (2H, d, J=8.4 Hz), 3.37 (4H, br), 3.20 (4H, br), 1.51 (6H, s).
ESI-MS Found: m/z[M+H] 570

Example 25

3-(2,6-dichlorophenyl)-7-({4-[4-(2-hydroxypropan-2-yl)piperidin-1-yl]phenyl}amino)pyrimido[4,5-d]pyrimidine-2,4(1H,3H)-dione

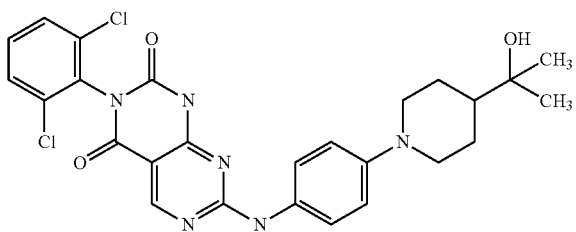 [SMILES: CC(C)(O)C1CCN(c2ccc(Nc3ncc4c(=O)n(-c5c(Cl)cccc5Cl)c(=O)[nH]c4n3)cc2)CC1]

$^1$H-NMR (400 MHz, CD$_3$OD) δ: 8.93 (1H, s), 7.56 (2H, br), 7.53-7.48 (3H, m), 7.42 (1H, t, J=7.6 Hz), 7.01 (2H, d, J=8.8 Hz), 3.74-3.71 (2H, br), 2.69-2.63 (2H, br), 1.92-1.88 (2H, br), 1.55-1.43 (3H, m), 1.21 (6H, s).
ESI-MS Found: m/z[M+H] 541

Example 26

7-{[4-(4-acetylpiperazin-1-yl)phenyl]amino}-3-(2,6-dichlorophenyl)pyrimido[4,5-d]pyrimidine-2,4(1H,3H)-dione

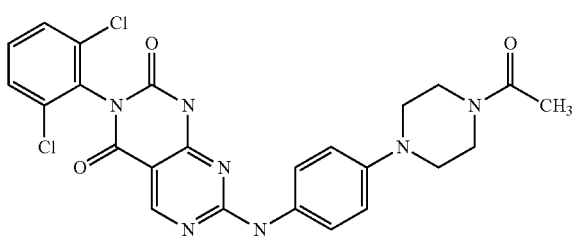

$^1$H-NMR (400 MHz, CD$_3$OD) δ: 8.96 (1H, s), 7.56 (2H, br), 7.51 (2H, d, J=8.8 Hz), 7.41 (1H, t, J=7.6 Hz), 6.96 (2H, d, J=8.8 Hz), 3.77 (2H, br), 3.66 (2H, br), 3.20 (2H, br), 3.15 (2H, br), 2.16 (3H, s).
ESI-MS Found: m/z[M+H] 526

Example 27

3-(2,6-dichlorophenyl)-7-({4-[4-(methoxyacetyl)piperazin-1-yl]phenyl}amino)pyrimido[4,5-d]pyrimidine-2,4(1H,3H)-dione

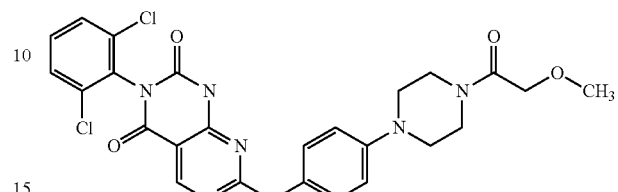

$^1$H-NMR (400 MHz, CD$_3$OD) δ: 8.93 (1H, s), 7.66 (2H, br), 7.52 (2H, d, J=8.8 Hz), 7.43 (1H, t, J=8.3 Hz), 6.99 (2H, d, J=8.8 Hz), 4.19 (2H, s), 3.79 (2H, br), 3.67 (2H, br), 3.46 (3H, s), 3.20 (4H, br).
ESI-MS Found: m/z[M+H] 556

Example 28

7-{[4-(4-acetyl-1,4-diazepan-1-yl)phenyl]amino}-3-(2,6-dichlorophenyl)pyrimido[4,5-d]pyrimidine-2,4(1H,3H)-dione

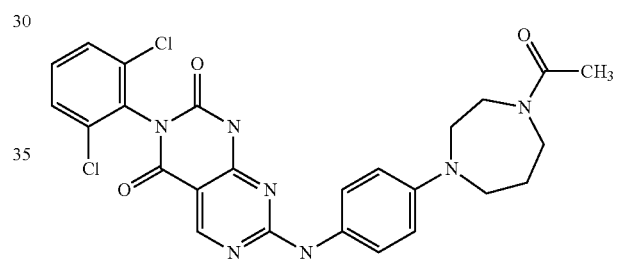

$^1$H-NMR (400 MHz, CDCl$_3$) δ: 10.00 (1H, s), 9.05 (1H, s), 7.51 (2H, d, J=8.4 Hz), 7.42-7.39 (3H, m), 6.66 (2H, d, J=8.4 Hz), 3.74 (1H, br), 3.61-3.53 (4H, m), 3.46 (1H, br), 3.35 (1H, br), 2.10 (6H, s), 1.98 (2H, br).
ESI-MS Found: m/z[M+H] 540

Example 29

2-[4-(4-{[6-(2,6-dichlorophenyl)-5,7-dioxo-5,6,7,8-tetrahydropyrimido[4,5-d]pyrimidin-2-yl]amino}phenyl)piperazin-1-yl]-N,N-dimethylacetamide

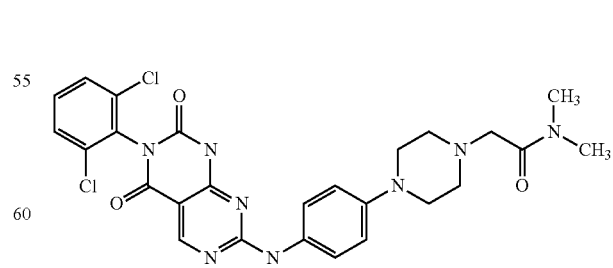

$^1$H-NMR (400 MHz, CD$_3$OD) δ: 8.95 (1H, s), 7.57-7.49 (4H, m), 7.40 (1H, d, J=7.4 Hz), 6.96 (1H, d, J=8.4 Hz), 3.26 (2H, s), 3.22 (4H, br), 3.12 (3H, s), 2.98 (3H, s), 2.72 (4H, br).
ESI-MS Found: m/z[M+H] 569

Example 30

3-(2,6-dichlorophenyl)-7-(phenylamino)pyrimido[4,5-d]pyrimidine-2,4(1H,3H)-dione

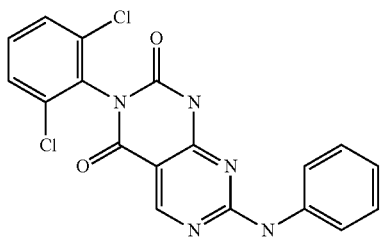 [SMILES: O=c1[nH]c2nc(Nc3ccccc3)ncc2c(=O)n1-c1c(Cl)cccc1Cl]

$^1$H-NMR (400 MHz, CD$_3$OD) δ: 8.96 (1H, s), 7.67 (2H, d, J=8.0 Hz), 7.49 (2H, d, J=8.4 Hz), 7.40-7.35 (3H, m), 7.14 (1H, t, J=8.0 Hz), 3.59 (2H, br), 3.50 (2H, br), 2.76 (2H, br), 2.63 (2H, br), 2.4 (3H, s), 2.06 (2H, br).
ESI-MS Found: m/z[M+H] 400

Example 31

3-(2,6-dichlorophenyl)-7-{[4-(4-methyl-1,4-diazepan-1-yl)phenyl]amino}pyrimido[4,5-d]pyrimidine-2,4(1H,3H)-dione

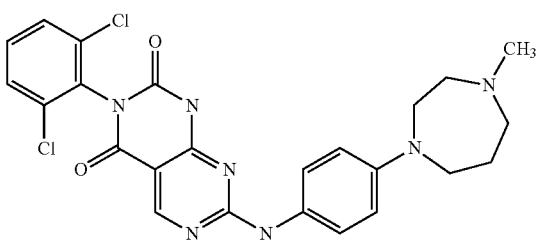 [SMILES: CN1CCCN(c2ccc(Nc3ncc4c(=O)n(-c5c(Cl)cccc5Cl)c(=O)[nH]c4n3)cc2)CC1]

$^1$H-NMR (400 MHz, CD$_3$OD) δ: 8.90 (1H, s), 7.51-7.40 (5H, m), 6.70 (2H, d, J=8.8 Hz), 3.59 (2H, br), 3.50 (2H, br), 2.76 (2H, br), 2.63 (2H, br), 2.4 (3H, s), 2.06 (2H, br).
ESI-MS Found: m/z[M+H] 512

Example 32

3-(2,6-dichlorophenyl)-7-({4-[4-(hydroxyacetyl)piperazin-1-yl]phenyl}amino)pyrimido[4,5-d]pyrimidine-2,4(1H,3H)-dione

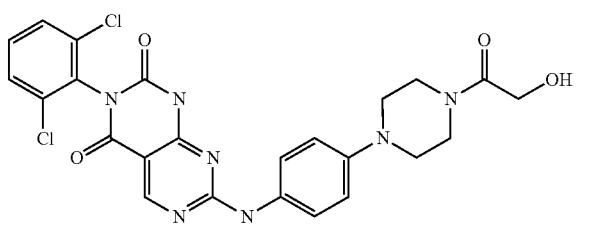 [SMILES: O=C(CO)N1CCN(c2ccc(Nc3ncc4c(=O)n(-c5c(Cl)cccc5Cl)c(=O)[nH]c4n3)cc2)CC1]

$^1$H-NMR (400 MHz, CD$_3$OD) δ: 8.93 (1H, s), 7.64 (2H, br), 7.52 (2H, d, J=8.8 Hz), 7.43 (1H, t, J=8.3 Hz), 6.99 (2H, d, J=8.8 Hz), 4.28 (2H, s), 3.81 (2H, br), 3.56 (2H, br), 3.19 (4H, br).
ESI-MS Found: m/z[M+H] 542

Example 33

3-(2,6-dichlorophenyl)-7-({4-[4-(2-methoxy-2-methylpropionyl)piperazin-1-yl]phenyl}amino)pyrimido[4,5-d]pyrimidine-2,4(1H,3H)-dione

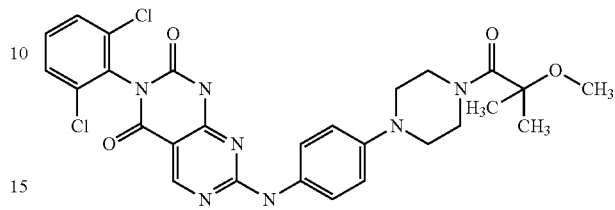

$^1$H-NMR (400 MHz, CD$_3$OD) δ: 8.94 (1H, s), 7.60 (2H, br), 7.51 (2H, d, J=8.8 Hz), 7.41 (1H, t, J=8.3 Hz), 6.99 (2H, d, J=8.8 Hz), 4.20 (2H, br), 3.84 (3H, s), 3.81 (2H, br), 3.28 (3H, br), 3.20 (4H, br), 1.48 (6H, s).
ESI-MS Found: m/z[M+H] 584

Example 34 ethyl 1-(4-{[6-(2,6-dichlorophenyl)-5,7-dioxo-5,6,7,8-tetrahydropyrimido[4,5-d]pyrimidin-2-yl]amino}phenyl)piperidine-4-carboxylate

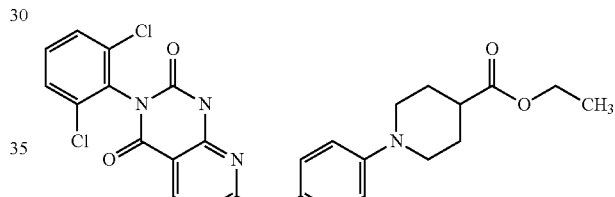

$^1$H-NMR (400 MHz, CDCl$_3$) δ: 10.05 (1H, s), 9.06 (1H, s), 7.50 (2H, d, J=8.4 Hz), 7.45-7.39 (3H, m), 6.89 (1H, d, J=8.4 Hz), 4.15 (2H, q, J=7.2 Hz), 3.60 (2H, br), 2.76 (2H, br), 2.41 (1H, br), 2.01 (2H, br), 1.86 (2H, br).
ESI-MS Found: m/z[M+H] 555

Example 35

4-(4-{[6-(2,6-dichlorophenyl)-5,7-dioxo-5,6,7,8-tetrahydropyrimido[4,5-d]pyrimidin-2-yl]amino}phenyl)piperazine-1-carbaldehyde

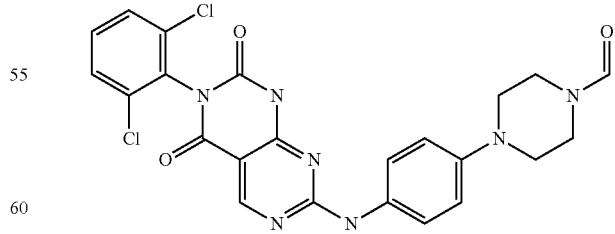

$^1$H-NMR (400 MHz, CDCl$_3$) δ: 10.08 (1H, br), 9.07 (1H, s), 8.10 (1H, s), 7.52-7.48 (3H, m), 7.38 (1H, d, J=7.6 Hz), 6.90 (2H, d, J=8.4 Hz), 3.71 (2H, br), 3.52 (2H, br), 3.16 (2H, br), 3.10 (2H, br).
ESI-MS Found: m/z[M+H] 512

Example 36

3-(2,6-dichlorophenyl)-7-({4-[4-(methoxyacetyl) piperazin-1-yl]phenyl}amino)-1-methylpyrimido[4,5-d]pyrimidine-2,4(1H,3H)-dione

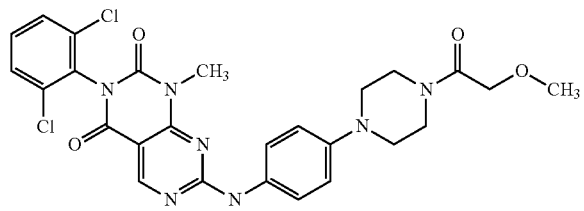 [SMILES: COCC(=O)N1CCN(c2ccc(Nc3ncc4c(=O)n(-c5c(Cl)cccc5Cl)c(=O)n(C)c4n3)cc2)CC1]

$^1$H-NMR (400 MHz, CD$_3$OD) δ: 8.96 (1H, s), 7.65 (2H, br), 7.54-7.52 (3H, m), 7.43 (1H, t, J=7.6 Hz), 7.02 (2H, d, J=8.4 Hz), 4.20 (2H, s), 3.79 (2H, br), 3.67-3.63 (5H, m), 3.46 (3H, s), 3.22 (4H, br).
ESI-MS Found: m/z[M+H] 570

Example 37

3-[2-chloro-6-(hydroxymethyl)phenyl]-7-{[3-methyl-4-(4-methylpiperazin-1-yl)phenyl]amino}pyrimido[4,5-d]pyrimidine-2,4(1H,3H)-dione

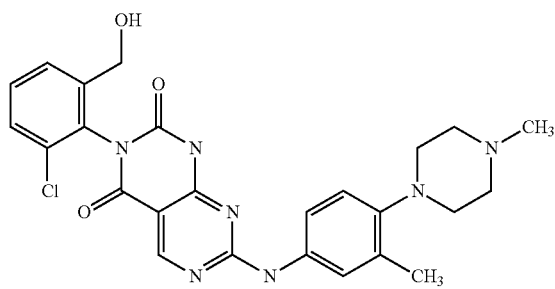 [SMILES: Cc1cc(Nc2ncc3c(=O)n(-c4c(Cl)cccc4CO)c(=O)[nH]c3n2)ccc1N1CCN(C)CC1]

$^1$H-NMR (400 MHz, CD$_3$OD) δ: 8.92 (1H, s), 7.59-7.56 (2H, m), 7.51-7.44 (3H, m), 7.06 (1H, d, J=8.4 Hz), 4.53 (2H, s), 2.97 (4H, br), 2.70 (4H, br), 2.42 (3H, s), 2.33 (3H, s).
ESI-MS Found: m/z[M+H] 508

Example 38

3-(2-chloro-6-fluorophenyl)-7-{[3-methyl-4-(4-methylpiperazin-1-yl)phenyl]amino}pyrimido[4,5-d]pyrimidine-2,4(1H,3H)-dione

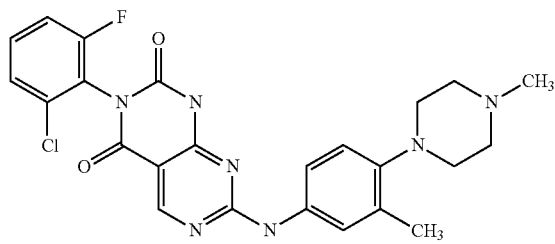 [SMILES: Cc1cc(Nc2ncc3c(=O)n(-c4c(F)cccc4Cl)c(=O)[nH]c3n2)ccc1N1CCN(C)CC1]

$^1$H-NMR (400 MHz, CDCl$_3$) δ: 9.06 (1H, s), 7.45-7.32 (4H, m), 7.21 (1H, t, J=7.6 Hz), 7.00 (1H, d, J=8.4 Hz), 2.91 (4H, br), 2.58 (4H, br), 2.36 (3H, s), 2.27 (3H, s).
ESI-MS Found: m/z[M+H] 496

Example 39

3-(2,6-dichlorophenyl)-7-({4-[3-(2-hydroxyethoxy) azetidin-1-yl]phenyl}amino)pyrimido[4,5-d]pyrimidine-2,4(1H,3H)-dione

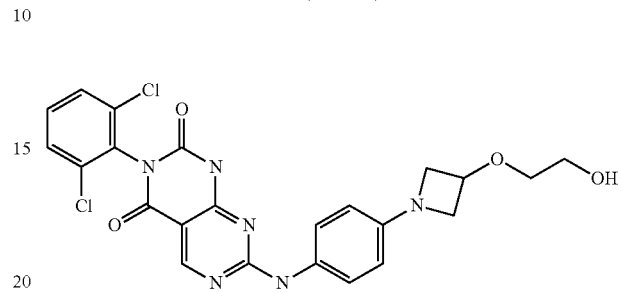

$^1$H-NMR (400 MHz, CD$_3$OD) δ: 8.90 (1H, s), 7.54-7.50 (4H, m), 7.42 (1H, t, J=7.6 Hz), 6.54 (2H, d, J=8.4 Hz), 4.50-4.48 (1H, m), 4.14 (2H, t, J=6.4 Hz), 3.77-3.72 (4H, m), 3.56 (2H, t, J=6.4 Hz).
ESI-MS Found: m/z[M+H] 515

Example 40

7-{[4-(4-acetylpiperazin-1-yl)-3-methylphenyl]amino}-3-(2-chlorophenyl)pyrimido[4,5-d]pyrimidine-2,4(1H,3H)-dione

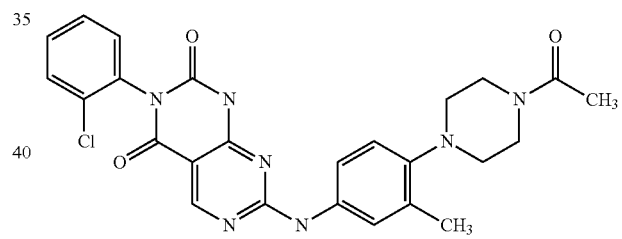

$^1$H-NMR (400 MHz, CDCl$_3$) δ: 10.06 (1H, s), 9.07 (1H, s), 7.62-7.60 (1H, br), 7.59-7.26 (5H, m), 6.93 (1H, d, J=8.8 Hz), 3.74 (2H, br), 3.84 (3H, s), 3.57 (2H, br), 2.84 (4H, br), 2.39 (3H, s), 2.28 (3H, s), 2.14 (3H, s).
ESI-MS Found: m/z[M+H] 506

Example 41

3-(2,6-dichlorophenyl)-7-({4-[3-(dimethylamino) propoxy]phenyl}amino)pyrimido[4,5-d]pyrimidine-2,4(1H,3H)-dione

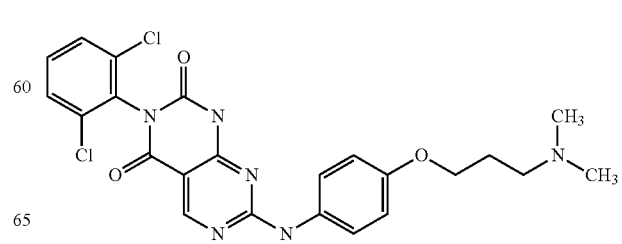

¹H-NMR (400 MHz, DMSO-d₆) δ: 10.28 (1H, br s), 8.79 (1H, s), 8.30 (1H, s), 7.80-7.65 (4H, m), 7.53 (1H, t, J=5.3 Hz), 6.88 (2H, d, J=5.3 Hz), 3.96 (2H, t, J=5.0 Hz), 2.42 (2H, t, J=5.4 Hz), 2.17 (6H, s), 1.86-1.79 (2H, m).

ESI-MS Found: m/z[M+H] 501

Example 42

3-(2-chlorophenyl)-1-ethyl-7-{[3-methyl-4-(4-methylpiperazin-1-yl)phenyl]amino}pyrimido[4,5-d]pyrimidine-2,4(1H,3H)-dione

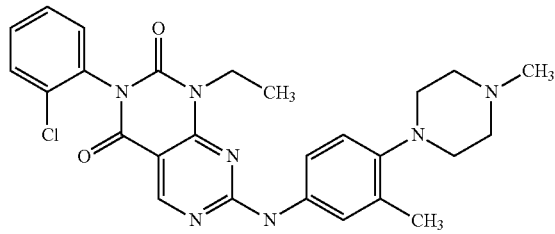 [SMILES: CCn1c(=O)n(-c2ccccc2Cl)c(=O)c2cnc(Nc3ccc(N4CCN(C)CC4)c(C)c3)nc21]

¹H-NMR (400 MHz, CD₃OD) δ: 8.95 (1H, s), 7.68-7.59 (2H, m), 7.49-7.46 (32H, m), 7.40-7.37 (1H, m), 7.08 (1H, d, J=8.4 Hz), 4.36 (2H, q, J=7.6 Hz), 2.98 (4H, br), 2.68 (4H, br), 2.41 (3H, s), 2.35 (3H, s), 1.41 (3H, br).

ESI-MS Found: m/z[M+H] 506

Example 43

3-(2-chloro-6-methylphenyl)-7-({4-[4-(2-hydroxy-2-methylpropyl)piperazin-1-yl]phenyl}amino)pyrimido[4,5-d]pyrimidine-2,4(1H,3H)-dione

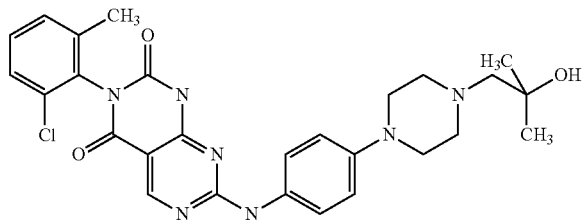 [SMILES: Cc1cccc(Cl)c1-n1c(=O)[nH]c2nc(Nc3ccc(N4CCN(CC(C)(C)O)CC4)cc3)ncc2c1=O]

¹H-NMR (400 MHz, CD₃OD) δ: 8.94 (1H, s), 7.57 (2H, br), 7.39-7.28 (3H, m), 6.96 (1H, d, J=8.4 Hz), 3.20 (4H, br), 2.83 (4H, br), 2.43 (2H, s), 2.23 (3H, s), 1.22 (6H, s).

ESI-MS Found: m/z[M+H] 536

Example 44

3-(2,6-dichlorophenyl)-1-(2-hydroxyethyl)-7-({4-[4-(methoxyacetyl)piperazin-1-yl]phenyl}amino)pyrimido[4,5-d]pyrimidine-2,4(1H,3H)-dione

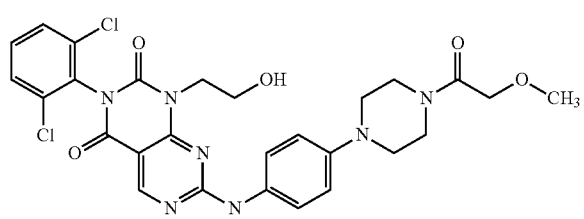 [SMILES: COCC(=O)N1CCN(c2ccc(Nc3ncc4c(=O)n(-c5c(Cl)cccc5Cl)c(=O)n(CCO)c4n3)cc2)CC1]

¹H-NMR (400 MHz, CD₃OD) δ: 8.94 (1H, s), 7.63 (2H, br), 7.54 (2H, d, J=8.4 Hz), 7.45 (1H, t, J=7.4 Hz), 7.00 (2H, d, J=8.4 Hz), 4.46 (2H, t, J=6.4 Hz), 4.21 (2H, s), 3.89 (2H, t, J=6.4 Hz), 3.78 (2H, br), 3.67 (2H, br), 3.45 (3H, s), 3.21 (4H, br).

ESI-MS Found: m/z[M+H] 600

Example 45

3-(2-chlorophenyl)-7-{[4-(4-cyclopropylpiperazin-1-yl)phenyl]amino}pyrimido[4,5-d]pyrimidine-2,4(1H,3H)-dione

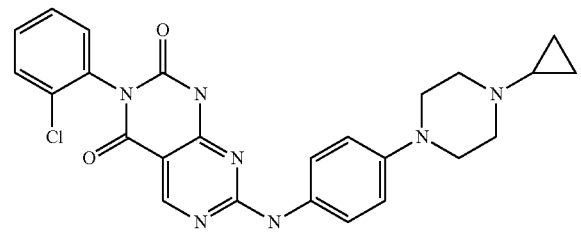 [SMILES: O=c1[nH]c2nc(Nc3ccc(N4CCN(C5CC5)CC4)cc3)ncc2c(=O)n1-c1ccccc1Cl]

¹H-NMR (400 MHz, CD₃OD) δ: 8.82 (1H, s), 7.75-7.60 (2H, m), 7.55-7.50 (4H, m), 6.92 (2H, d, J=8.4 Hz), 3.08 (4H, br), 2.71 (5H, br), 0.45-0.35 (4H, br).

ESI-MS Found: m/z[M+H] 490

Example 46

3-(2,6-difluorophenyl)-7-{[3-methyl-4-(4-methylpiperazin-1-yl)phenyl]amino}pyrimido[4,5-d]pyrimidine-2,4(1H,3H)-dione

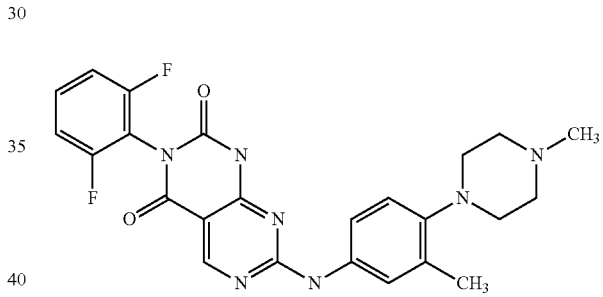

¹H-NMR (400 MHz, CD₃OD) δ: 8.93 (1H, s), 7.54-7.40 (2H, br), 7.15-7.05 (4H, m), 2.95 (4H, br), 2.66 (4H, br), 2.39 (3H, s), 2.34 (3H, s).

ESI-MS Found: m/z[M+H] 480

Example 47

3-[2-(methoxymethyl)-6-methylphenyl]-7-{[3-methyl-4-(4-methylpiperazin-1-yl)phenyl]amino}pyrimido[4,5-d]pyrimidine-2,4(1H,3H)-dione

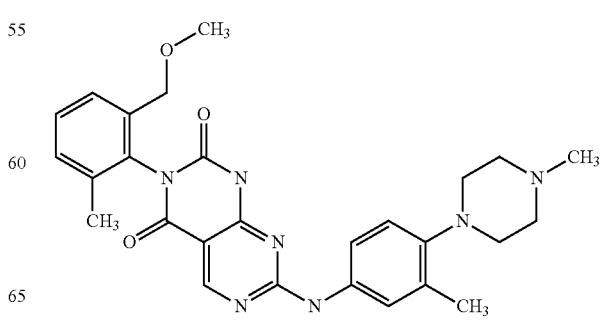

¹H-NMR (400 MHz, CDCl₃) δ: 10.07 (1H, br), 9.05 (1H, s), 7.38-7.29 (4H, m), 6.96 (1H, d, J=8.4 Hz), 4.37 (2H, AB-q, J=12.8 Hz), 3.21 (3H, s), 2.91 (4H, br), 2.58 (4H, br), 2.37 (3H, s), 2.24 (3H, s), 2.21 (3H, s).

ESI-MS Found: m/z[M+H] 502

Example 48

3-[2-(hydroxymethyl)-6-methylphenyl]-7-{[3-methyl-4-(4-methylpiperazin-1-yl)phenyl]amino}pyrimido[4,5-d]pyrimidine-2,4(1H,3H)-dione

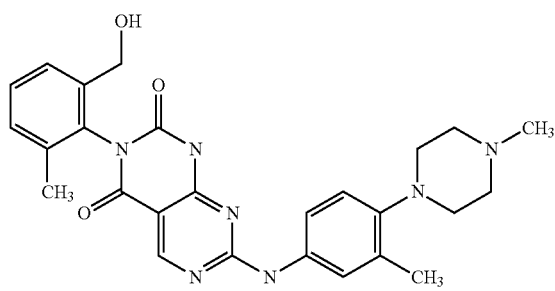 [SMILES: Cc1cc(Nc2ncc3c(=O)n(-c4c(C)cccc4CO)c(=O)[nH]c3n2)ccc1N1CCN(C)CC1]

¹H-NMR (400 MHz, CD₃OD) δ: 8.88 (1H, s), 7.56 (1H, br), 7.51 (1H, br), 7.44-7.36 (2H, m), 7.30 (1H, d, J=7.6 Hz), 7.07 (1H, d, J=8.4 Hz), 4.47 (2H, s), 2.95 (4H, br), 2.69 (4H, br), 2.40 (3H, s), 2.34 (3H, s), 2.14 (3H, s).

ESI-MS Found: m/z[M+H] 488

Example 49

3-(2-iodophenyl)-7-{[3-methyl-4-(4-methylpiperazin-1-yl)phenyl]amino}pyrimido[4,5-d]pyrimidine-2,4(1H,3H)-dione

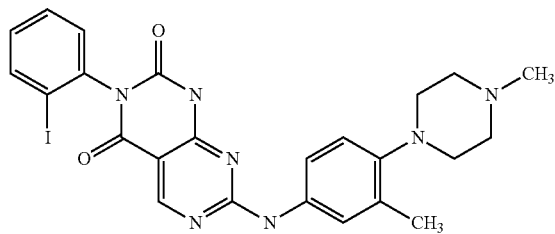 [SMILES: Cc1cc(Nc2ncc3c(=O)n(-c4ccccc4I)c(=O)[nH]c3n2)ccc1N1CCN(C)CC1]

¹H-NMR (400 MHz, CD₃OD) δ: 8.94 (1H, s), 7.98 (1H, d, J=7.6 Hz), 7.51 (1H, t, J=7.6 Hz), 7.44-7.40 (2H, m), 7.31 (1H, d, J=7.6 Hz), 7.19 (1H, t, J=7.6 Hz), 7.05 (1H, d, J=8.4 Hz), 2.94 (4H, br), 2.64 (4H, br), 2.38 (3H, s), 2.33 (3H, s).

ESI-MS Found: m/z[M+H] 570

Example 50

3-(2,6-dichlorophenyl)-7-({4-[2-(dimethylamino)ethoxy]phenyl}amino)pyrimido[4,5-d]pyrimidine-2,4(1H,3H)-dione

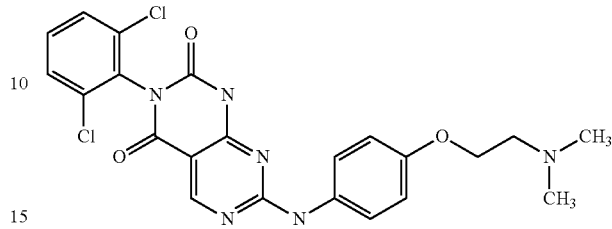

¹H-NMR (400 MHz, DMSO-d₆) δ: 10.35 (1H, br s), 8.84 (1H, s), 8.30 (1H, s), 7.79-7.66 (4H, m), 7.53 (1H, t, J=5.3 Hz), 6.88 (2H, d, J=5.3 Hz), 4.00 (2H, t, J=5.0 Hz), 2.65 (2H, t, J=5.4 Hz), 2.22 (6H, s).

ESI-MS Found: m/z[M+H] 487

Example 51

3-(2-chlorophenyl)-7-{[4-(4-methylpiperazin-1-yl)phenyl]amino}pyrimido[4,5-d]pyrimidine-2,4(1H,3H)-dione

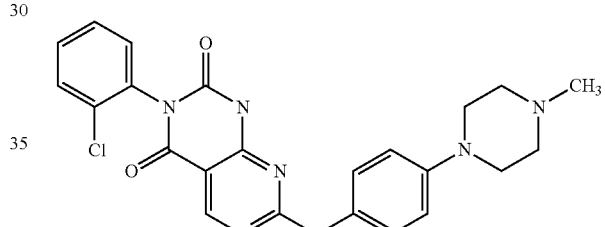

¹H-NMR (400 MHz, CD₃OD) δ: 8.91 (1H, s), 7.58-7.54 (3H, m), 7.45-7.40 (2H, m), 7.34-7.32 (1H, m), 6.98 (2H, d, J=8.4 Hz), 3.21 (4H, br), 2.65 (4H, br), 2.38 (3H, s).

ESI-MS Found: m/z[M+H] 464

Example 52

3-(2-chlorophenyl)-7-({4-[4-(propan-2-yl)piperazin-1-yl]phenyl}amino)pyrimido[4,5-d]pyrimidine-2,4(1H,3H)-dione

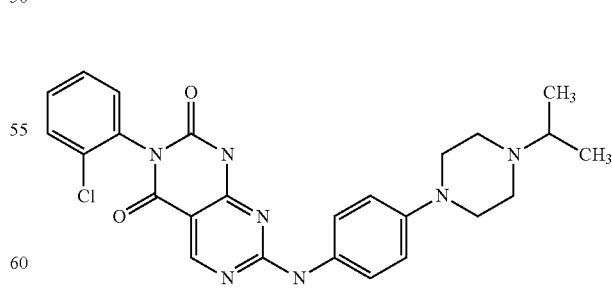

¹H-NMR (400 MHz, CD₃OD) δ: 8.95 (1H, s), 7.60-7.56 (1H, m), 7.50 (2H, d, J=8.4 Hz), 7.45-7.42 (3H, m), 6.94 (2H, d, J=8.4 Hz), 3.20 (4H, br), 2.72 (5H, br), 1.12 (6H, d, J=6.4 Hz).

ESI-MS Found: m/z[M+H] 492

Example 53

3-(2-chlorophenyl)-7-{[3-methoxy-4-(4-methylpiperazin-1-yl)phenyl]amino}pyrimido[4,5-d]pyrimidine-2,4(1H,3H)-dione

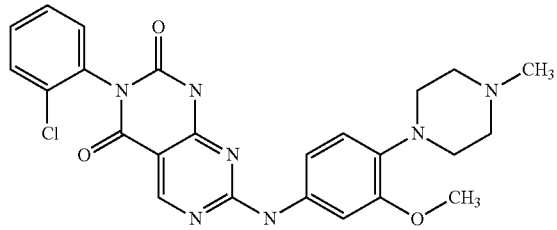 [SMILES: COc1cc(Nc2ncc3c(=O)n(-c4ccccc4Cl)c(=O)[nH]c3n2)ccc1N1CCN(C)CC1]

¹H-NMR (400 MHz, CD₃OD) δ: 8.97 (1H, s), 7.58-7.55 (1H, m), 7.44-7.41 (3H, m), 7.23-7.21 (2H, m), 6.92 (1H, d, J=8.4 Hz), 3.83 (3H, s), 3.07 (4H, br), 2.65 (4H, br), 2.35 (3H, s).
ESI-MS Found: m/z[M+H] 494

Example 54

1-ethyl-3-[2-(fluoromethyl)-6-methylphenyl]-7-{[3-methyl-4-(4-methylpiperazin-1-yl)phenyl]amino}pyrimido[4,5-d]pyrimidine-2,4(1H,3H)-dione

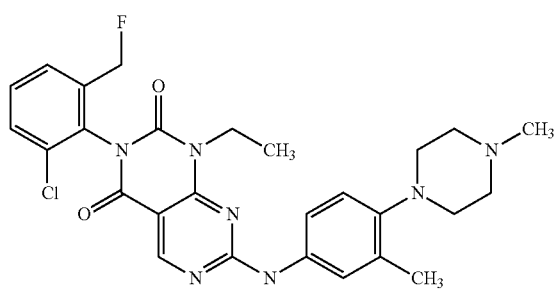 [SMILES: CCn1c(=O)n(-c2c(Cl)cccc2CF)c(=O)c2cnc(Nc3ccc(N4CCN(C)CC4)c(C)c3)nc21]

¹H-NMR (400 MHz, CD₃OD) δ: 8.96 (1H, br), 7.50-7.40 (4H, br), 7.09 (1H, d, J=8.8 Hz), 5.26 (2H, d, J=46 Hz), 4.39-4.35 (2H, m) 2.98 (4H, br), 2.67 (4H, br), 2.39 (3H, s), 2.35 (3H, s), 2.17 (3H, s), 1.40-1.27 (3H, br).
ESI-MS Found: m/z[M+H] 518

Example 55

3-(3,5-dichloropyridin-4-yl)-7-{[3-methyl-4-(4-methylpiperazin-1-yl)phenyl]amino}pyrimido[4,5-d]pyrimidine-2,4(1H,3H)-dione

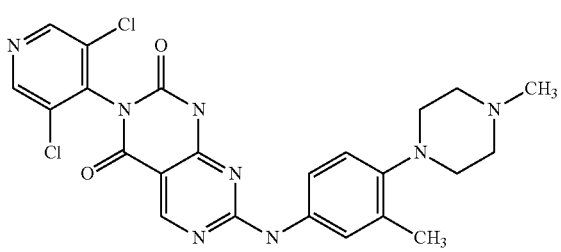 [SMILES: Cc1cc(Nc2ncc3c(=O)n(-c4c(Cl)cncc4Cl)c(=O)[nH]c3n2)ccc1N1CCN(C)CC1]

¹H-NMR (400 MHz, CD₃OD) δ: 8.93 (1H, s), 8.69 (2H, s), 7.50-7.40 (2H, br), 7.06 (1H, d, J=8.8 Hz), 2.96 (4H, br), 2.67 (4H, br), 2.39 (3H, s), 2.34 (3H, s).
ESI-MS Found: m/z[M+H] 513

Example 56

3-(2-methoxy-6-methylphenyl)-7-{[3-methyl-4-(4-methylpiperazin-1-yl)phenyl]amino}pyrimido[4,5-d]pyrimidine-2,4(1H,3H)-dione

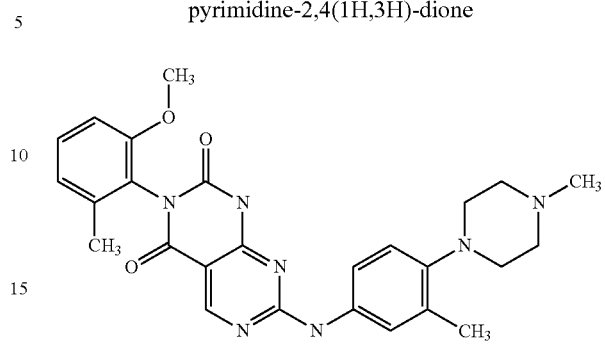

¹H-NMR (400 MHz, CD₃OD) δ: 8.93 (1H, s), 7.58 (2H, br), 7.33 (1H, t, J=7.6 Hz), 7.04 (1H, d, J=7.6 Hz), 6.94 (1H, d, J=7.6 Hz), 6.88 (1H, d, J=8.4 Hz), 3.77 (3H, s), 2.95 (4H, br), 2.66 (4H, br), 2.39 (3H, s), 2.31 (3H, s), 2.16 (3H, s).
ESI-MS Found: m/z[M+H] 487

Example 57

3-(2-chloro-4-fluorophenyl)-7-{[3-methyl-4-(4-methylpiperazin-1-yl)phenyl]amino}pyrimido[4,5-d]pyrimidine-2,4(1H,3H)-dione

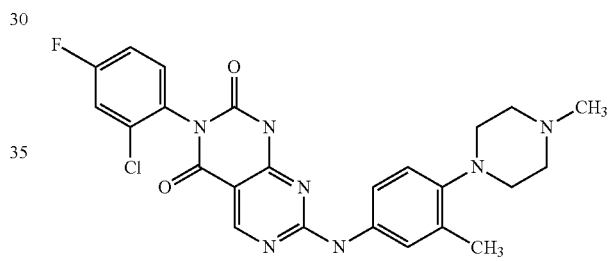

¹H-NMR (400 MHz, CDCl₃) δ: 9.99 (1H, br), 9.05 (1H, s), 7.38-7.30 (5H, m), 7.15 (1H, t, J=7.2 Hz), 6.99 (1H, d, J=8.4 Hz), 2.91 (4H, br), 2.57 (4H, br), 2.36 (3H, s), 2.27 (3H, s).
ESI-MS Found: m/z[M+H] 496

Example 58

7-{[3-methyl-4-(4-methylpiperazin-1-yl)phenyl]amino}-3-(2-methylphenyl)pyrimido[4,5-d]pyrimidine-2,4(1H,3H)-dione

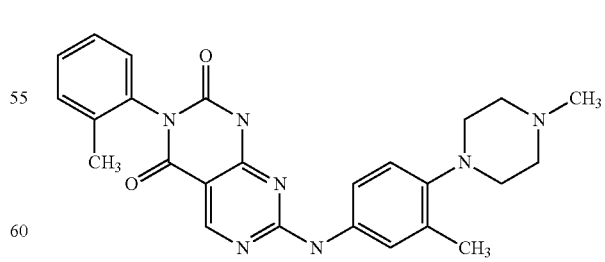

¹H-NMR (400 MHz, CDCl₃) δ: 10.01 (1H, br), 9.06 (1H, s), 7.38-7.30 (5H, m), 7.20 (1H, d, J=7.2 Hz), 6.98 (1H, d, J=8.4 Hz), 2.91 (4H, br), 2.57 (4H, br), 2.36 (3H, s), 2.25 (3H, s), 2.21 (3H, s).
ESI-MS Found: m/z[M+H] 458

Example 59

7-{[3-methyl-4-(4-methylpiperazin-1-yl)phenyl]amino}-3-(2-nitrophenyl)pyrimido[4,5-d]pyrimidine-2,4(1H,3H)-dione

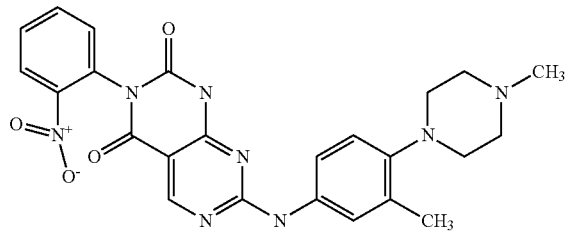 [SMILES: Cc1cc(Nc2ncc3c(=O)n(-c4ccccc4[N+](=O)[O-])c(=O)[nH]c3n2)ccc1N1CCN(C)CC1]

$^1$H-NMR (400 MHz, CDCl$_3$) δ: 9.94 (1H, br), 9.03 (1H, s), 8.29 (1H, d, J=7.6 Hz), 7.81 (1H, t, J=7.6 Hz), 7.69 (1H, t, J=7.6 Hz), 7.50 (1H, d, J=7.6 Hz), 7.31-7.26 (2H, m), 6.96 (1H, d, J=8.4 Hz), 2.90 (4H, br), 2.56 (4H, br), 2.35 (3H, s), 2.26 (3H, s).
ESI-MS Found: m/z[M+H] 489

Example 60 tert-butyl 4-(4-{[6-(2-chlorophenyl)-5,7-dioxo-5,6,7,8-tetrahydropyrimido[4,5-d]pyrimidin-2-yl]amino}-2-methylphenyl)piperazine-1-carboxylate

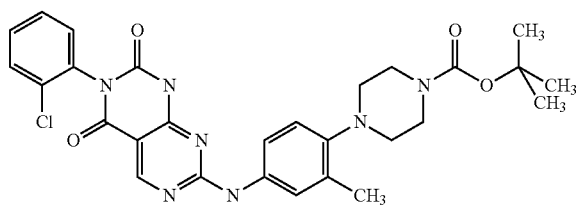 [SMILES: Cc1cc(Nc2ncc3c(=O)n(-c4ccccc4Cl)c(=O)[nH]c3n2)ccc1N1CCN(C(=O)OC(C)(C)C)CC1]

$^1$H-NMR (400 MHz, CDCl$_3$) δ: 9.07 (1H, s), 7.60-7.58 (1H, m), 7.47-7.36 (5H, m), 6.94 (1H, d, J=8.4 Hz), 3.54 (4H, br), 2.81 (4H, br), 2.27 (3H, s), 1.48 (9H, s).
ESI-MS Found: m/z[M+H] 564

Example 61

3-(2-chlorophenyl)-7-({4-[4-(2-methoxyethyl)piperazin-1-yl]phenyl}amino)pyrimido[4,5-d]pyrimidine-2,4(1H,3H)-dione

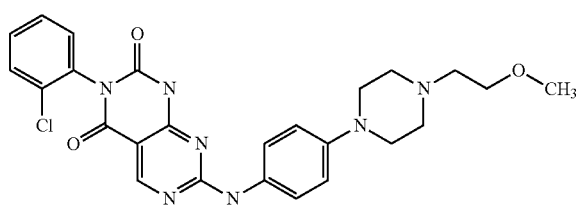 [SMILES: COCCN1CCN(c2ccc(Nc3ncc4c(=O)n(-c5ccccc5Cl)c(=O)[nH]c4n3)cc2)CC1]

$^1$H-NMR (400 MHz, CDCl$_3$) δ: 10.02 (1H, s), 9.05 (1H, s), 7.60-7.58 (1H, m), 7.47-7.36 (4H, m), 7.37-7.33 (1H, m), 6.87 (2H, d, J=8.4 Hz), 3.59 (2H, br), 3.37 (3H, s), 3.22 (4H, br), 2.68 (6H, br).
ESI-MS Found: m/z[M+H] 508

Example 62

2-[7-{[3-methyl-4-(4-methylpiperazin-1-yl)phenyl]amino}-2,4-dioxo-1,4-dihydropyrimido[4,5-d]pyrimidin-3(2H)-yl]benzonitrile

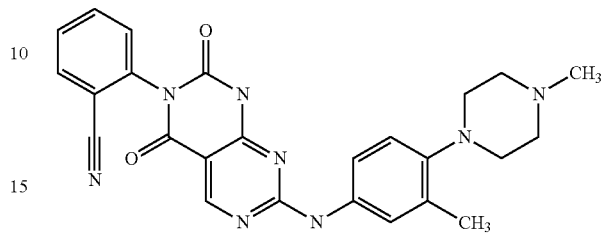

$^1$H-NMR (400 MHz, CD$_3$OD) δ: 8.93 (1H, s), 7.86 (1H, d, J=7.6 Hz), 7.81 (1H, t, J=7.6 Hz), 7.62 (1H, t, J=7.6 Hz), 7.50-7.46 (3H, s), 7.06 (1H, d, J=8.4 Hz), 2.95 (4H, br), 2.66 (4H, br), 2.39 (3H, s), 2.34 (3H, s).
ESI-MS Found: m/z[M+H] 469

Example 63

3-(2-methoxyphenyl)-7-{[3-methyl-4-(4-methylpiperazin-1-yl)phenyl]amino}pyrimido[4,5-d]pyrimidine-2,4(1H,3H)-dione

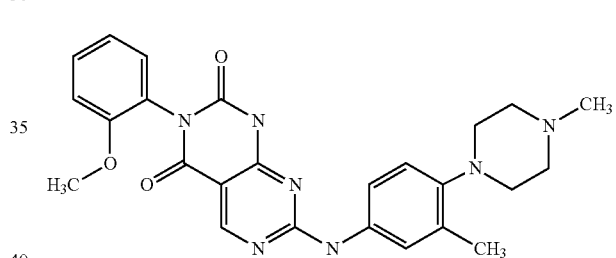

$^1$H-NMR (400 MHz, CD$_3$OD) δ: 8.94 (1H, s), 7.45-7.40 (3H, m), 7.21 (1H, d, J=7.6 Hz), 7.10-7.03 (3H, m), 3.81 (3H, s), 2.94 (4H, br), 2.64 (4H, br), 2.38 (3H, s), 2.32 (3H, s).
ESI-MS Found: m/z[M+H] 474

Example 64

2-[7-{[3-methyl-4-(4-methylpiperazin-1-yl)phenyl]amino}-2,4-dioxo-1,4-dihydropyrimido[4,5-d]pyrimidin-3(2H)-yl]benzamide

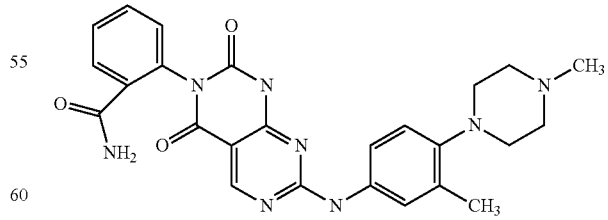

$^1$H-NMR (400 MHz, CD$_3$OD) δ: 8.88 (1H, s), 7.79 (1H, d, J=7.6 Hz), 7.77-7.56 (2H, m), 7.50-7.45 (2H, m), 7.34 (1H, d, J=7.6 Hz), 7.08 (1H, d, J=8.4 Hz), 3.19 (4H, br), 2.91 (4H, br), 2.32 (3H, s).
ESI-MS Found: m/z[M+H] 487

Example 65

3-benzyl-7-{[3-methyl-4-(4-methylpiperazin-1-yl)phenyl]amino}pyrimido[4,5-d]pyrimidine-2,4(1H,3H)-dione

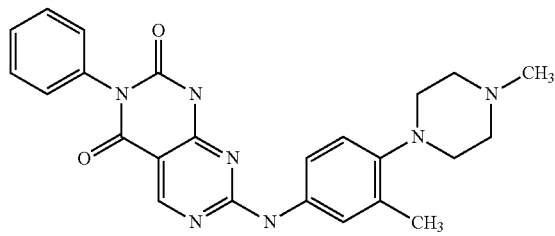 [SMILES: Cc1cc(Nc2ncc3c(=O)n(-c4ccccc4)c(=O)[nH]c3n2)ccc1N1CCN(C)CC1]

¹H-NMR (400 MHz, CDCl₃) δ: 9.03 (1H, s), 7.60-7.50 (4H, m), 7.35-7.26 (3H, m), 7.07 (1H, d, J=8.8 Hz), 5.18 (2H, s), 2.96 (4H, br), 2.57 (4H, br), 2.37 (3H, s), 2.36 (3H, s).
ESI-MS Found: m/z[M+H] 458

Example 66

3-(2-chlorophenyl)-7-{[3-methyl-4-(4-methylpiperazin-1-yl)phenyl]amino}-1-(pyridin-2-yl)pyrimido[4,5-d]pyrimidine-2,4(1H,3H)-dione

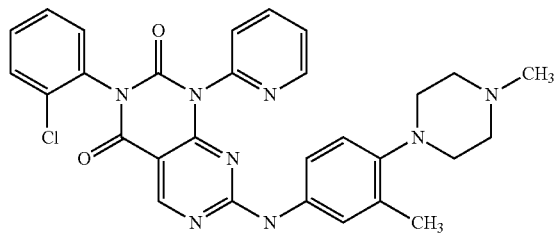 [SMILES: Cc1cc(Nc2ncc3c(=O)n(-c4ccccc4Cl)c(=O)n(-c4ccccn4)c3n2)ccc1N1CCN(C)CC1]

¹H-NMR (400 MHz, CDCl₃) δ: 9.04 (1H, s), 8.76 (1H, s), 7.91 (1H, br), 7.55-7.40 (6H, m), 6.96 (1H, br), 6.91 (1H, br), 6.72 (1H, s), 2.89 (4H, br), 2.63 (4H, br), 2.40 (3H, s), 2.10 (3H, s).
ESI-MS Found: m/z[M+H] 555

Example 67

3-(2-chloropyridin-3-yl)-7-{[3-methyl-4-(4-methylpiperazin-1-yl)phenyl]amino}pyrimido[4,5-d]pyrimidine-2,4(1H,3H)-dione

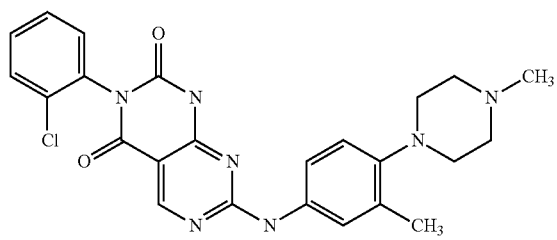

¹H-NMR (400 MHz, CDCl₃) δ: 9.98 (1H, br), 9.06 (1H, s), 8.54 (1H, br), 7.73 (1H, d, J=8.0 Hz), 7.46-7.26 (3H, m), 6.99 (1H, d, J=8.8 Hz), 2.91 (4H, br), 2.58 (4H, br), 2.36 (3H, s), 2.26 (3H, s).
ESI-MS Found: m/z[M+H] 479

Example 68

3-(2-chlorophenyl)-7-{[3-methyl-4-(4-methylpiperazin-1-yl)phenyl]amino}-1-(1-methyl-1H-pyrazol-3-yl)pyrimido[4,5-d]pyrimidine-2,4(1H,3H)-dione

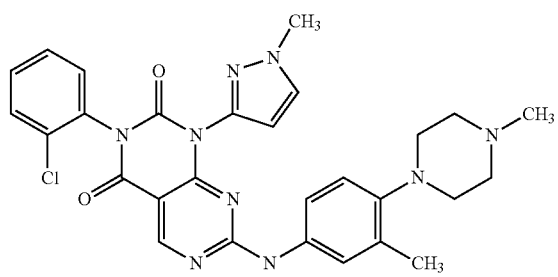 [SMILES: Cc1cc(Nc2ncc3c(=O)n(-c4ccccc4Cl)c(=O)n(-c4ccn(C)n4)c3n2)ccc1N1CCN(C)CC1]

¹H-NMR (400 MHz, CD₃OD) δ: 8.98 (1H, s), 7.72 (1H, br), 7.60-7.57 (1H, m), 7.48-7.40 (4H, m), 7.29 (1H, br), 7.16 (1H, d, J=8.0 Hz), 6.86 (1H, d, J=8.4 Hz), 6.46 (1H, br), 4.01 (3H, s), 2.93 (4H, br), 2.66 (4H, br), 2.41 (3H, s), 2.21 (3H, s).
ESI-MS Found: m/z[M+H] 558

Example 69

7-{[3-methyl-4-(4-methylpiperazin-1-yl)phenyl]amino}-3-(2-phenylethyl)pyrimido[4,5-d]pyrimidine-2,4(1H,3H)-dione

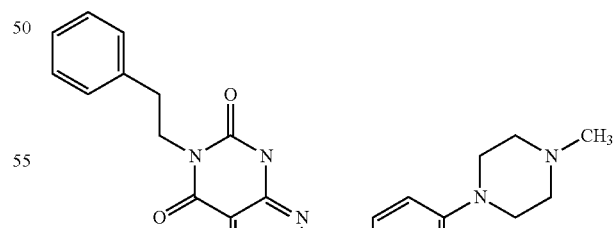

¹H-NMR (400 MHz, CD₃OD) δ: 8.85 (1H, s), 7.55-7.51 (1H, m), 7.44 (1H, br), 7.31-7.29 (4H, m), 7.23-7.20 (1H, m), 7.04 (1H, d, J=8.4 Hz), 4.20-4.16 (2H, m), 2.95 (6H, br), 2.64 (4H, br), 2.39 (3H, s), 2.33 (3H, s).
ESI-MS Found: m/z[M+H] 472

Example 70

3-(2,5-dichlorophenyl)-7-{[3-methyl-4-(4-methylpiperazin-1-yl)phenyl]amino}pyrimido[4,5-d]pyrimidine-2,4(1H,3H)-dione

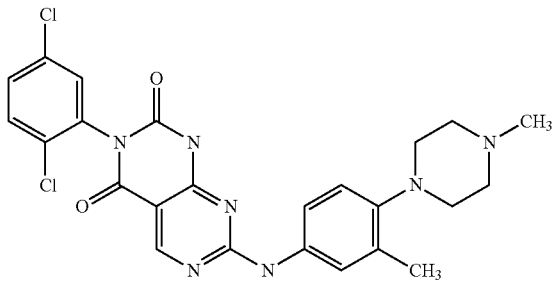 [SMILES: Cc1cc(Nc2ncc3c(=O)n(-c4cc(Cl)ccc4Cl)c(=O)[nH]c3n2)ccc1N1CCN(C)CC1]

$^1$H-NMR (400 MHz, CDCl$_3$) δ: 9.98 (1H, br), 9.05 (1H, s), 7.52 (1H, d, J=8.8 Hz), 7.75-7.31 (4H, m), 6.99 (1H, d, J=8.8 Hz), 2.91 (4H, br), 2.62 (4H, br), 2.38 (3H, s), 2.27 (3H, s).
ESI-MS Found: m/z[M+H] 512

Example 71

7-{[3-methyl-4-(4-methylpiperazin-1-yl)phenyl]amino}-3-(3-methylpyridin-2-yl)pyrimido[4,5-d]pyrimidine-2,4(1H,3H)-dione

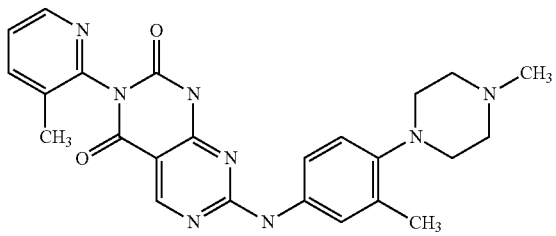

$^1$H-NMR (400 MHz, CD$_3$OD) δ: 8.91 (1H, s), 8.43 (1H, d, J=4.8 Hz), 7.81 (1H, d, J=7.2 Hz), 7.50-7.41 (3H, m), 7.04 (1H, d, J=8.4 Hz), 2.94 (4H, br), 2.66 (4H, br), 2.38 (3H, s), 2.32 (3H, s), 2.25 (3H, s).
ESI-MS Found: m/z[M+H] 459

Example 72

7-{[3-methyl-4-(4-methylpiperazin-1-yl)phenyl]amino}-3-[2-(methylsulfonyl)phenyl]pyrimido[4,5-d]pyrimidine-2,4(1H,3H)-dione

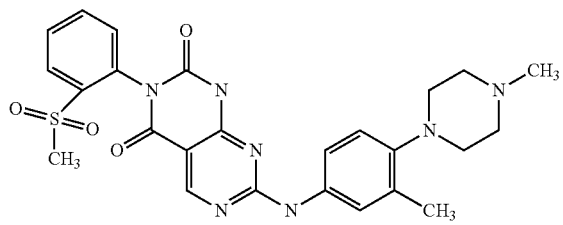 [SMILES: Cc1cc(Nc2ncc3c(=O)n(-c4ccccc4S(C)(=O)=O)c(=O)[nH]c3n2)ccc1N1CCN(C)CC1]

$^1$H-NMR (400 MHz, CD$_3$OD) δ: 8.89 (1H, s), 8.16 (1H, d, J=7.6 Hz), 7.90-7.77 (2H, m), 7.60-7.49 (2H, m), 7.47 (1H, d, J=8.4 Hz), 7.07 (1H, d, J=8.4 Hz), 3.11 (3H, s), 2.97 (4H, br), 2.71 (4H, br), 2.42 (3H, s), 2.34 (3H, s).
ESI-MS Found: m/z[M+H] 522

INDUSTRIAL APPLICABILITY

The compounds of the invention have an excellent Wee1 kinase inhibitory effect, and therefore are useful in the field of medicine, especially in the field of treatment of various cancers.

The invention claimed is:
1. A compound represented by the general formula (I), or a pharmaceutically acceptable salt thereof:

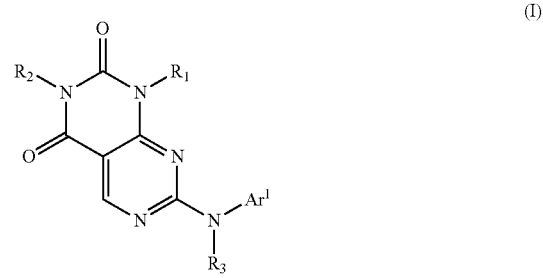

(I)

wherein,
Ar$^1$ is a phenyl group, which is optionally substituted with a substituent selected from the group consisting of a halogen atom, a C1-C6 alkyl group, a halo-C1-C6 alkyl group, a hydroxy-C1-C6 alkyl group, a C1-C6 alkoxy group, a C2-C7 alkanoyl group, a hydroxy-C1-C6 alkylamino group, a carbamoyl group, a hydroxy-C1-C6 alkylcarbamoyl group, a heteroaryl group optionally substituted with a C1-C6 alkyl group, and a group represented by -Q$^1$-A$^1$-Q$^2$-A$^2$(R$^{1a}$)R$^{1b}$;
A$^1$ is a single bond, an oxygen atom or a sulfur atom, or is an imino group optionally substituted with a C1-C6 alkyl group;
A$^2$ is a nitrogen atom, or is a methine group optionally substituted with a hydroxy group, a C1-C6 alkyl group or a hydroxy-C1-C6 alkyl group;
Q$^1$ is a single bond, a carbonyl group or a methylene group optionally substituted with a C1-C6 alkyl group;
Q$^2$ is a single bond or an ethylene or trimethylene group optionally substituted with a C1-C6 alkyl group;
R$^{1a}$ and R$^{1b}$ are each independently a hydrogen atom, a C1-C6 alkyl group or a hydroxy-C1-C6 alkyl group, or together form a C1-C6 alkylene group, wherein one or two or more methylene groups constituting the C1-C6 alkylene group may be independently replaced with an oxygen atom, a sulfur atom, a sulfinyl group, a sulfonyl group, a carbonyl group, a vinylene group or a group represented by —N(R$^{1c}$)—, or substituted with a hydroxy group, a C1-C6 alkyl group or a group represented by —R$^{10c}$;
R$^{1c}$ is a hydrogen atom, a formyl group, a C2-C6 alkenyl group or a group represented by -Q$^3$-A$^3$(R$^{1d}$)R$^{1e}$;
R$^{10c}$ is a group represented by -Q$^{30}$-A$^{30}$(R$^{10d}$)R$^{10e}$;
A$^3$ and A$^{30}$ are each independently a nitrogen atom, or a methine group optionally substituted with a hydroxy group, a C1-C6 alkyl group or a hydroxy-C1-C6 alkyl group;

$Q^3$ and $Q^{30}$ are each independently a single bond or a C1-C6 alkylene group, wherein one or two or more methylene groups constituting the C1-C6 alkylene group may be independently replaced with an oxygen atom, a sulfur atom, a carbonyl group, a sulfinyl group or a sulfonyl group, or substituted with a halogen atom, a cyano group, a hydroxy group or a C1-C6 alkyl group;

$R^{1d}$ and $R^{1e}$ are each independently a hydrogen atom, a halogen atom, a cyano group, a hydroxy group, a C1-C6 alkyl group or a hydroxy-C1-C6 alkyl group, or together form a C1-C6 alkylene group, wherein one or two or more methylene groups constituting the C1-C6 alkylene group may be independently replaced with an oxygen atom, a sulfur atom, a sulfinyl group, a sulfonyl group, a carbonyl group, a vinylene group or a group represented by —N($R^{1f}$)—, or substituted with a hydroxy group or a C1-C6 alkyl group;

$R^{1f}$ and $R^{10f}$ are each independently a hydrogen atom, a C1-C6 alkyl group, a halo-C1-C6 alkyl group, a C2-C6 alkenyl group or a C2-C7 alkanoyl group;

$R^{10d}$ and $R^{10e}$ are each independently a hydrogen atom, a halogen atom, a cyano group, a hydroxy group, a C1-C6 alkyl group or a hydroxy-C1-C6 alkyl group, or together form a C1-C6 alkylene group, wherein one or two or more methylene groups constituting the C1-C6 alkylene group may be independently replaced with an oxygen atom, a sulfur atom, a sulfinyl group, a sulfonyl group, a carbonyl group, a vinylene group or a group represented by —N($R^{10f}$)—, or substituted with a hydroxy group or a C1-C6 alkyl group;

$R^1$ is a hydrogen atom, or is a C1-C6 alkyl group which is optionally substituted with a substituent selected from the group consisting of a halogen atom, a hydroxy group, a cyano group, a C1-C6 alkoxy group, a C3-C6 cycloalkyl group, a C2-C7 alkanoyl group and a C1-C6 alkylsulfonyl group, or is an aryl, aralkyl or heteroaryl group which is optionally substituted with a substituent selected from the group consisting of a halogen atom, a hydroxy group, a cyano group, an amino group, a C1-C6 alkyl group, a C1-C6 alkoxy group, a halo-C1-C6 alkyl group and a hydroxy-C1-C6 alkyl group;

$R^2$ is a C1-C6 alkyl group substituted with one or two phenyl groups, or is a group represented by the formula (a):

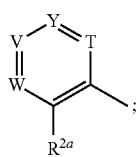

(a)

$R^{2a}$ is a hydrogen atom, a halogen atom, a hydroxy group, a cyano group, an amino group, a nitro group, a carbamoyl group, a C1-C6 alkyl group, a C1-C6 alkylsulfonyl group, a C1-C6 alkoxy group, a halo-C1-C6 alkyl group, a hydroxy-C1-C6 alkyl group or a C1-C6 alkoxy-C1-C6 alkyl group;

T, U, V and W are each independently a methine group, which is optionally substituted with a substituent selected from the group consisting of a halogen atom, a hydroxy group, a cyano group, an amino group, a nitro group, a carbamoyl group, a C1-C6 alkyl group, a C1-C6 alkylsulfonyl group, a C1-C6 alkoxy group, a halo-C1- C6 alkyl group, a hydroxy-C1-C6 alkyl group and a C1-C6 alkoxy-C1-C6 alkyl group, or one of T, U, V, and W is a nitrogen atom; and $R^3$ is a hydrogen atom or a C1-C6 alkyl group.

2. The compound according to claim 1, or a pharmaceutically acceptable salt thereof, wherein the compound is represented by the general formula (I-1):

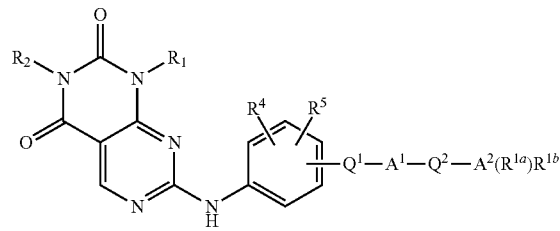

(I-1)

wherein, $A^1$ is a single bond, an oxygen atom or a sulfur atom, or is an imino group optionally substituted with a C1-C6 alkyl group;

$A^2$ is a nitrogen atom, or is a methine group optionally substituted with a hydroxy group, a C1-C6 alkyl group or a hydroxy-C1-C6 alkyl group;

$Q^1$ is a single bond, a carbonyl group or a methylene group optionally substituted with a C1-C6 alkyl group;

$Q^2$ is a single bond or an ethylene or trimethylene group optionally substituted with a C1-C6 alkyl group;

$R^{1a}$ and $R^{1b}$ are each independently a hydrogen atom, a C1-C6 alkyl group or a hydroxy-C1-C6 alkyl group, or together form a C1-C6 alkylene group, wherein one or two or more methylene groups constituting the C1-C6 alkylene group may be independently replaced with an oxygen atom, a sulfur atom, a sulfinyl group, a sulfonyl group, a carbonyl group, a vinylene group or a group represented by —N($R^{1c}$)—, or substituted with a hydroxy group, a C1-C6 alkyl group or a group represented by —$R^{10c}$;

$R^{1c}$ is a hydrogen atom, a formyl group, a C2-C6 alkenyl group or a group represented by -$Q^3$-$A^3$($R^{1d}$)$R^{1e}$;

$R^{10c}$ is a group represented by -$Q^{30}$-$A^{30}$($R^{10d}$)$R^{10e}$;

$A^3$ and $A^{30}$ are each independently a nitrogen atom, or is a methine group optionally substituted with a hydroxy group, a C1-C6 alkyl group or a hydroxy-C1-C6 alkyl group;

$Q^3$ and $Q^{30}$ are each independently a single bond or a C1-C6 alkylene group, wherein one or two or more methylene groups constituting the C1-C6 alkylene group may be independently replaced with an oxygen atom, a sulfur atom, a carbonyl group, a sulfinyl group or a sulfonyl group, or substituted with a halogen atom, a cyano group, a hydroxy group or a C1-C6 alkyl group;

$R^{1d}$ and $R^{1e}$ are each independently a hydrogen atom, a halogen atom, a cyano group, a hydroxy group, a C1-C6 alkyl group or a hydroxy-C1-C6 alkyl group, or together form a C1-C6 alkylene group, wherein one or two or more methylene groups constituting the C1-C6 alkylene group may be independently replaced with an oxygen atom, a sulfur atom, a sulfinyl group, a sulfonyl group, a carbonyl group, a vinylene group or a group represented by —N($R^{1f}$)—, or substituted with a hydroxy group or a C1-C6 alkyl group;

$R^{1f}$ and $R^{10f}$ are each independently a hydrogen atom, a C1-C6 alkyl group, a halo-C1-C6 alkyl group, a C2-C6 alkenyl group or a C2-C7 alkanoyl group;

$R^{10d}$ and $R^{10e}$ are each independently a hydrogen atom, a halogen atom, a cyano group, a hydroxy group, a C1-C6 alkyl group or a hydroxy-C1-C6 alkyl group, or together form a C1-C6 alkylene group, wherein one or two or more methylene groups constituting the C1-C6 alkylene group may be independently replaced with an oxygen atom, a sulfur atom, a sulfinyl group, a sulfonyl group, a carbonyl group, a vinylene group or a group represented by —N($R^{10f}$)—, or substituted with a hydroxy group or a C1-C6 alkyl group;

$R^1$ is a hydrogen atom, or is a C1-C6 alkyl group which is optionally substituted with a substituent selected from the group consisting of a halogen atom, a hydroxy group, a cyano group, a C1-C6 alkoxy group, a C3-C6 cycloalkyl group, a C2-C7 alkanoyl group and a C1-C6 alkylsulfonyl group, or is an aryl, aralkyl or heteroaryl group which is optionally substituted with a substituent selected from the group consisting of a halogen atom, a hydroxy group, a cyano group, an amino group, a C1-C6 alkyl group, a C1-C6 alkoxy group, a halo-C1-C6 alkyl group and a hydroxy-C1-C6 alkyl group;

$R^2$ is a C1-C6 alkyl group substituted with one or two phenyl groups, or denotes a group represented by the formula (a):

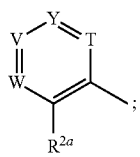

(a)

$R^{2a}$ is a hydrogen atom, a halogen atom, a hydroxy group, a cyano group, an amino group, a nitro group, a carbamoyl group, a C1-C6 alkyl group, a C1-C6 alkylsulfonyl group, a C1-C6 alkoxy group, a halo-C1-C6 alkyl group, a hydroxy-C1-C6 alkyl group or a C1-C6 alkoxy-C1-C6 alkyl group;

T, U, V and W are each independently a methine group which is optionally substituted with a substituent selected from the group consisting of a halogen atom, a hydroxy group, a cyano group, an amino group, a nitro group, a carbamoyl group, a C1-C6 alkyl group, a C1-C6 alkylsulfonyl group, a C1-C6 alkoxy group, a halo-C1-C6 alkyl group, a hydroxy-C1-C6 alkyl group and a C1-C6 alkoxy-C1-C6 alkyl group, or one of T, U, V, and W is a nitrogen atom; and $R^4$ and $R^5$ are each independently a hydrogen atom, a halogen atom, a C1-C6 alkyl group, a halo-C1-C6 alkyl group, a hydroxy-C1-C6 alkyl group, a C1-C6 alkoxy group, a C2-C7 alkanoyl group, a hydroxy-C1-C6 alkylamino group, a carbamoyl group or a hydroxy-C1-C6 alkylcarbamoyl group.

3. The compound according to claim 2, or a pharmaceutically acceptable salt thereof, wherein $R^2$ is a group represented by formula (a), $R^{2a}$ is a halogen atom, and T is a methine group substituted with halogen atom or a C1-C6 alkyl group.

4. The compound according to claim 2, or a pharmaceutically acceptable salt thereof, wherein $R^1$ is a hydrogen atom or a C1-C6 alkyl group optionally substituted with a halogen atom or a hydroxy group.

5. The compound according to claim 3, or a pharmaceutically acceptable salt thereof, wherein $R^2$ is a 2,6-dichlorophenyl group or a 2-chloro-6-methylphenyl group.

6. The compound according to claim 4, or a pharmaceutically acceptable salt thereof, wherein $R^1$ is a hydrogen atom.

7. The compound according to claim 2, or a pharmaceutically acceptable salt thereof, wherein in the group represented by -$Q^1$-$A^1$-$Q^2$-$A^2$($R^{1a}$)$R^{1b}$, (i) $A^1$, $Q^1$ and $Q^2$ are a single bond, $A^2$ is a nitrogen atom, and $R^{1a}$ and $R^{1b}$ together form a C1-C6 alkylene group, wherein one or two methylene groups constituting the C1-C6 alkylene group may be independently replaced with an oxygen atom, a sulfonyl group, a carbonyl group or a group represented by —N($R^{1c}$)—, or substituted with a hydroxy group;

(ii) $A^1$, $Q^1$ and $Q^2$ are a single bond, $A^2$ is a nitrogen atom, and $R^{1a}$ and $R^{1b}$ together form a C1-C6 alkylene group, wherein one or two methylene groups constituting the C1-C6 alkylene group may be independently substituted with a hydroxy group, a C1-C6 alkyl group or —$R^{10c}$;

(iii) $A^1$, $Q^1$ and $Q^2$ are a single bond, $A^2$ is a methine group optionally substituted with a hydroxy group, and $R^{1a}$ and $R^{1b}$ together form a C1-C6 alkylene group, wherein one methylene group constituting the C1-C6 alkylene group is replaced with a group represented by —N($R^{1c}$)—;

(iv) $A^1$ is an oxygen atom, $A^2$ is a methine group, $Q^1$ and $Q^2$ are a single bond, and $R^{1a}$ and $R^{1b}$ together form a C1-C6 alkylene group, wherein one methylene group constituting the C1-C6 alkylene group is replaced with a group represented by —N($R^{1c}$)—;

(v) $A^1$ is an oxygen atom, $A^2$ is a nitrogen atom, $Q^1$ is a single bond, $Q^2$ is an ethylene group or a trimethylene group, and $R^{1a}$ and $R^{1b}$ are independently a C1-C6 alkyl group; or (vi) $A^1$ and $Q^2$ are a single bond, $A^2$ is a nitrogen atom, $Q^1$ is a methylene group, and $R^{1a}$ and $R^{1b}$ together form a C1-C6 alkylene group, wherein one methylene group constituting the C1-C6 alkylene group is replaced with a group represented by —N($R^{1c}$)—.

8. The compound according to claim 2, or a pharmaceutically acceptable salt thereof, wherein $R^1$ is a hydrogen atom or a C1-C6 alkyl group optionally substituted with a hydroxy group, $R^2$ is a 2,6-dichlorophenyl group or a 2-chloro-6-methylphenyl group, and the group represented by -$Q^1$-$A^1$-$Q^2$-$A^2$($R^{1a}$)$R^{1b}$ is a group selected from groups represented by the formula (aa1'):

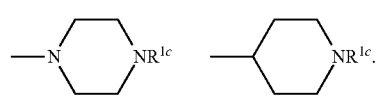

(aa1')

9. The compound according to claim 8, or a pharmaceutically acceptable salt thereof, wherein $R^{1c}$ is a hydrogen atom or a group represented by $Q^3$-$A^3$($R^{1d}$)$R^{1e}$, and in the group represented by -$Q^3$-$A^3$($R^{1d}$)$R^{1e}$, (i) $A^3$ is a methine group optionally substituted with a hydroxy group or a C1-C6 alkyl group, $Q^3$ is a single bond, and $R^{1d}$ and $R^{1e}$ are independently a hydrogen atom or a $C_1$-$C_6$ alkyl group;

(ii) $A^3$ is a methine group, $Q^3$ is a single bond or a C1-C6 alkylene group, and $R^{1d}$ and $R^{1e}$ together form a C1-C6 alkylene group, wherein one methylene group constituting the C1-C6 alkylene group may be replaced with a group represented by —N(R$^{1f}$)—;

(iii) A$^3$ is a methine group optionally substituted with a hydroxy group or a C1-C6 alkyl group, Q$^3$ is a C1-C6 alkylene group, wherein one or two methylene groups constituting the C1-C6 alkylene group may be independently replaced with an oxygen atom, a carbonyl group or a sulfonyl group, or substituted with a hydroxy group, and R$^{1d}$ and R$^{1e}$ are independently a hydrogen atom, a halogen atom, a cyano group or a C1-C6 alkyl group; or (iv) A$^3$ is a nitrogen atom, Q$^3$ is a C1-C6 alkylene group, wherein one methylene group constituting the C1-C6 alkylene group is replaced with a carbonyl group, and R$^{1d}$ and R$^{1e}$ are independently a hydrogen atom or a C1-C6 alkyl group.

10. The compound according to claim 1, or a pharmaceutically acceptable salt thereof, wherein the compound is:

(1) 3-(2,6-dichlorophenyl)-7-{[3-methyl-4-(4-methylpiperazin-1-yl)phenyl]amino}pyrimido[4,5-d]pyrimidine-2,4(1H,3H)-dione;

(2) 3-(2-chloro-6-methylphenyl)-7-{[3-methyl-4-(4-methylpiperazin-1-yl)phenyl]amino}pyrimido[4,5-d]pyrimidine-2,4(1H,3H)-dione;

(3) 3-(2,6-dichlorophenyl)-1-methyl-7-{[3-methyl-4-(4-methylpiperazin-1-yl)phenyl]amino}pyrimido[4,5-d]pyrimidine-2,4(1H,3H)-dione;

(4) 3-(2,6-dichlorophenyl)-1-methyl-7-{[4-(4-methylpiperazin-1-yl)phenyl]amino}pyrimido[4,5-d]pyrimidine-2,4(1H,3H)-dione;

(5) 3-(2,6-dichlorophenyl)-1-(1-methyl-1H-pyrazol-3-yl)-7-{[3-methyl-4-(4-methylpiperazin-1-yl)phenyl]amino}pyrimido[4,5-d]pyrimidine-2,4(1H,3H)-dione;

(6) 3-(2,6-dichlorophenyl)-1-(2-hydroxyethyl)-7-{[3-methyl-4-(4-methylpiperazin-1-yl)phenyl]amino}pyrimido[4,5-d]pyrimidine-2,4(1H,3H)-dione;

(7) 3-(2,4-dichloropyridin-3-yl)-7-{[3-methyl-4-(4-methylpiperazin-1-yl)phenyl]amino}pyrimido[4,5-d]pyrimidine-2,4(1H,3H)-dione;

(8) 3-(2,6-dichlorophenyl)-1-ethyl-7-{[4-(4-methylpiperazin-1-yl)phenyl]amino}pyrimido[4,5-d]pyrimidine-2,4(1H,3H)-dione;

(9) 7-{[4-(4-acetylpiperazin-1-yl)-3-methylphenyl]amino}-3-(2,6-dichlorophenyl)pyrimido[4,5-d]pyrimidine-2,4(1H,3H)-dione;

(10) 7-({4-[4-(1-acetylazetidin-3-yl)piperazin-1-yl]phenyl}amino)-3-(2,6-dichlorophenyl)-1-methylpyrimido[4,5-d]pyrimidine-2,4(1H,3H)-dione;

(11) 3-(2,6-dichlorophenyl)-7-({4-[4-(2-hydroxy-2-methylpropyl)piperazin-1-yl]phenyl}amino)pyrimido[4,5-d]pyrimidine-2,4(1H,3H)-dione;

(12) 3-(2,6-dichlorophenyl)-7-[(4-{4-[(dimethylamino)acetyl]piperazin-1-yl}phenyl)amino}pyrimido[4,5-d]pyrimidine-2,4(1H,3H)-dione;

(13) 3-(2-chlorophenyl)-1-methyl-7-{[3-methyl-4-(4-methylpiperazin-1-yl)phenyl]amino}pyrimido[4,5-d]pyrimidine-2,4(1H,3H)-dione;

(14) 3-(2,6-dichlorophenyl)-7-{[4-(4-methypiperazin-1-yl)phenyl]amino}pyrimido[4,5-d]pyrimidine-2,4(1H,3H)-dione;

(15) 7-{[4-(1-acetylpiperidin-4-yl)phenyl]amino}-3-(2,6-dichlorophenyl)-1-methylpyrimido[4,5-d]pyrimidine-2,4(1H,3H)-dione;

(16) 3-(2,6-dichlorophenyl)-7-{[4-(3-hydroxyazetidin-1-yl)-3-methylphenyl]amino}pyrimido[4,5-d]pyrimidine-2,4(1H,3H)-dione;

(17) 3-(2,6-dichlorophenyl)-7-{[4-(4-hydroxypiperidin-1-yl)-3-methylphenyl]amino}pyrimido[4,5-d]pyrimidine-2,4(1H,3H)-dione;

(18) 7-{[4-(4-acetylpiperazin-1-yl)phenyl]amino}-1-ethyl-3-(2,6-dichlorophenyl)pyrimido[4,5-d]pyrimidine-2,4(1H,3H)-dione;

(19) 3-(2,6-dichlorophenyl)-7-({4-[4-(difluoroacetyl)piperazin-1-yl]phenyl}amino)pyrimido[4,5-d]pyrimidine-2,4(1H,3H)-dione;

(20) 3-(2-chlorophenyl)-7-{[3-methyl-4-(piperazin-1-yl)phenyl]amino}pyrimido[4,5-d]pyrimidine-2,4(1H,3H)-dione;

(21) 7-{[4-(4-acetylpiperidin-1-yl)phenyl]amino}-3-(2,6-dichlorophenyl)pyrimido[4,5-d]pyrimidine-2,4(1H,3H)-dione;

(22) 3-(2-chlorophenyl)-7-{[3-methyl-4-(4-methylpiperazin-1-yl)phenyl]amino}pyrimido[4,5-d]pyrimidine-2,4(1H,3H)-dione;

(23) 3-(2,6-dichlorophenyl)-7-({4-[(4-methylpiperazin-1-yl)methyl]phenyl}amino)pyrimido[4,5-d]pyrimidine-2,4(1H,3H)-dione;

(24) 3-(2,6-dichlorophenyl)-7-({4-[4-(2-hydroxy-2-methylpropionyl)piperazin-1-yl]phenyl}amino)pyrimido[4,5-d]pyrimidine-2,4(1H,3H)-dione;

(25) 3-(2,6-dichlorophenyl)-7-({4-[4-(2-hydroxypropan-2-yl)piperidin-1-yl]phenyl}amino)pyrimido[4,5-d]pyrimidine-2,4(1H,3H)-dione;

(26) 7-{[4-(4-acetylpiperazin-1-yl)phenyl]amino}-3-(2,6-dichlorophenyl)pyrimido[4,5-d]pyrimidine-2,4(1H,3H)-dione;

(27) 3-(2,6-dichlorophenyl)-7-({4-[4-(methoxyacetyl)piperazin-1-yl]phenyl}amino)pyrimido[4,5-d]pyrimidine-2,4(1H,3H)-dione;

(28) 7-{[4-(4-acetyl-1,4-diazepan-1-yl)phenyl]amino}-3-(2,6-dichlorophenyl)pyrimido[4,5-d]pyrimidine-2,4(1H,3H)-dione;

(29) 2-[4-(4-{[6-(2,6-dichlorophenyl)-5,7-dioxo-5,6,7,8-tetrahydropyrimido[4,5-d]pyrimidin-2-yl]amino}phenyl)piperazin-1-yl]-N,N-dimethylacetamide;

(30) 3-(2,6-dichlorophenyl)-7-(phenylamino)pyrimido[4,5-d]pyrimidine-2,4(1H,3H)-dione;

(31) 3-(2,6-dichlorophenyl)-7-{[4-(4-methyl-1,4-diazepan-1-yl)phenyl]amino}pyrimido[4,5-d]pyrimidine-2,4(1H,3H)-dione;

(32) 3-(2,6-dichlorophenyl)-7-({4-[4-(hydroxyacetyl)piperazin-1-yl]phenyl}amino)pyrimido[4,5-d]pyrimidine-2,4(1H,3H)-dione;

(33) 3-(2,6-dichlorophenyl)-7-({4-[4-(2-methoxy-2-methylpropionyl)piperazin-1-yl]phenyl}amino)pyrimido[4,5-d]pyrimidine-2,4(1H,3H)-dione;

(34) ethyl 1-(4-{[6-(2,6-dichlorophenyl)-5,7-dioxo-5,6,7,8-tetrahydropyrimido[4,5-d]pyrimidin-2-yl]amino}phenyl)piperidine-4-carboxylate;

(35) 4-(4-{[6-(2,6-dichlorophenyl)-5,7-dioxo-5,6,7,8-tetrahydropyrimido[4,5-d]pyrimidin-2-yl]amino}phenyl)piperazine-1-carbaldehyde;

(36) 3-(2,6-dichlorophenyl)-7-({4-[4-(2-methoxyacetyl)piperazin-1-yl]phenyl}amino)-1-methylpyrimido[4,5-d]pyrimidine-2,4(1H,3H)-dione;

(37) 3-[2-chloro-6-(hydroxymethyl)phenyl]-7-{[3-methyl-4-(4-methylpiperazin-1-yl)phenyl]amino}pyrimido[4,5-d]pyrimidine-2,4(1H,3H)-dione;

(38) 3-(2-chloro-6-fluorophenyl)-7-{[3-methyl-4-(4-methylpiperazin-1-yl)phenyl]amino}pyrimido[4,5-d]pyrimidine-2,4(1H,3H)-dione;

(39) 3-(2,6-dichlorophenyl)-7-({4-[3-(2-hydroxyethoxy) azetidin-1-yl]phenyl}amino)pyrimido[4,5-d]pyrimidine-2,4(1H,3H)-dione;

(40) 7-{[4-(4-acetylpiperazin-1-yl)-3-methylphenyl]amino}-3-(2-chlorophenyl)pyrimido[4,5-d]pyrimidine-2,4(1H,3H)-dione;

(41) 3-(2,6-dichlorophenyl)-7-({4-[3-(dimethylamino) propoxy]phenyl}amino)pyrimido[4,5-d]pyrimidine-2, 4(1H,3H)-dione;

(42) 3-(2-chlorophenyl)-1-ethyl-7-{[3-methyl-4-(4-methylpiperazin-1-yl)phenyl]amino}pyrimido[4,5-d]pyrimidine-2,4(1H,3H)-dione;

(43) 3-(2-chloro-6-methylphenyl)-7-({4-[4-(2-hydroxy-2-methylpropyl)piperazin-1-yl]phenyl}amino)pyrimido[4,5-d]pyrimidine-2,4(1H,3H)-dione;

(44) 3-(2,6-dichlorophenyl)-1-(2-hydroxyethyl)-7-({4-[4-(methoxyacetyl)piperazin-1-yl]phenyl}amino)pyrimido[4,5-d]pyrimidine-2,4(1H,3H)-dione;

(45) 3-(2-chlorophenyl)-7-{[4-(4-cyclopropylpiperazin-1-yl)phenyl]amino}pyrimido[4,5-d]pyrimidine-2,4 (1H,3H)-dione;

(46) 3-(2,6-difluorophenyl)-7-{[3-methyl-4-(4-methylpiperazin-1-yl)phenyl]amino}pyrimido[4,5-d]pyrimidine-2,4(1H,3H)-dione;

(47) 3-[2-(methoxymethyl)-6-methylphenyl]-7-{[3-methyl-4-(4-methylpiperazin-1-yl)phenyl]amino}pyrimido[4,5-d]pyrimidine-2,4(1H,3H)-dione;

(48) 3-[2-(hydroxymethyl)-6-methylphenyl]-7-{[3-methyl-4-(4-methylpiperazin-1-yl)phenyl]amino}pyrimido[4,5-d]pyrimidine-2,4(1H,3H)-dione;

(49) 3-(2-iodophenyl)-7-{[3-methyl-4-(4-methylpiperazin-1-yl)phenyl]amino}pyrimido[4,5-d]pyrimidine-2, 4(1H,3H)-dione;

(50) 3-(2,6-dichlorophenyl)-7-({4-[2-(dimethylamino) ethoxy]phenyl}amino)pyrimido[4,5-d]pyrimidine-2,4 (1H,3H)-dione;

(51) 3-(2-chlorophenyl)-7-{[4-(4-methylpiperazin-1-yl) phenyl]amino}pyrimido[4,5-d]pyrimidine-2,4(1H, 3H)-dione;

(52) 3-(2-chlorophenyl)-7-({4-[4-(propan-2-yl)piperazin-1-yl]phenyl]amino}pyrimido[4,5-d]pyrimidine-2,4 (1H,3H)-dione;

(53) 3-(2-chlorophenyl)-7-{[3-methoxy-4-(4-methylpiperazin-1-yl)phenyl]amino}pyrimido[4,5-d]pyrimidine-2,4(1H,3H)-dione;

(54) 1-ethyl-3-[2-(fluoromethyl)-6-methylphenyl]-7-{[3-methyl-4-(4-methylpiperazin-1-yl)phenyl]amino}pyrimido[4,5-d]pyrimidine-2,4(1H,3H)-dione;

(55) 3-(3,5-dichloropyridin-4-yl)-7-{[3-methyl-4-(4-methylpiperazin-1-yl)phenyl]amino}pyrimido[4,5-d]pyrimidine-2,4(1H,3H)-dione;

(56) 3-(2-methoxy-6-methylphenyl)-7-{[3-methyl-4-(4-methylpiperazin-1-yl)phenyl]amino}pyrimido[4,5-d] pyrimidine-2,4(1H,3H)-dione;

(57) 3-(2-chloro-4-fluorophenyl)-7-{[3-methyl-4-(4-methylpiperazin-1-yl)phenyl]amino}pyrimido[4,5-d]pyrimidine-2,4(1H,3H)-dione;

(58) 7-{[3-methyl-4-(4-methylpiperazin-1-yl)phenyl]amino}-3-(2-methylphenyl)pyrimido[4,5-d]pyrimidine-2,4(1H,3H)-dione;

(59) 7-{[3-methyl-4-(4-methylpiperazin-1-yl)phenyl]amino}-3-(2-nitrophenyl)pyrimido[4,5-d]pyrimidine-2,4(1H,3H)-dione;

(60) tert-butyl 4-(4-{[6-(2-chlorophenyl)-5,7-dioxo-5,6,7, 8-tetrahydropyrimido[4,5-d]pyrimidin-2-yl]amino}-2-methylphenyl)piperazine-1-carboxylate;

(61) 3-(2-chlorophenyl)-7-({4-[4-(2-methoxyethyl)piperazin-1-yl]phenyl}amino)pyrimido[4,5-d]pyrimidine-2, 4(1H,3H)-dione;

(62) 2-[7-{[3-methyl-4-(4-methylpiperazin-1-yl)phenyl]amino}-2,4-dioxo-1,4-dihydropyrimido[4,5-d]pyrimidin-3(2H)-yl]benzonitrile;

(63) 3-(2-methoxyphenyl)-7-{[3-methyl-4-(4-methylpiperazin-1-yl)phenyl]amino}pyrimido[4,5-d]pyrimidine-2,4(1H,3H)-dione;

(64) 2-[7-{[3-methyl-4-(4-methylpiperazin-1-yl)phenyl]amino}-2,4-dioxo-1,4-dihydropyrimido[4,5-d]pyrimidin-3(2H)-yl]benzamide;

(65) 3-benzyl-7-{[3-methyl-4-(4-methylpiperazin-1-yl) phenyl]amino}pyrimido[4,5-d]pyrimidine-2,4(1H, 3H)-dione;

(66) 3-(2-chlorophenyl)-7-{[3-methyl-4-(4-methylpiperazin-1-yl)phenyl]amino}-1-(pyridin-2-yl)pyrimido[4, 5-d]pyrimidine-2,4(1H,3H)-dione;

(67) 3-(2-chloropyridin-3-yl)-7-{[3-methyl-4-(4-methylpiperazin-1-yl)phenyl]amino}pyrimido[4,5-d]pyrimidine-2,4(1H,3H)-dione;

(68) 3-(2-chlorophenyl)-7-{[3-methyl-4-(4-methylpiperazin-1-yl)phenyl]amino}-1-(1-methyl-1H-pyrazol-3-yl)pyrimido[4,5-d]pyrimidine-2,4(1H,3H)-dione;

(69) 7-{[3-methyl-4-(4-methylpiperazin-1-yl)phenyl]amino}-3-(2-phenylethyl)pyrimido[4,5-d]pyrimidine-2,4(1H,3H)-dione;

(70) 3-(2,5-dichlorophenyl)-7-{[3-methyl-4-(4-methylpiperazin-1-yl)phenyl]amino}pyrimido[4,5-d]pyrimidine-2,4(1H,3H)-dione;

(71) 7-{[3-methyl-4-(4-methylpiperazin-1-yl)phenyl]amino}-3-(3-methylpyridin-2-yl)pyrimido[4,5-d]pyrimidine-2,4(1H,3H)-dione; or

(72) 7-{[3-methyl-4-(4-methylpiperazin-1-yl)phenyl]amino}-3-[2-(methylsulfonyl)phenyl]pyrimido[4,5-d] pyrimidine-2,4(1H,3H)-dione.

11. A pharmaceutical composition comprising a therapeutically effective amount of the compound according to claim 1, or a pharmaceutically acceptable salt thereof, and a pharmaceutically acceptable carrier or diluent.

* * * * *